United States Patent
Kawano et al.

(10) Patent No.: US 8,261,751 B2
(45) Date of Patent: Sep. 11, 2012

(54) GUIDING SYSTEM, POSITION CONTROLLING APPARATUS, AND GUIDING METHOD

(75) Inventors: Hironao Kawano, Machida (JP); Atsushi Chiba, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 544 days.

(21) Appl. No.: 12/498,900

(22) Filed: Jul. 7, 2009

(65) Prior Publication Data

US 2011/0009697 A1    Jan. 13, 2011

Related U.S. Application Data

(60) Provisional application No. 61/078,830, filed on Jul. 8, 2008.

(51) Int. Cl.
*A61B 19/00* (2006.01)
(52) U.S. Cl. ........ 128/899; 600/117; 600/118; 600/109; 600/160; 600/424; 335/219
(58) Field of Classification Search .................. 600/117, 600/118, 242, 424, 109, 160; 128/899; 335/219
See application file for complete search history.

(56) References Cited

U.S. PATENT DOCUMENTS

| | | | |
|---|---|---|---|
| 2003/0060702 A1* | 3/2003 | Kuth et al. | 600/424 |
| 2004/0236180 A1* | 11/2004 | Uchiyama et al. | 600/109 |
| 2005/0093544 A1 | 5/2005 | Ries | |
| 2007/0135680 A1* | 6/2007 | Mizuno | 600/118 |
| 2007/0185398 A1* | 8/2007 | Kimura et al. | 600/424 |
| 2007/0270628 A1* | 11/2007 | Kawano et al. | 600/12 |

FOREIGN PATENT DOCUMENTS

| | | |
|---|---|---|
| DE | 103 41 092 A1 | 4/2005 |
| JP | 10-020214 | 1/1998 |
| JP | 2003-111720 | 4/2003 |
| JP | 2004-321796 | 11/2004 |
| JP | 3898781 | 1/2007 |
| NO | 2003-70728 | 3/2003 |

OTHER PUBLICATIONS

Extended European Search Report dated Nov. 5, 2009.

* cited by examiner

*Primary Examiner* — Samuel G. Gilbert
*Assistant Examiner* — Sunita Reddy
(74) *Attorney, Agent, or Firm* — Scully, Scott, Murphy & Presser, P.C.

(57) ABSTRACT

A guiding system includes a capsule-type apparatus and a position controlling apparatus. The capsule-type apparatus includes a permanent magnet, which is fixed to a capsule-shaped casing, and is introduced into a subject. The position controlling apparatus includes a relative position controlling mechanism that changes a relative position between a predetermined axis and the subject, and a magnetic field generating mechanism that forms, in a space in which the subject is laid, a magnetic field that includes at least one of a component of a trapping magnetic field that attracts the permanent magnet to the predetermined axis and a component of a gradient magnetic field that attracts the permanent magnet in a direction same as or opposite to a direction in which the relative position is changed.

21 Claims, 45 Drawing Sheets

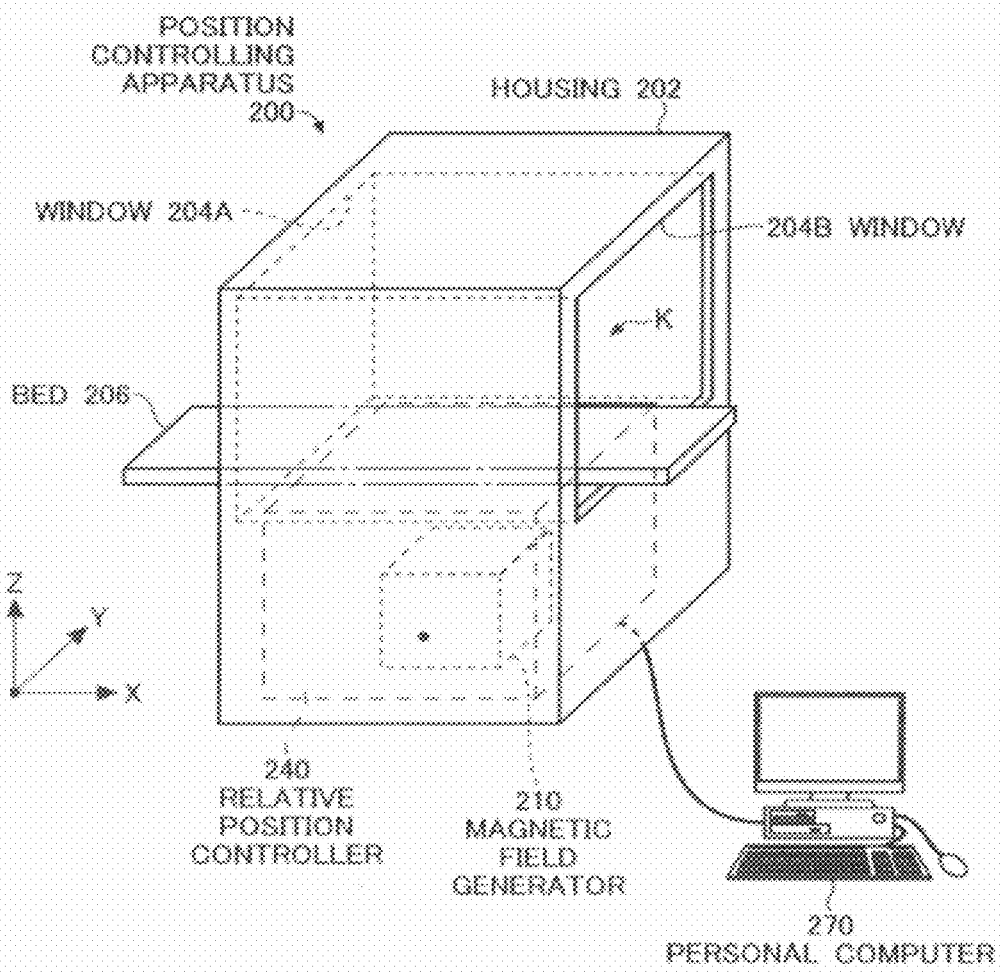

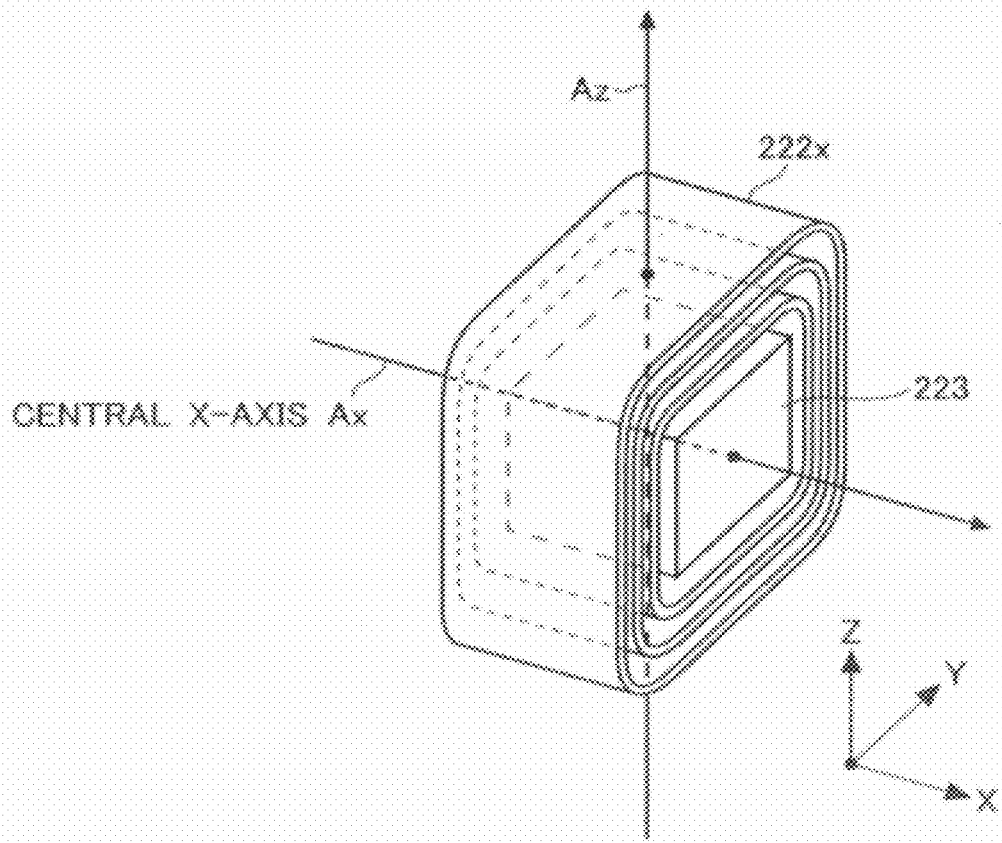

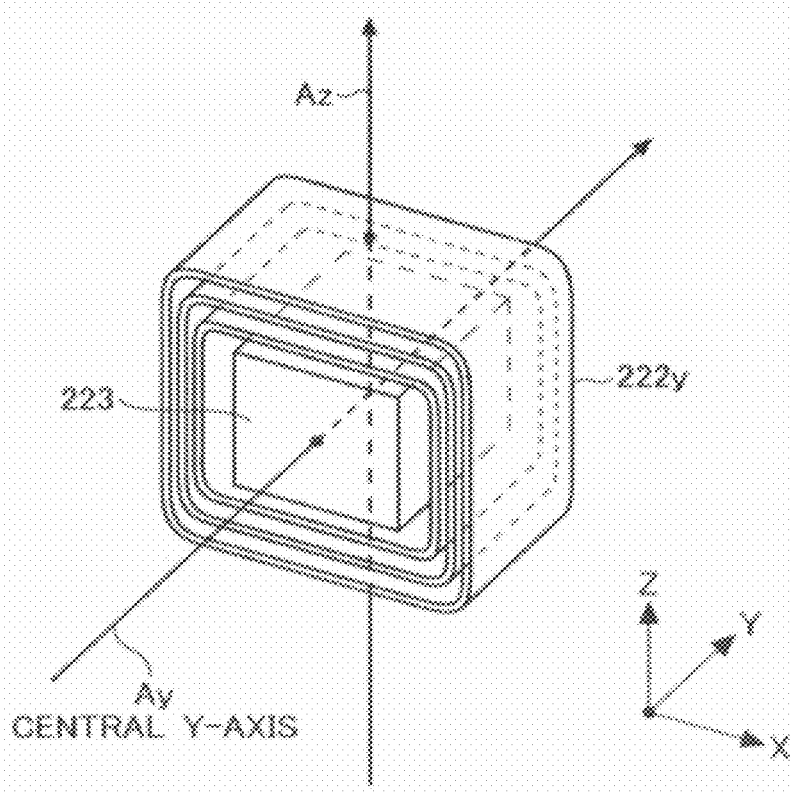

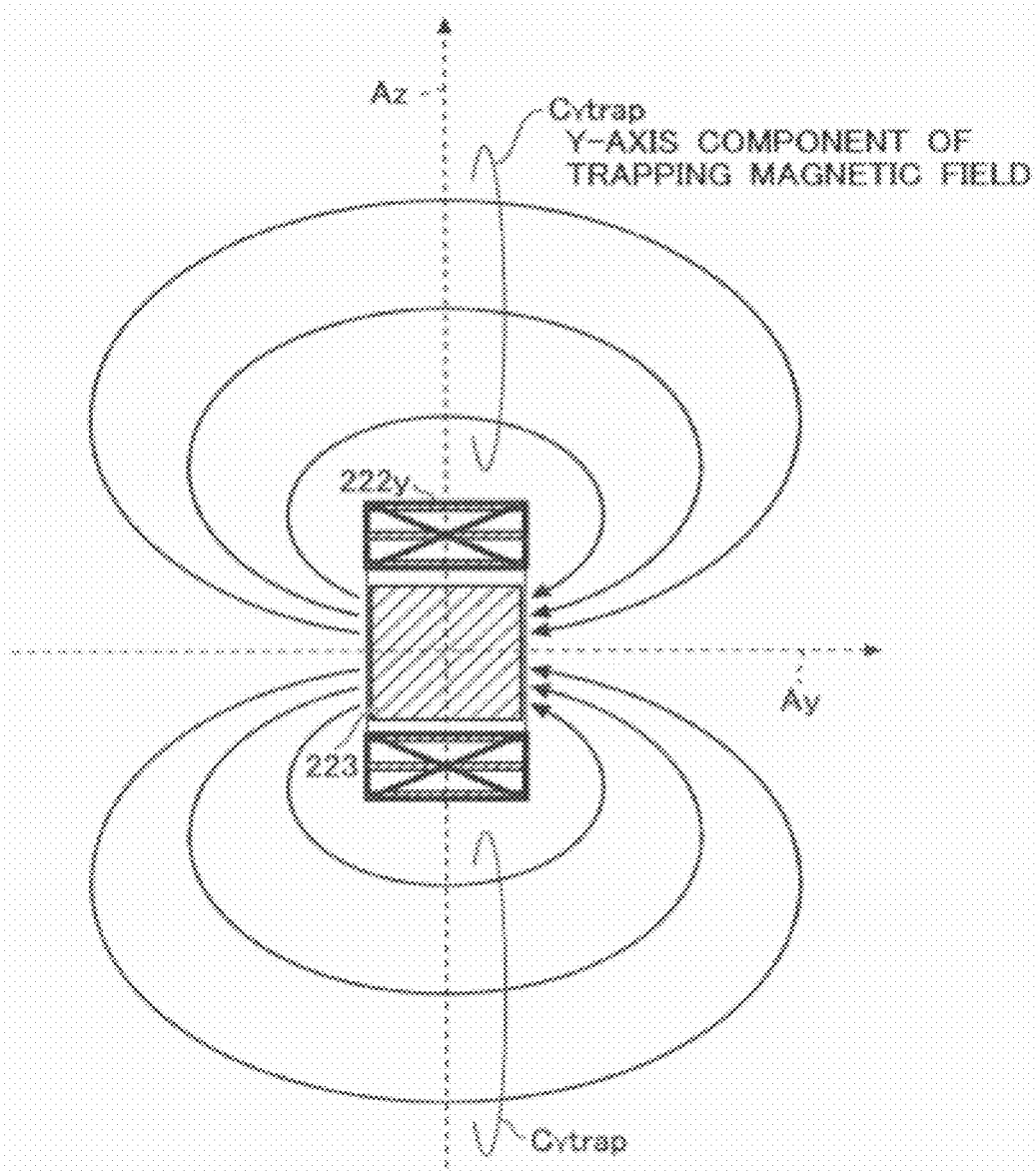

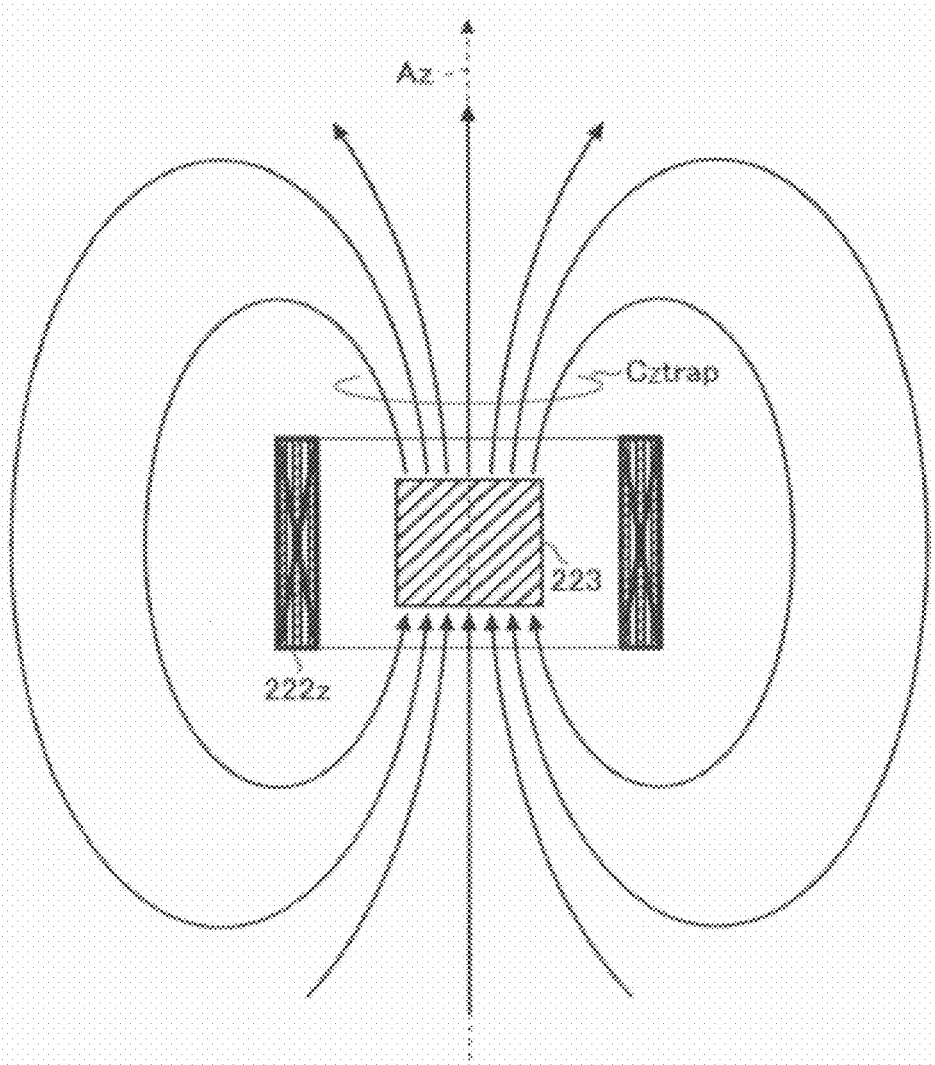

FIG. 16
(a)
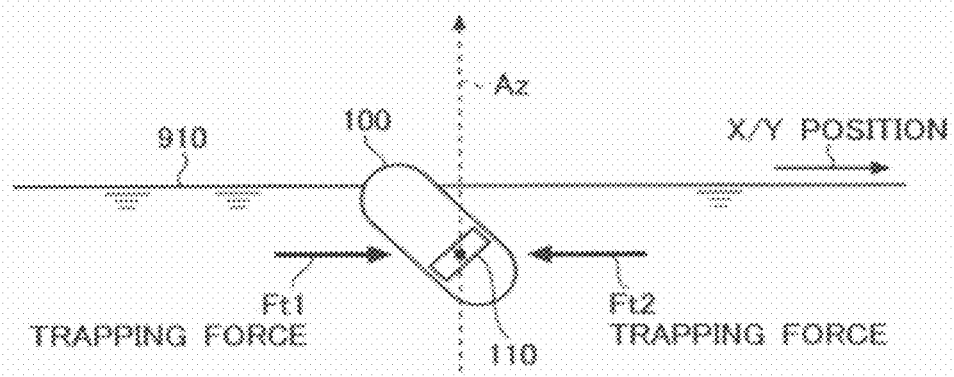
(b)
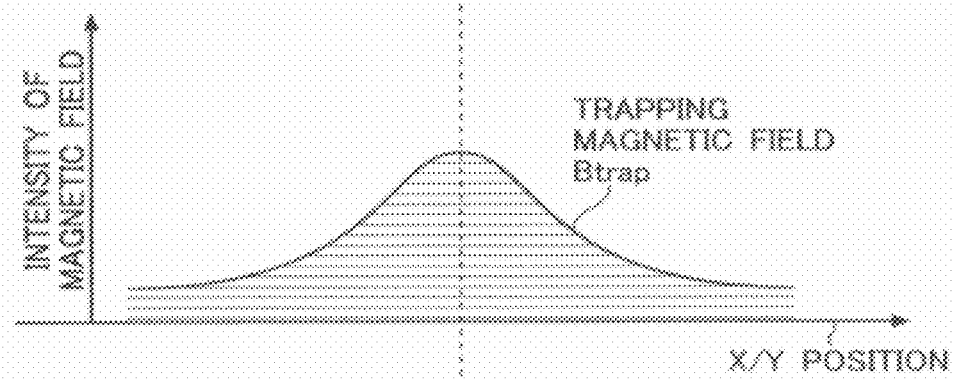

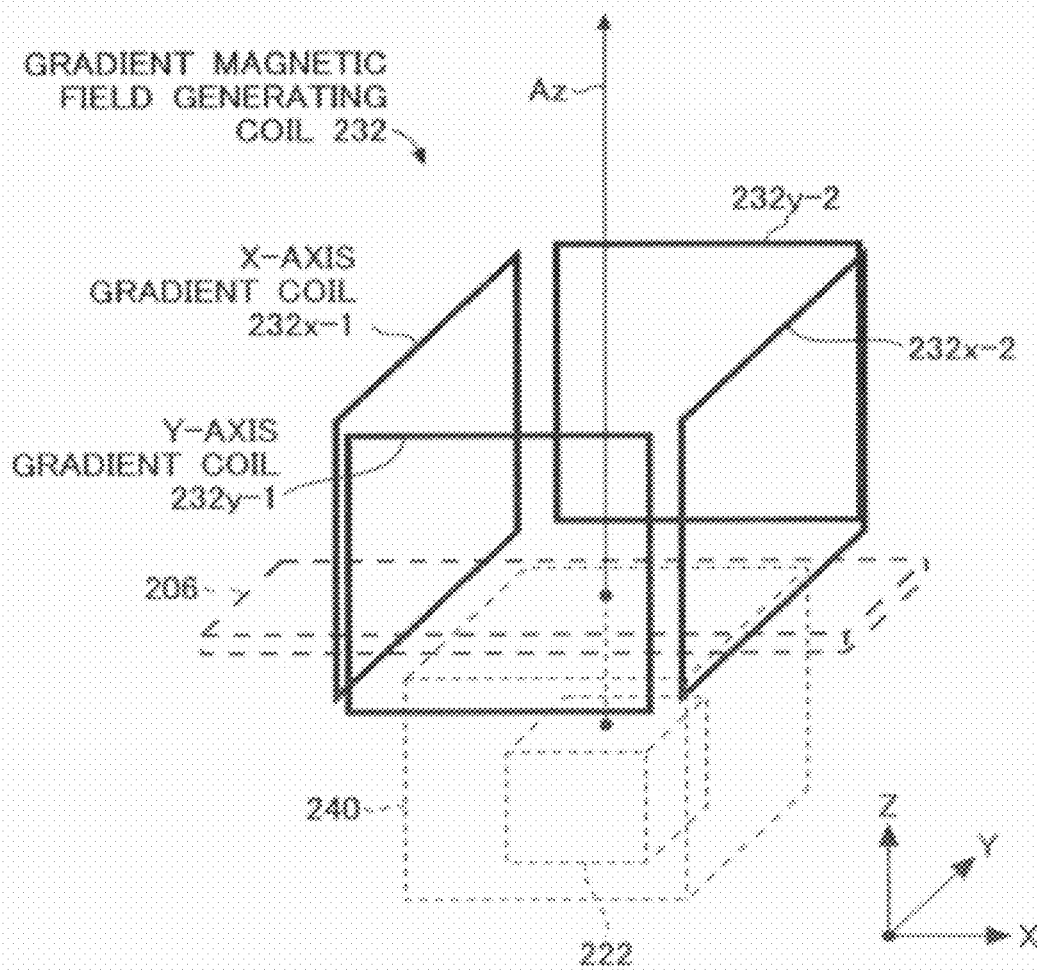

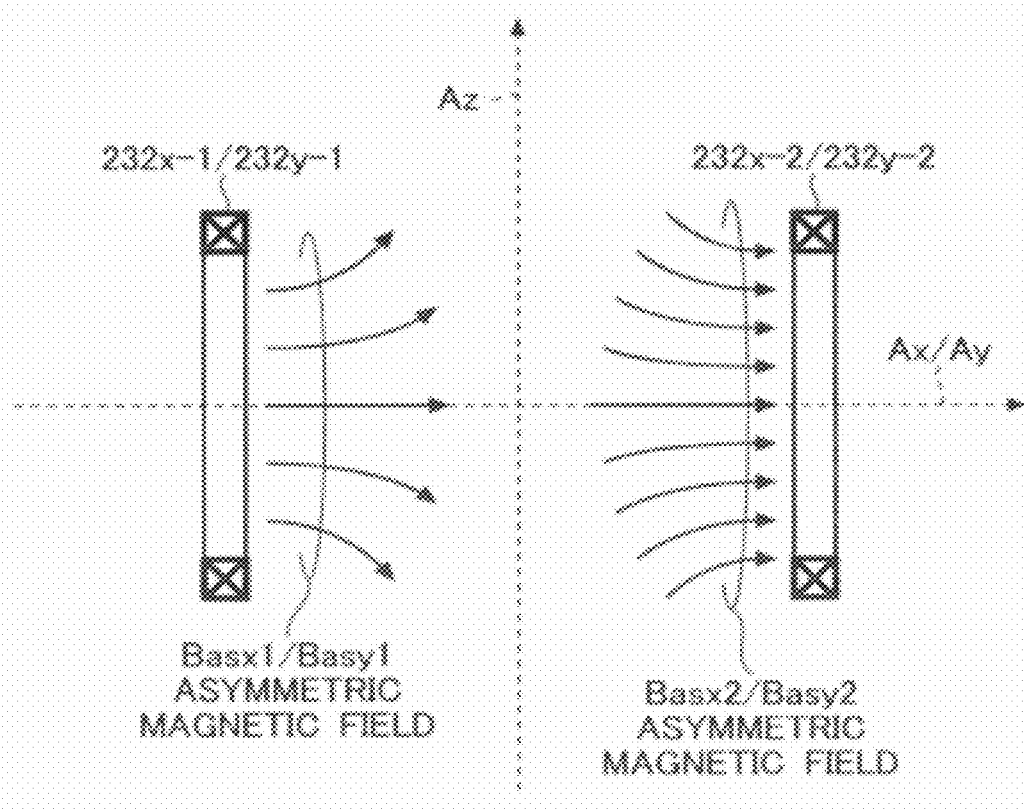

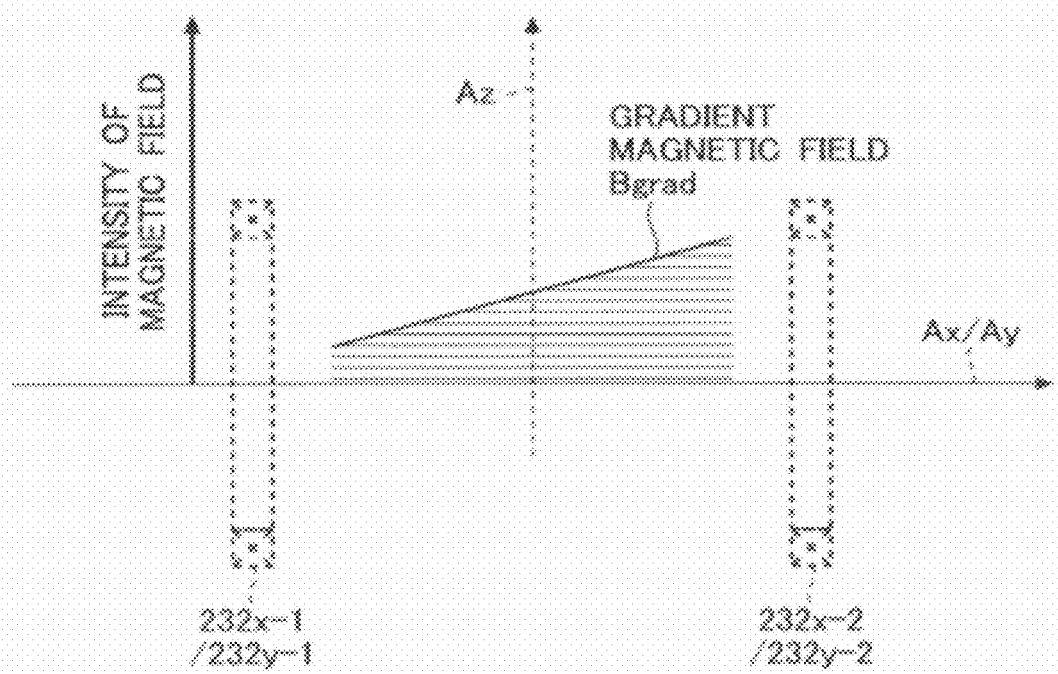

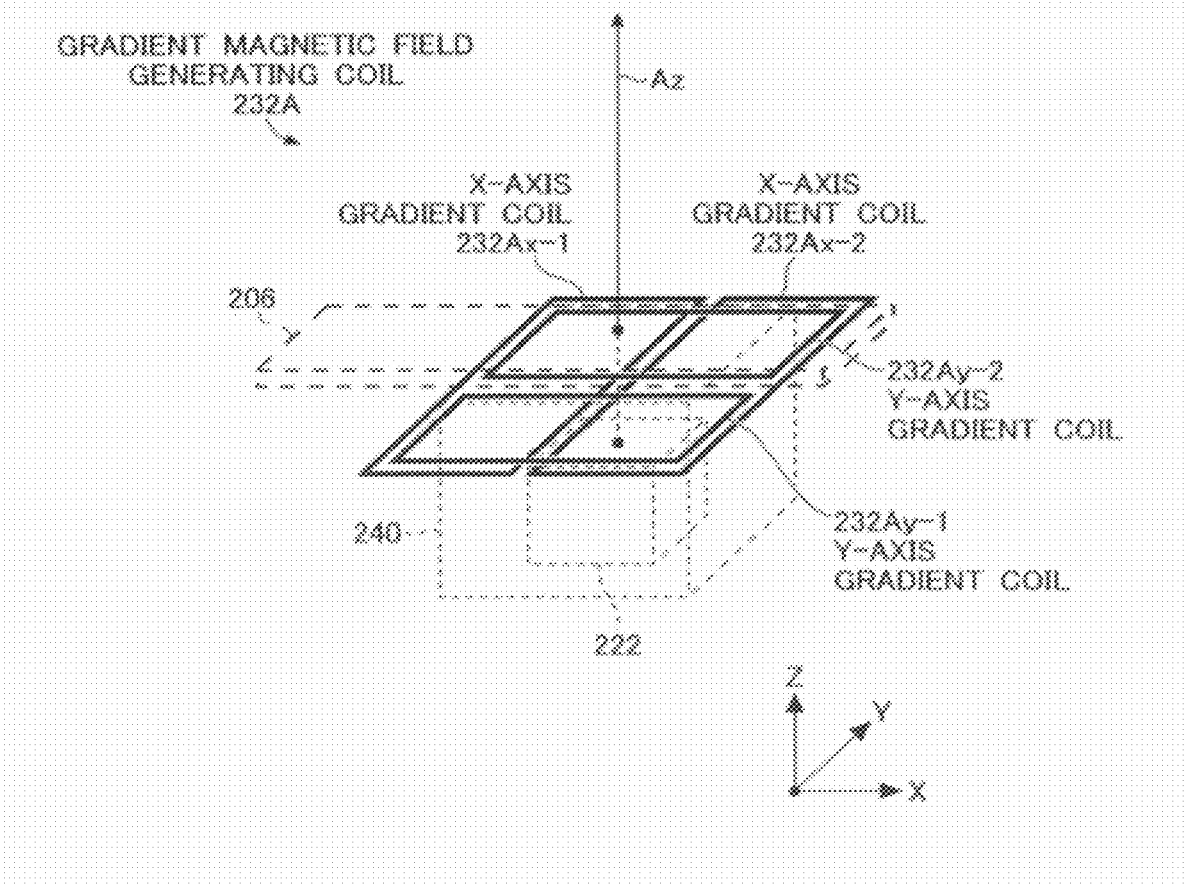

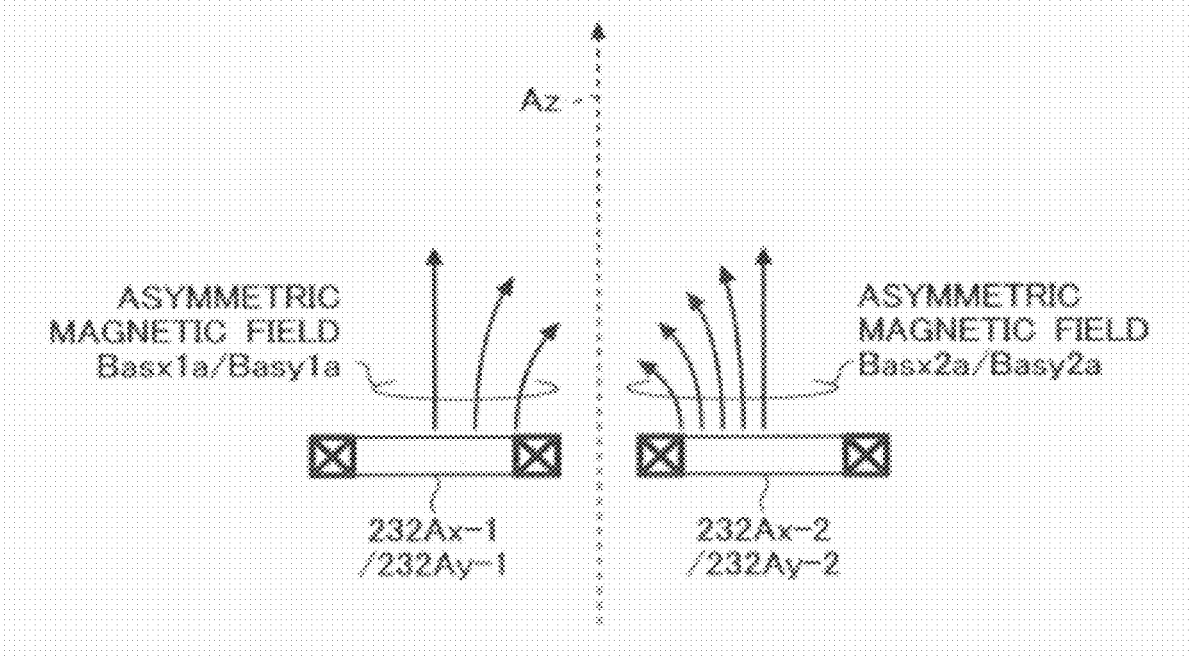

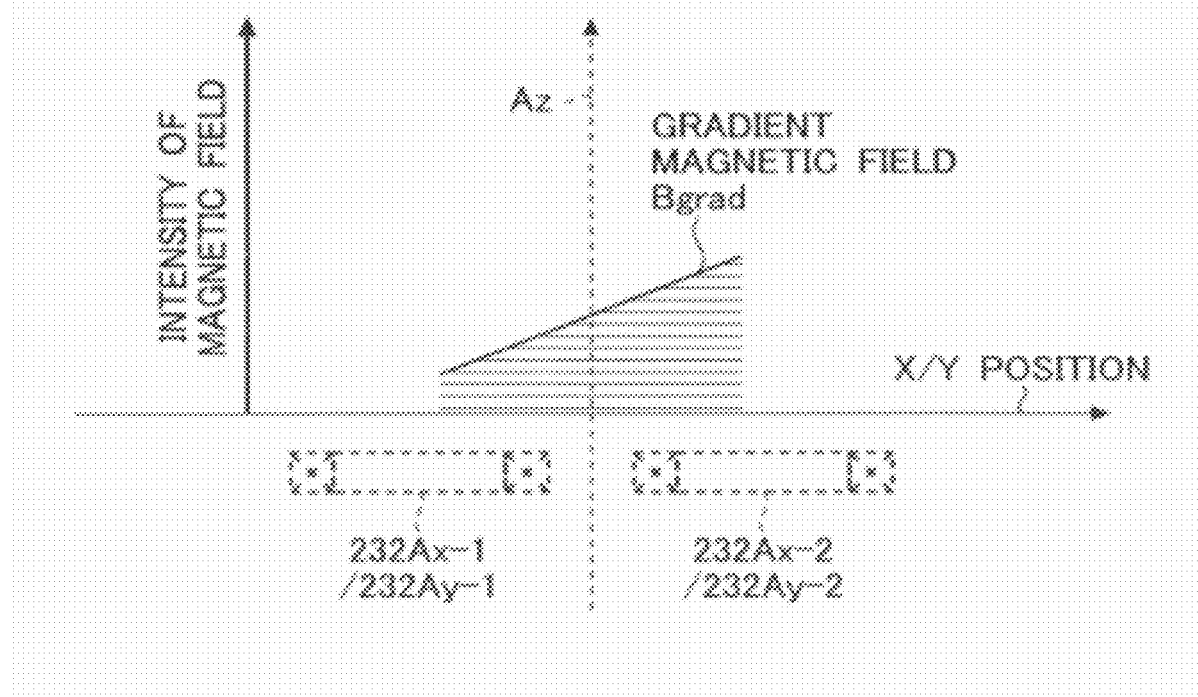

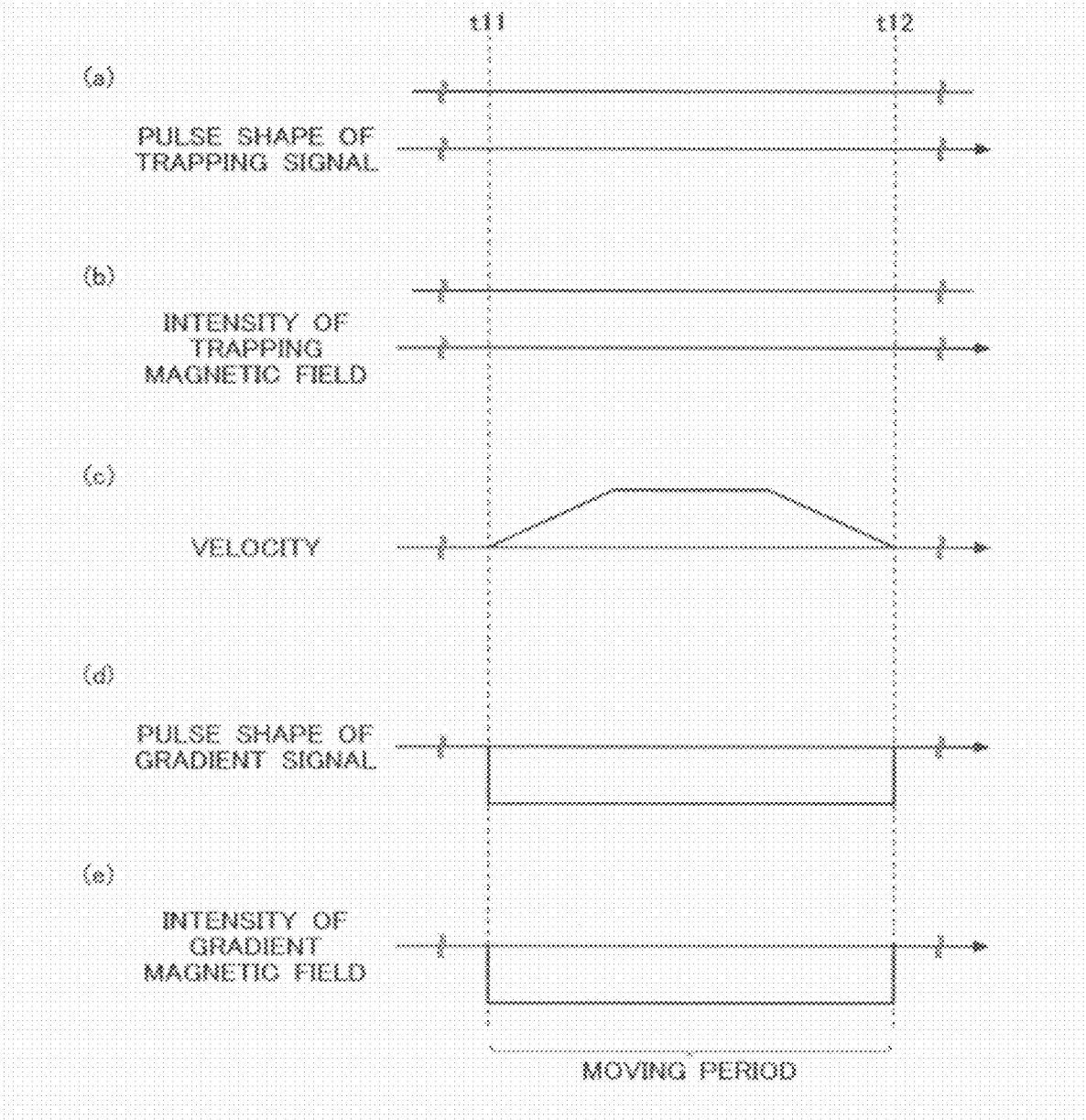

FIG. 24B
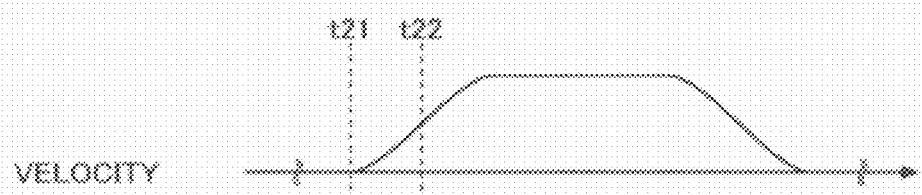
(a) VELOCITY
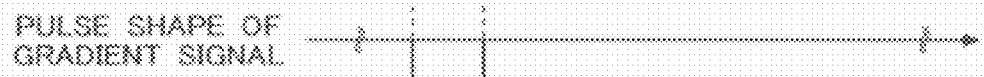
(b) PULSE SHAPE OF GRADIENT SIGNAL
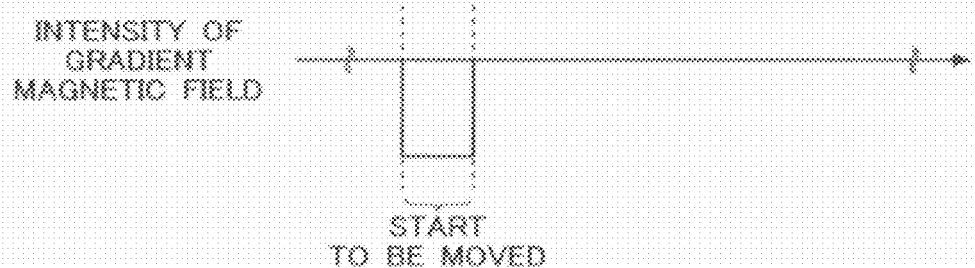
(c) INTENSITY OF GRADIENT MAGNETIC FIELD
START TO BE MOVED

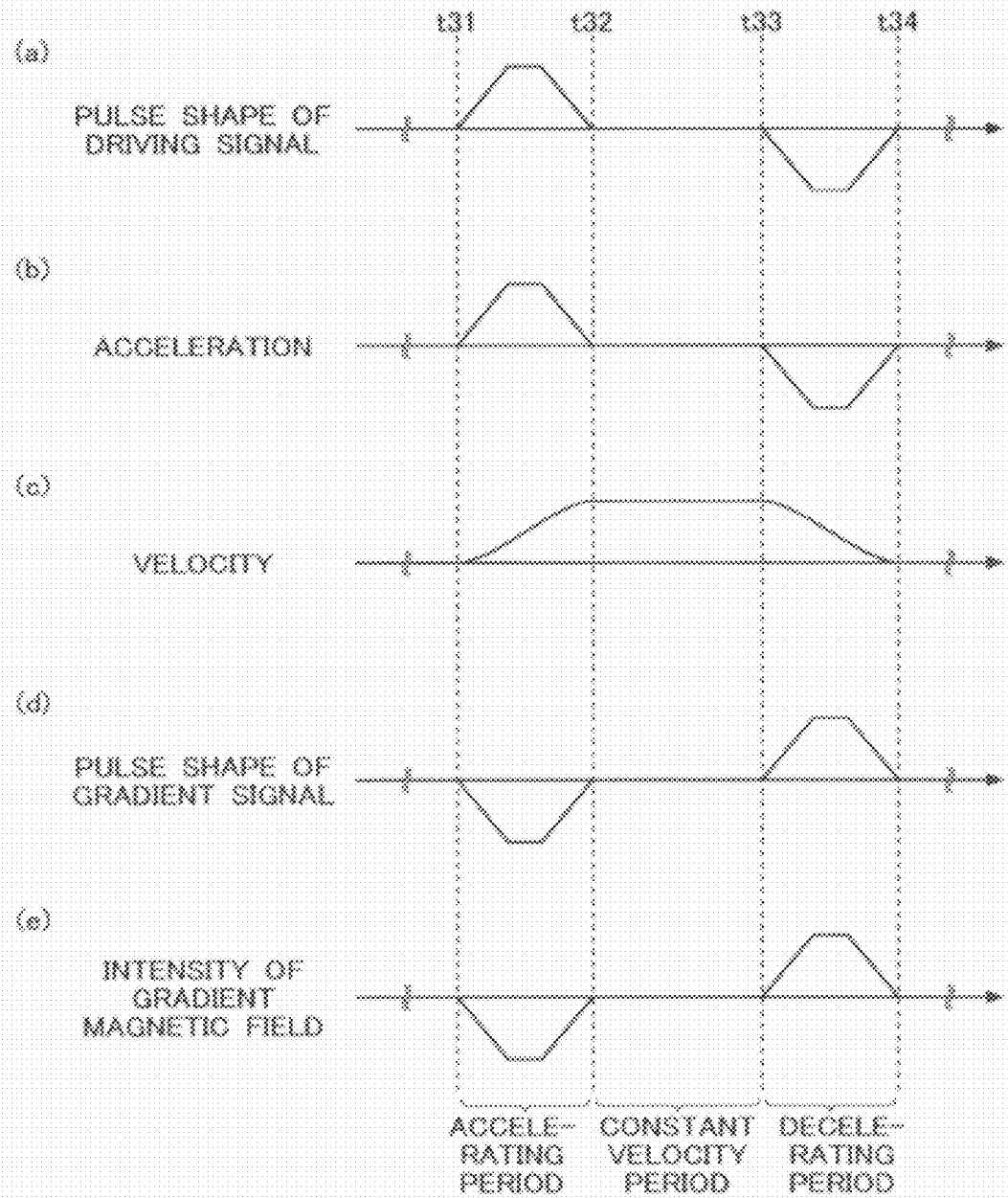

FIG. 25
(a)
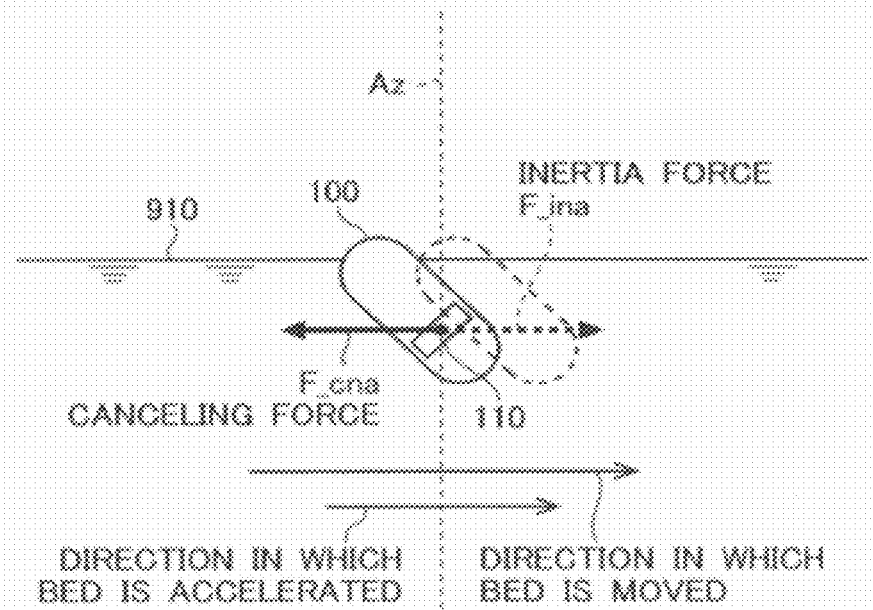
(b)
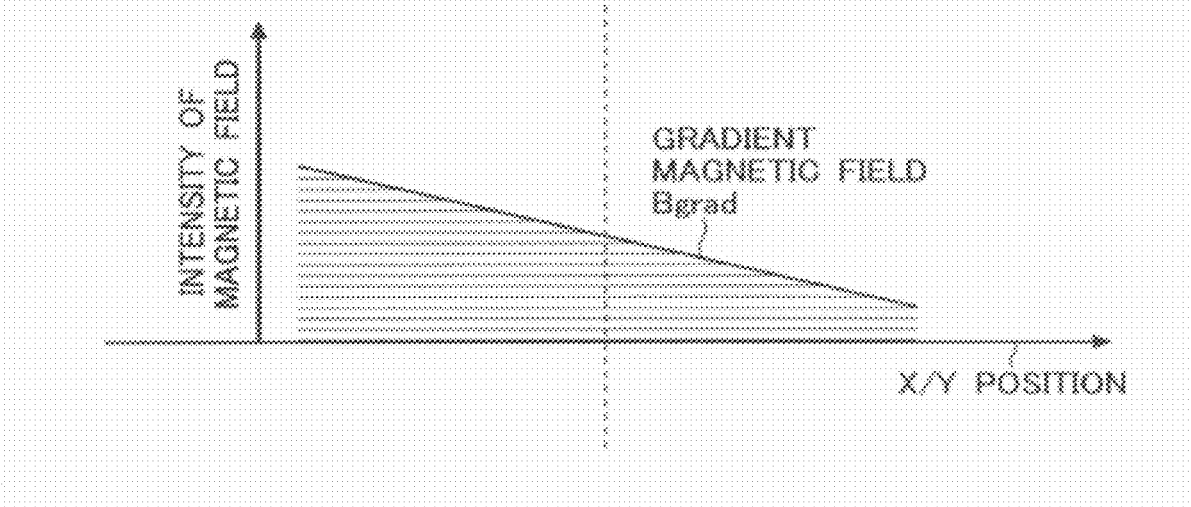

FIG. 26
(a)
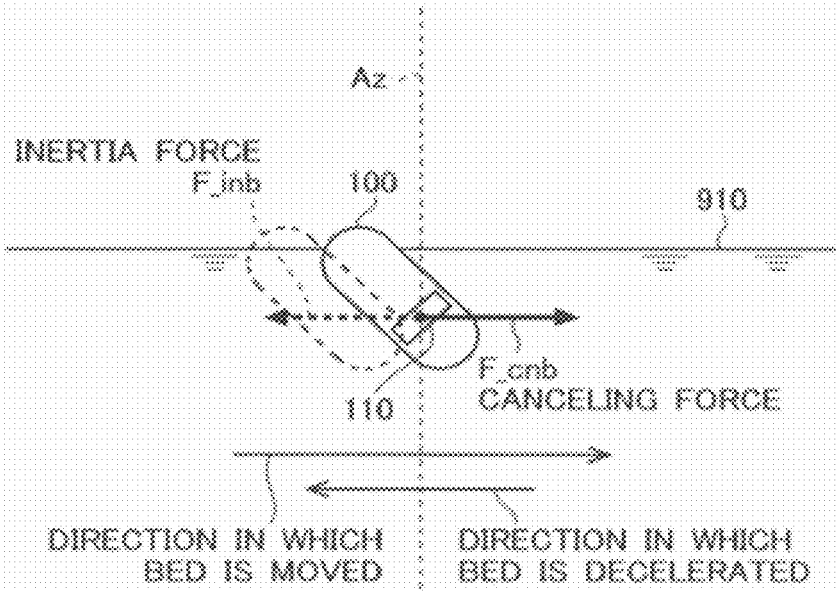
(b)
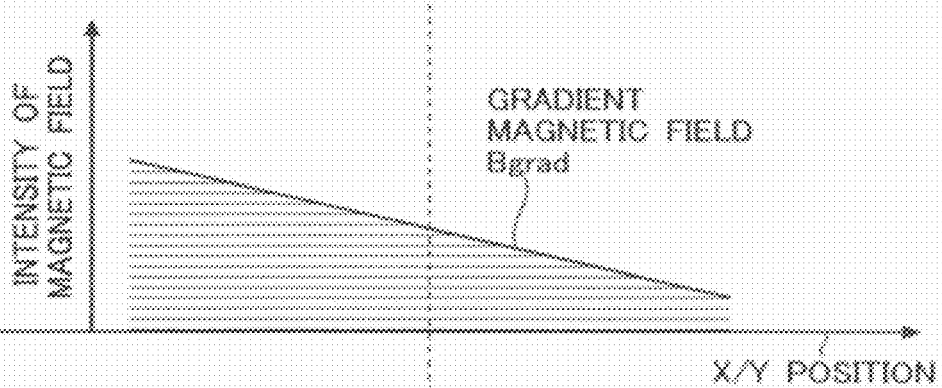

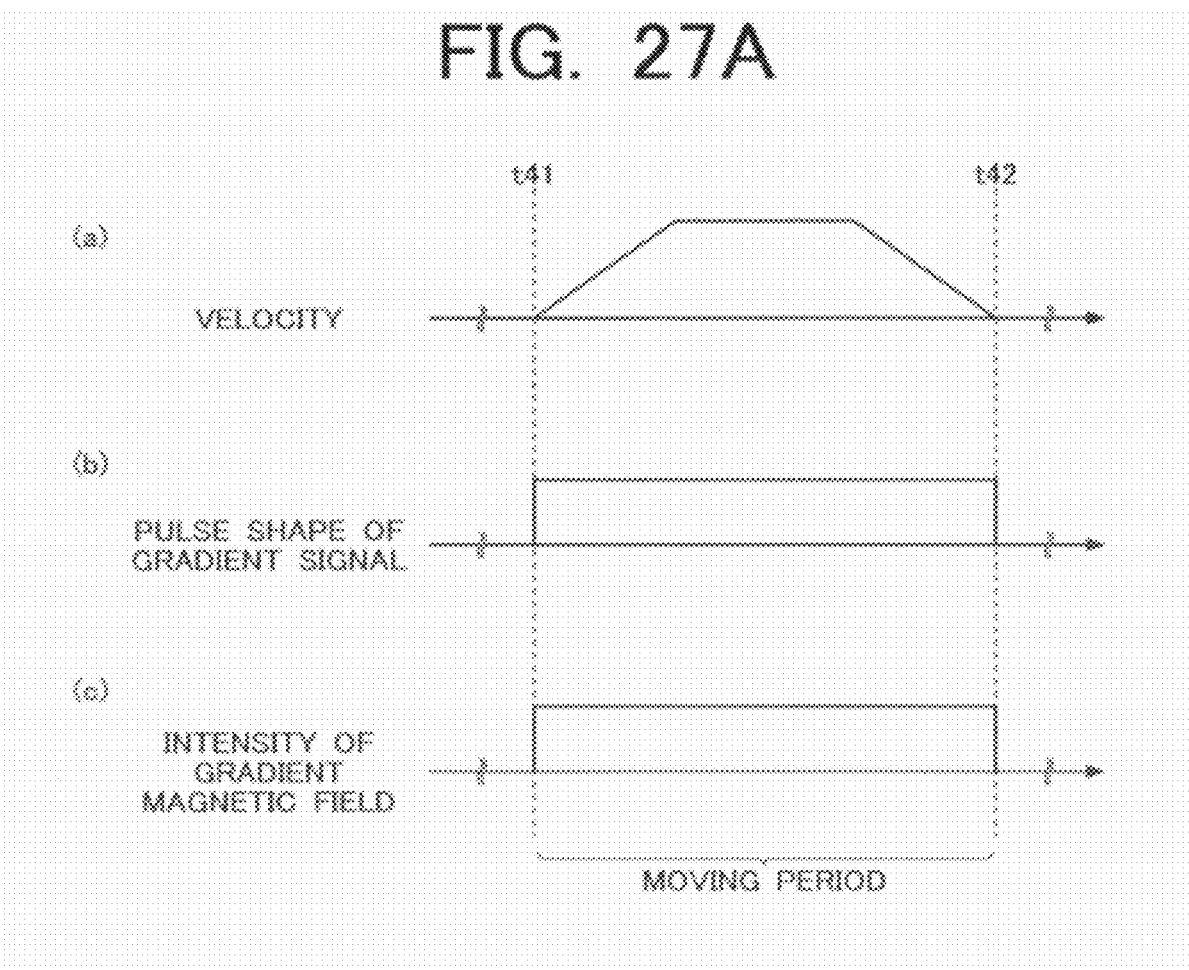

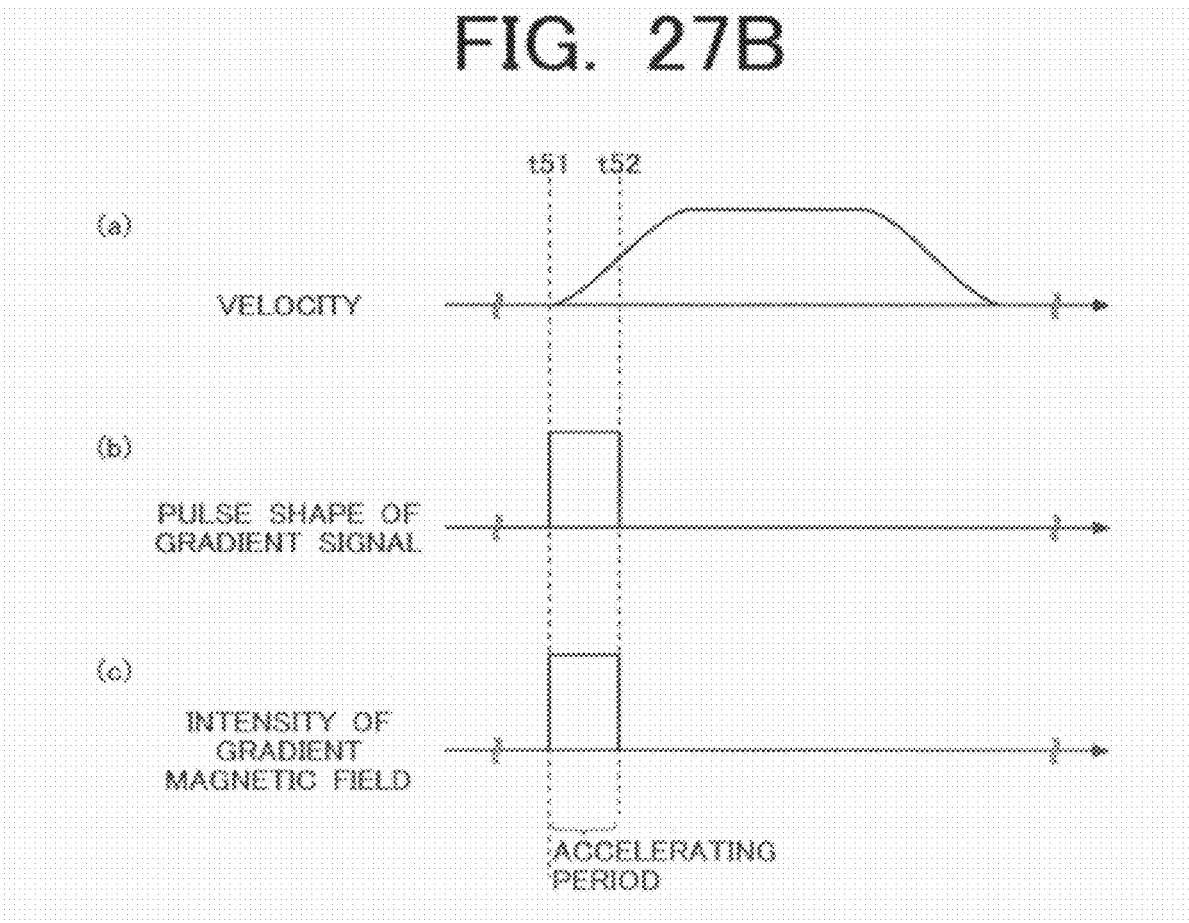

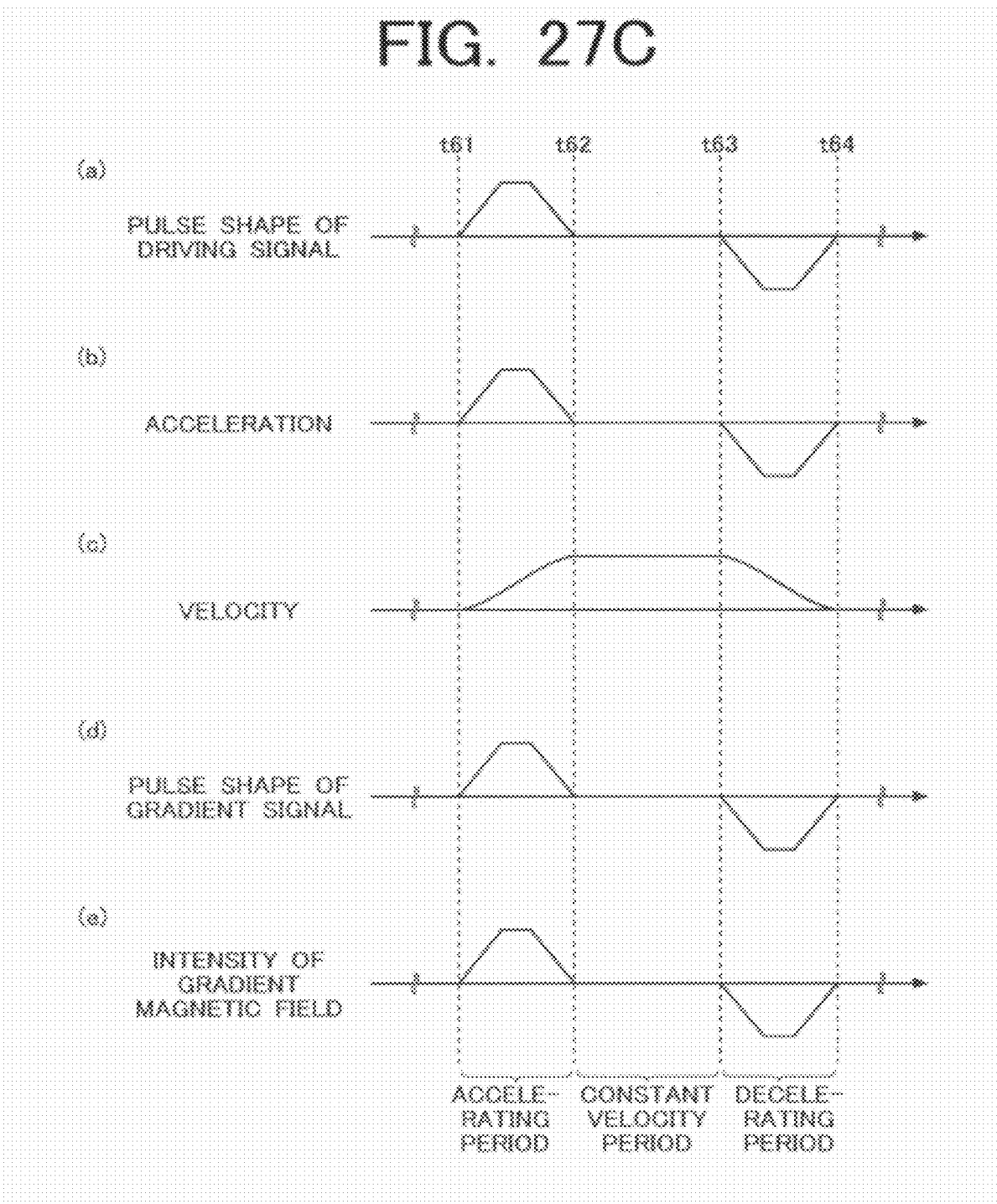

FIG. 28
(a)
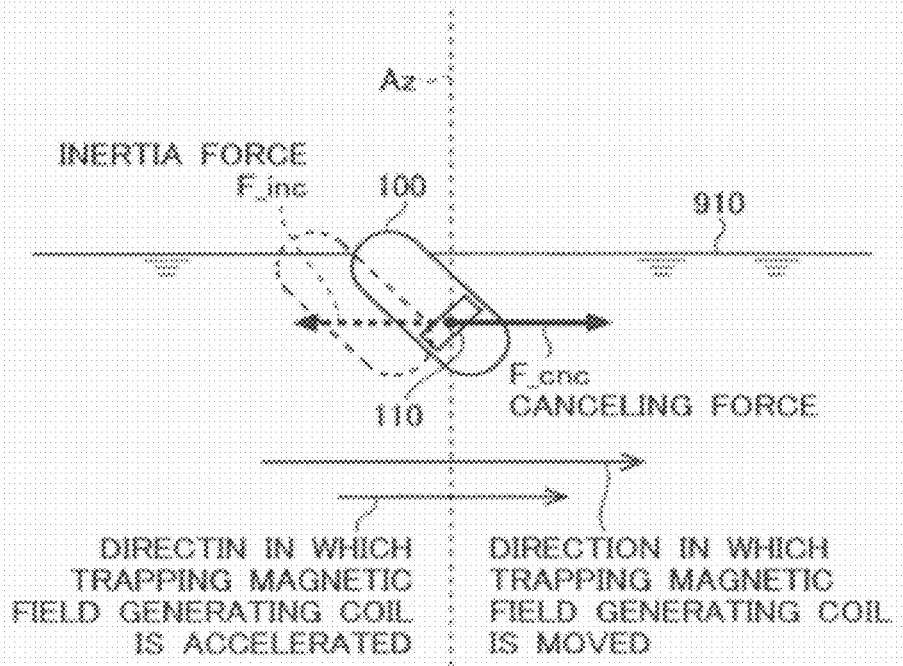
(b)
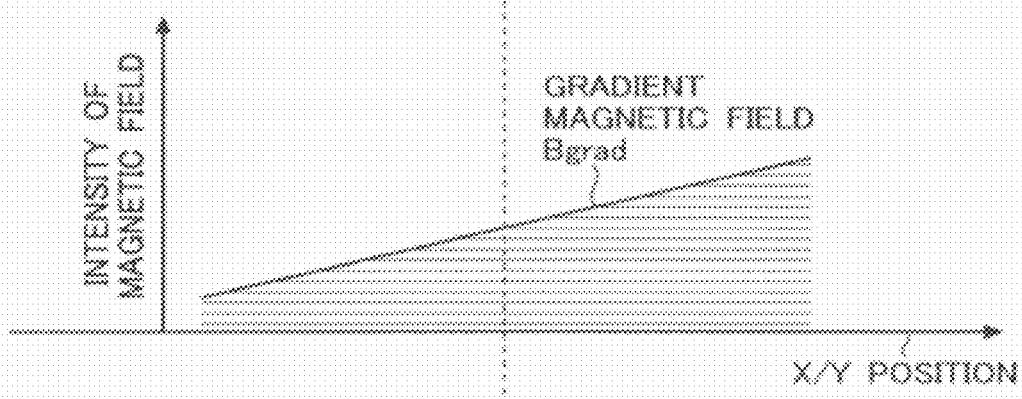

FIG. 29
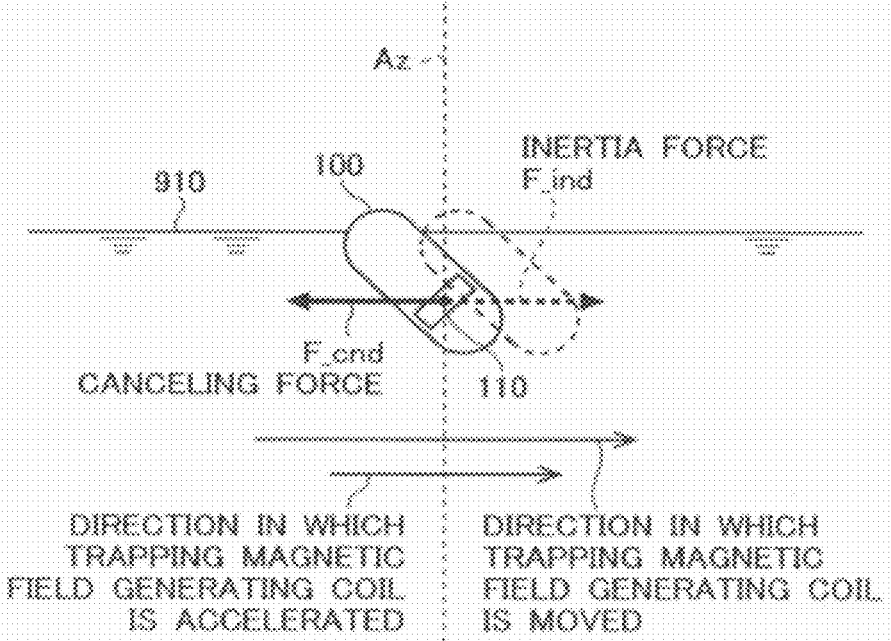
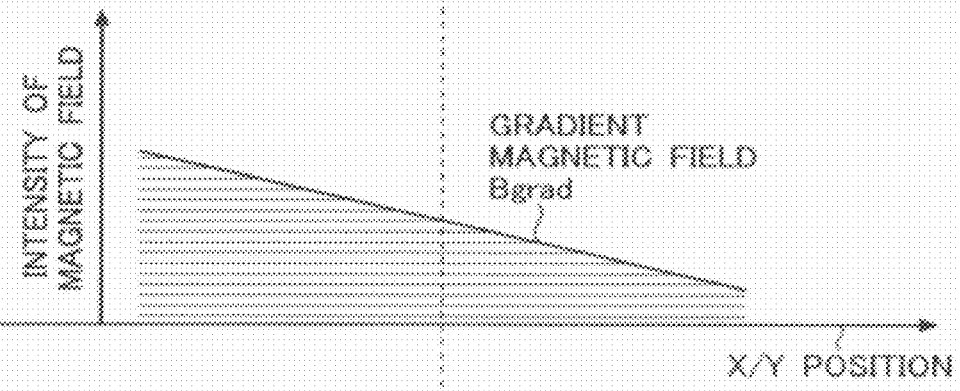

GUIDING SYSTEM, POSITION CONTROLLING APPARATUS, AND GUIDING METHOD

CROSS-REFERENCE TO RELATED APPLICATIONS

This application claims the benefit of U.S. Provisional Application No. 61/078,830, filed on Jul. 8, 2008, the entire contents of which are incorporated herein by reference.

BACKGROUND OF THE INVENTION

1. Field of the Invention

The present invention relates a guiding system, a position controlling apparatus, and a guiding method. Particularly, the present invention relates to a guiding system, a position control apparatus, and a guiding method for guiding the position of a body-insertable apparatus in a subject.

2. Description of the Related Art

As examples of an apparatus for performing internal observation of a subject, such as a human or an animal, there are endoscopes that include tube-shaped probes (hereinafter, "endoscope") and capsule-type endoscopes (hereinafter, "capsule endoscope").

As examples of endoscopes, there are electric endoscopes that include charge coupled device (CCD) sensors and complementary metal oxide semiconductor (CMOS) sensors, which are provided on the tips of the endoscopes, and fiber scopes that include a bundle of optical fibers passed through a probe. The probe of such an endoscope is inserted from the mouth or the anus of a subject to take in-vivo images of the subject (see, Japanese Patent No. 3898781).

In contrast, a capsule endoscope is a capsule-type body insertable apparatus that is introduced into a subject, and it has a size swallowable by a human or an animal. The capsule endoscope is introduced into the subject from, for example, the mouth. The capsule endoscope that is introduced into the subject takes in-vivo images of the subject regularly, and transmits the in-vivo images of the subject as wireless signals to a receiving apparatus outside the subject (see, Japanese Patent Application Laid-open No. 2003-70728).

An observer individually or successively replays a plurality of images that are obtained by an endoscope or a capsule endoscope. By observing the images, the observer performs internal observation of the subject.

When a capsule endoscope is introduced into a subject, it is usually movable. Therefore, the position and the posture of the capsule endoscope in the subject are not restricted as long as they are not restricted by the inner wall of the lumen of the subject. However, if the position and the posture of the capsule endoscope in the subject are not determined, it is difficult for the observer to specify the part of the interior of the subject of which images are taken by the capsule endoscope. If the position and the posture of the capsule endoscope in the subject cannot be controlled, it is difficult for the observer to observe a target part of the interior of the subject.

To deal with the above inconvenience, a permanent magnet is mounted on a capsule endoscope. By applying an externally-formed magnetic field to the permanent magnet, the position and the posture of the capsule endoscope are controlled. For example, to control the position of a capsule endoscope that flows in liquid stored in the stomach of a subject, the magnetic field (hereinafter, "trapping magnetic field") for maintaining the position and the posture of the permanent magnet is externally applied to the permanent magnet that is fixed in the capsule endoscope.

The difference in elevation of the intensity (hereinafter, "gradient") of the trapping magnetic field is small near a target position where the capsule endoscope is to be held (hereinafter, "trapping position"). Thus, it is difficult to keep the capsule endoscope in a trapped state at a desirable position when the relative position between the subject and the capsule endoscope is changed. In other words, it is difficult to achieve a steep gradient of distribution of intensity of the trapping magnetic field near the trapping position to hold the capsule endoscope in the trapping position against a force, such as a frictional force or an inertia force, which is applied to the capsule endoscope.

For example, when the relative position between the subject and the capsule endoscope flowing in the liquid introduced into the subject is changed by moving a bed on which the subject is laid with respect to the trapping position, an inertia force and a frictional force of the liquid are applied to the capsule endoscope in the subject because the bed is moved. Accordingly, the capsule endoscope is to move with the subject. Because the gradient of the trapping magnetic field to prevent the capsule endoscope from moving is gentle near the trapping position, it is difficult to maintain the state where the capsule endoscope is trapped in a desirable position. The difficulty is similarly caused when the trapping position is moved while the subject is in a fixed state or when the bed and the trapping position are moved relatively.

SUMMARY OF THE INVENTION

A guiding system according to one aspect of the present invention includes a capsule-type apparatus that includes a permanent magnet, which is fixed to a capsule-shaped casing, and that is introduced into a subject. The guiding system further includes a position controlling apparatus that includes a relative position controlling mechanism that changes a relative position between a predetermined axis and the subject, and a magnetic field generating mechanism that forms, in a space in which the subject is laid, a magnetic field that includes at least one of a component of a trapping magnetic field that attracts the permanent magnet to the predetermined axis and a component of a gradient magnetic field that attracts the permanent magnet in a direction same as or opposite to a direction in which the relative position is changed.

A position controlling apparatus according to another aspect of the present invention includes a permanent magnet fixed to a capsule-shaped casing, and guides a position of a capsule-type apparatus that is introduced into a subject. The position controlling apparatus includes a relative position controlling mechanism that changes a relative position between a predetermined axis and the subject, and a magnetic field generating mechanism that forms, in a space in which the subject is laid, a magnetic field that includes at least one of a component of a trapping magnetic field that attracts the permanent magnet to the predetermined axis and a component of a gradient magnetic field that attracts the permanent magnet in a direction same as or opposite to a direction in which the relative position is changed.

A method according to still another aspect of the present invention is for guiding a position of a capsule-type apparatus that includes a permanent magnet fixed in a capsule-shaped casing, and that is introduced into a subject. The method includes a trapping magnetic field generating step of forming a trapping magnetic field that attracts the permanent magnet to a predetermine axis in a space in which the subject is laid, a relative position controlling step of changing a relative position between the predetermined axis and the subject, and a gradient magnetic field generating step of forming, in the space, a gradient magnetic field that attracts the permanent magnet in a direction same as or opposite to a direction in which the relative position is changed.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 5 is a perspective view of a schematic configuration example of a position control apparatus of the capsule endoscope system according to the first embodiment of the present invention;

FIG. 9A is a perspective view of an example of an X-axis trapping coil of the trapping magnetic field generating coil shown in FIG. 8;

FIG. 10A is a perspective view of an example of a Y-axis trapping coil of the trapping magnetic field generating coil shown in FIG. 8;

FIG. 10B is a schematic diagram of a Y-axis component of the trapping magnetic field that is formed by the Y-axis trapping coil shown in FIG. 10A;

FIG. 11B is a schematic diagram of a Z-axis component of the trapping magnetic field that is formed by the Z-axis trapping coil shown in FIG. 11A;

FIG. 16 is a diagram representing the relationship between the distribution of the intensity of the trapping magnetic field and trapping forces that are applied to the capsule endoscope because of the trapping magnetic field in the first embodiment of the present invention;

FIG. 18 is a perspective view of an example of the gradient magnetic field generating coil according to the first embodiment of the present invention;

FIG. 19A is a schematic diagram of an example of asymmetric magnetic fields that are formed by X/Y-axis gradient coils of the gradient magnetic field generating coil shown in FIG. 18;

FIG. 19B is a diagram of an example of the distribution of the intensity of the gradient magnetic field that is formed by the X/Y-axis gradient coils shown in FIG. 19A;

FIG. 20 is a perspective view of an example of a gradient magnetic field generating coil of Modification 1-3 of the first embodiment of the present invention;

FIG. 21A is a schematic diagram of an example of asymmetric magnetic fields that are respectively formed by X/Y-axis gradient coils of the gradient magnetic field generating coil shown in FIG. 20;

FIG. 21B is a diagram of an example of the distribution of the intensity of the gradient magnetic field that is formed by the X/Y-axis gradient coils shown in FIG. 21A;

FIG. 24A is a timing chart for explaining Operation pattern 1 according to the first embodiment of the present invention;

FIG. 24B is a timing chart for explaining Operation pattern 2 according to the first embodiment of the present invention;

FIG. 24C is a timing chart for explaining Operation pattern 3 according to the first embodiment of the present invention;

FIG. 25 is a schematic diagram of an example of the force that is generated in the capsule endoscope and the gradient magnetic field that is formed in a detecting space while the bed is accelerated in Operation pattern 3 represented in FIG. 24C;

FIG. 26 is a schematic diagram of an example of the force that is generated in the capsule endoscope and the gradient magnetic field that is formed in the detecting space while the bed is decelerated in Operation pattern 3 represented in FIG. 24C;

FIG. 27A is a timing chart for explaining Operation pattern 4 according to the first embodiment of the present invention;

FIG. 27B is a timing chart for explaining Operation pattern 5 according to the first embodiment of the present invention;

FIG. 27C is a timing chart for explaining Operation pattern 6 according to the first embodiment of the present invention;

FIG. 28 is a schematic diagram of an example of the force that is generated in the capsule endoscope and the gradient magnetic field that is formed in the detecting space in Operation pattern 6 represented in FIG. 27C;

FIG. 29 is a schematic diagram of an example of the force generated in the capsule endoscope and the gradient magnetic field that is formed in the detecting space while the bed is decelerated in Operation pattern 6 represented in FIG. 27C;

DETAILED DESCRIPTION OF THE PREFERRED EMBODIMENTS

A capsule endoscope system 1 according to a first embodiment of the present invention is explained in detail below with reference to the accompanying drawings. In the first embodiment, the capsule endoscope system 1 using, as a body insertable apparatus, a capsule endoscope 100 that is introduced into a subject from the mouth and floats in liquid stored in the stomach, the small intestine, or the large intestine of the subject is taken as an example. A capsule endoscope that includes a plurality of imaging units, i.e., a multi-eye capsule endoscope, is taken as an example of the capsule endoscope 100. Alternatively, various body-insertable apparatuses can be used. For example, a single-eye or multi-eye capsule endoscope that takes in-vivo images of the subject by performing an image-taking operation while moving through the lumen from the esophagus to the anus of the subject can be used.

Figure 1:
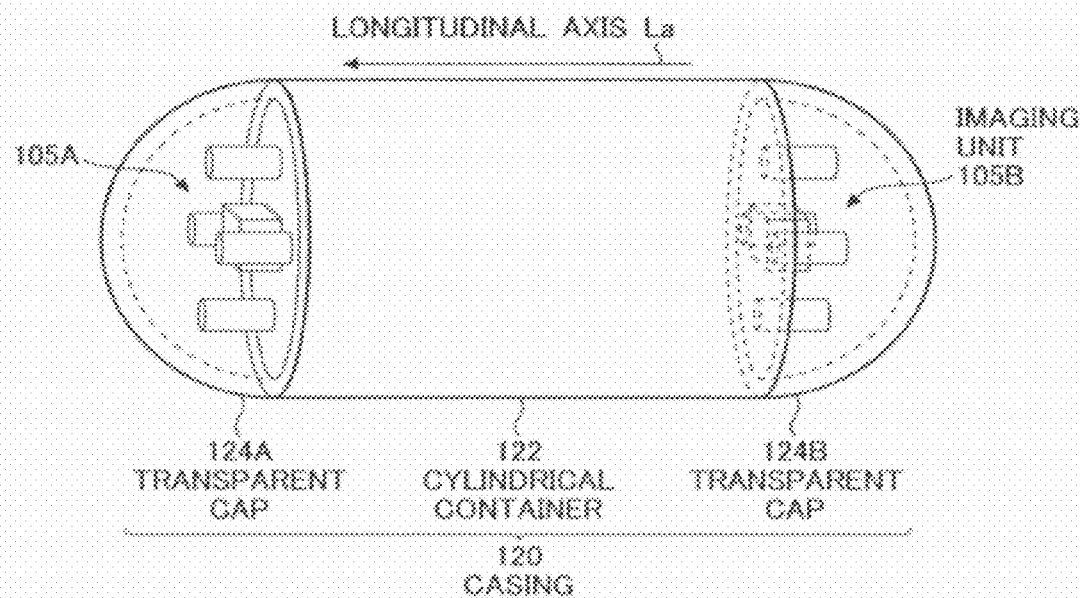
FIG. 1 is a perspective view of a schematic outer configuration example of a capsule endoscope according to a first embodiment of the present invention.
Figure 2:
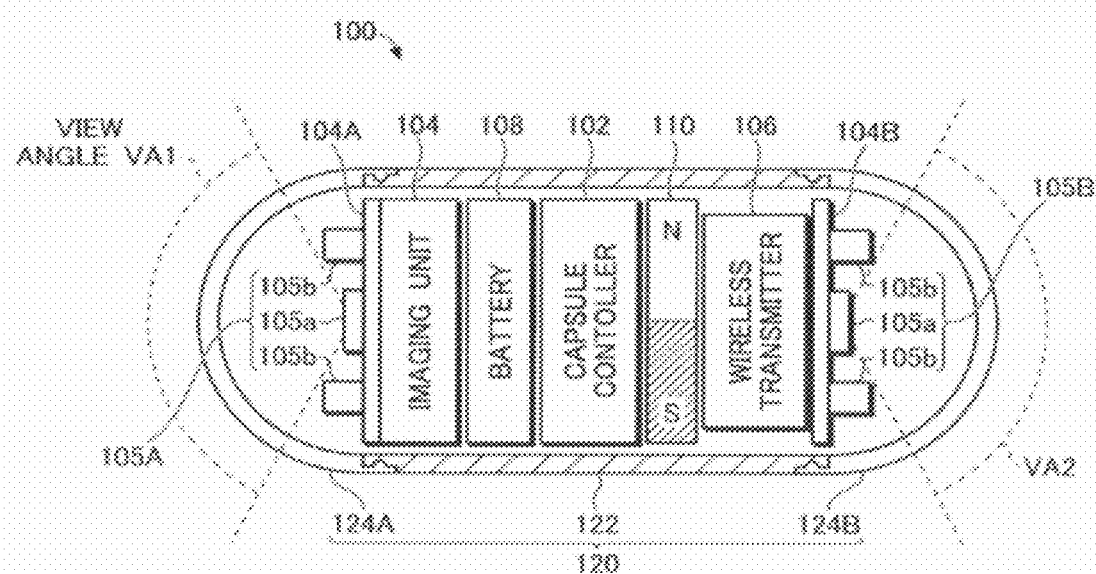
FIG. 2 is a block diagram of a schematic configuration example of the capsule endoscope according to the first embodiment of the present invention.

FIG. 1 is a perspective view of a schematic outer configuration example of the capsule endoscope 100 according to the first embodiment. FIG. 2 is a block diagram of a schematic configuration example of the capsule endoscope 100 according to the first embodiment.

As shown in FIG. 1, the capsule endoscope 100 includes a casing 120 that includes a cylindrical container 122 that is hollow and that has openings on both ends, and dome-shaped transparent caps 124A and 124B that are provided to the ends of the cylindrical container 122 where the openings are formed. The casing 120 is sealed watertight because the caps 124A and 124B are fitted into the two openings of the cylindrical container 122. Imaging units 105A and 105B that illuminate the interior of the subject and take in-vivo images of the subject are provided to the sides of the transparent caps 124A and 124B in the casing 120, respectively.

As shown in FIG. 2, the capsule endoscope 100 includes a capsule controller 102; the imaging units 105A and 105B; an imaging unit 104; a wireless transmitter 106; a battery 108; and a permanent magnet 110 that are provided in the casing 120.

The imaging unit 105A includes a CCD array 105a that is a photoelectric transducer that stores electric charges corresponding to the amount of incident light, and at least one LED 105b that illuminates the interior of the subject. The imaging unit 105A is mounted on a mounting surface of a substrate 104A, which is arranged on the side of the cap 124A in the casing 120, such that the mounting surface faces the outside of the casing 120 through the cap 124A. Specifically, the CCD array 105a of the imaging unit 105A is mounted on the mounting surface of the substrate 104A such that its receiving surface faces the outside of the casing 120 through the cap 124A. Similarly, each LED 105b of the imaging unit 105A is mounted on a mounting surface of the substrate 104A such that the direction in which light is emitted extends toward the outside of the casing 120 through the cap 124A. Because of this arrangement, a view angle VA1 of the imaging unit 105A is in the direction extending through the cap 124A (see FIG. 2).

The imaging unit 105B includes the CCD array 105a and at least one LED 105b as the imaging unit 105A does. The imaging unit 105B is mounted on the mounting surface of a substrate 104B, which is arranged in the casing 120, such that the mounting surface faces the outside of the casing 120 through the cap 124B provided on the opposite side of the cap 124A. Specifically, the CCD array 105a of the imaging unit 105B is mounted on a mounting surface of the substrate 104B such that its receiving surface faces the outside of the casing 120 through the cap 124B. Similarly, each LED 105b of the imaging unit 105B is mounted on the mounting surface of the substrate 104B such that the direction in which light is emitted extends toward the outside of the casing 120 through the cap 124B. Because of this arrangement, a view angle VA2 of the imaging unit 105B is in the direction extending through the cap 124B that is opposite to that of the view angle VA1 of the imaging unit 105A (see FIG. 2).

Instead of the CCD array 105a, various photoelectric transducers, such as a complementary metal oxide semiconductor (CMOS) sensor array, can be used. Instead of the LED 105b, various light emitting devices can be used.

The imaging unit 104 regularly reads image signals that are generated by the imaging units 105A and 105B alternately or simultaneously, and performs processes including an analog to digital (A/D) converting process to generate image data. The imaging unit 104 inputs the image data to the wireless transmitter 106 directly or through the capsule controller 102. The imaging unit 104 adds, to the image data, information for identifying the imaging unit 105A or 105B from which an image signal is read and information about the time at which the image signal is read or the image data is generated from the image signal.

The wireless transmitter 106 includes an antenna (not shown). The wireless transmitter 106 converts the image data, which is input from the imaging unit 104, to a wireless signal and transmits the wireless signal to a receiving apparatus 300, which is described below, outside the capsule endoscope 100. The wireless transmitter 106 may receive a wireless signal that is transmitted from the receiving apparatus 300 and input the wireless signal to the capsule controller 102.

The capsule controller 102 includes a memory (storage) that stores therein programs and parameters for performing various operations. The capsule controller 102 reads the programs and parameters appropriately from the memory and performs the various operations to control each unit of the capsule endoscope 100. Accordingly, the capsule controller 102 regularly acquires image data and transmits the image data to the receiving apparatus 300. If a configuration is adopted in which a control command is input to the capsule controller 102 from the receiving apparatus 300 through the wireless transmitter 106, the capsule controller 102 controls each unit of the capsule endoscope 100 based on the control command.

The battery 108 supplies electric power to each unit of the capsule endoscope 100. The battery 108 can be configured of, for example, a primary battery, such as a button battery, or a secondary battery.

Figure 3:
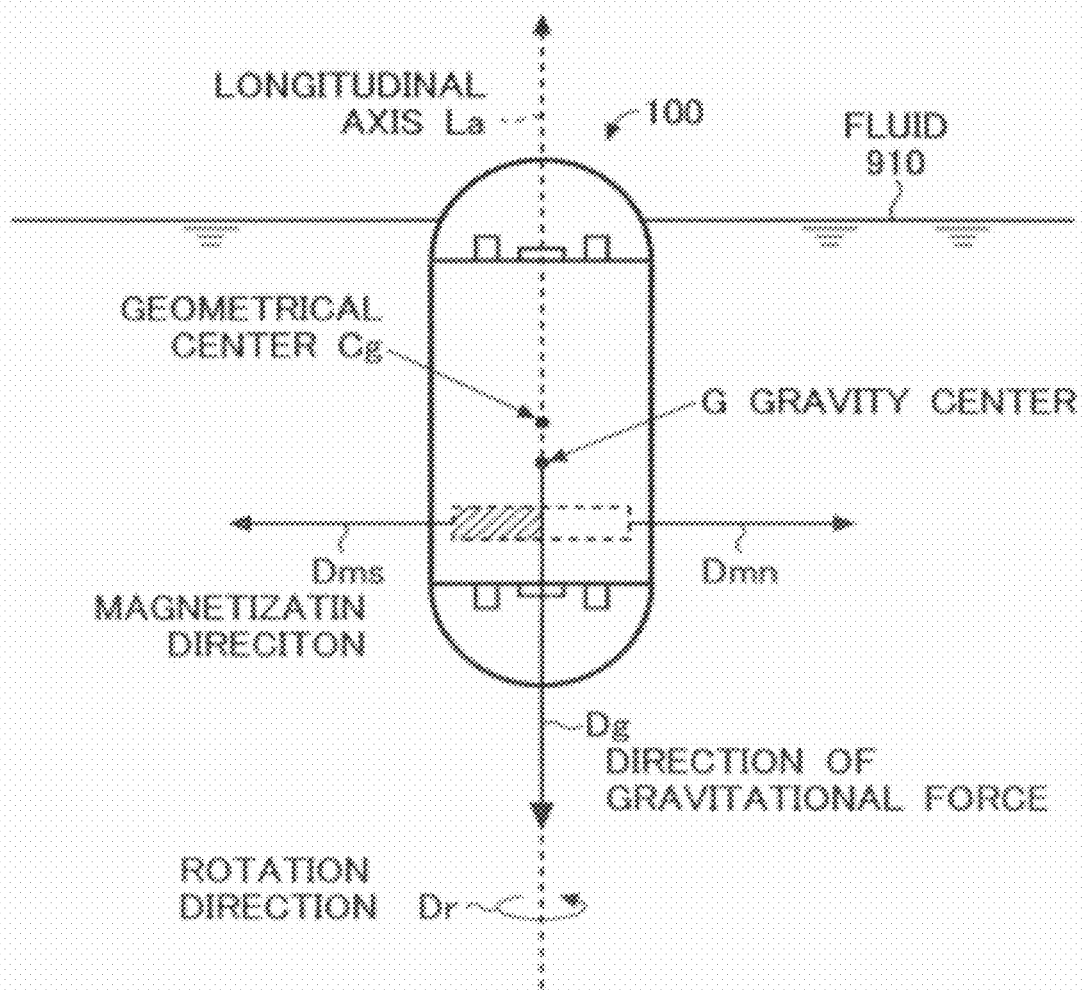
FIG. 3 is a schematic diagram for explaining the state where the capsule endoscope according to the first embodiment of the present invention floats in a liquid that is introduced into a subject.

The permanent magnet 110 is fixed, for example, in the cylindrical container 122 of the casing 120. The case where the capsule endoscope 100 floats in a liquid 910 that is introduced into the subject is explained with reference to FIG. 3. FIG. 3 is a schematic diagram for explaining the case where the capsule endoscope 100 floats in the liquid 910 that is introduced into the subject. In the case represented by FIG. 3, a magnetic field for controlling the posture (in the direction of a longitudinal-axis La) of the capsule endoscope 100 is not applied to the permanent magnet 110.

The specific gravity of the capsule endoscope 100 of the first embodiment to the liquid 910 is smaller than 1. Therefore, as shown in FIG. 3, the capsule endoscope 100 floats in the liquid 910. The gravity center G of the capsule endoscope 100 is previously shifted from a geometrical center Cg of the capsule endoscope 100 along the longitudinal axis La of the capsule endoscope 100. Thus, the longitudinal axis La of the capsule endoscope 100 is parallel to the vertical direction (i.e., the direction Dg of the gravitational force). In other words, the capsule endoscope 100 can be made to float while being vertical in the liquid 910. The longitudinal axis La of the capsule endoscope 100 is a central axis of the capsule endoscope 100 in its longitudinal direction. The imaging units 105A and 105B are arranged such that, for example, the optical central axes of the respective CCD arrays 105a overlap the longitudinal axis La and the image-pickup directions of the imaging units 105A and 105B extend in opposite directions.

The permanent magnet 110 is fixed in the casing 120 such that magnetization directions Dmn and Dms are oblique to the longitudinal axis La of the capsule endoscope 100 (for example, perpendicular). The magnetization direction Dmn is the magnetization direction of the north pole of the permanent magnet 110, and the magnetization direction Dms is the magnetization direction of the south pole of the permanent magnet 110. By fixing the permanent magnet 110 such that the magnetization directions Dms and Dms are oblique to the longitudinal axis La, the posture of the capsule endoscope 100 in a rotation direction Dr (or the radial direction perpendicular to the long axis La) on the longitudinal axis La can be controlled with a magnetic field that is externally applied.

The angle of the capsule endoscope 100 to the direction Dg of the gravitational force can be controlled by externally applying a magnetic field to the permanent magnet 110 of the capsule endoscope 100. In other words, by applying a magnetic field having magnetic field lines with an angle to the horizontal plane to the permanent magnet 110, the capsule endoscope 100 can be oblique to the direction Dg of the gravitational force such that the magnetization directions Dms and Dms of the permanent magnet 110 are approximately parallel to the magnetic field lines.

Figure 4:
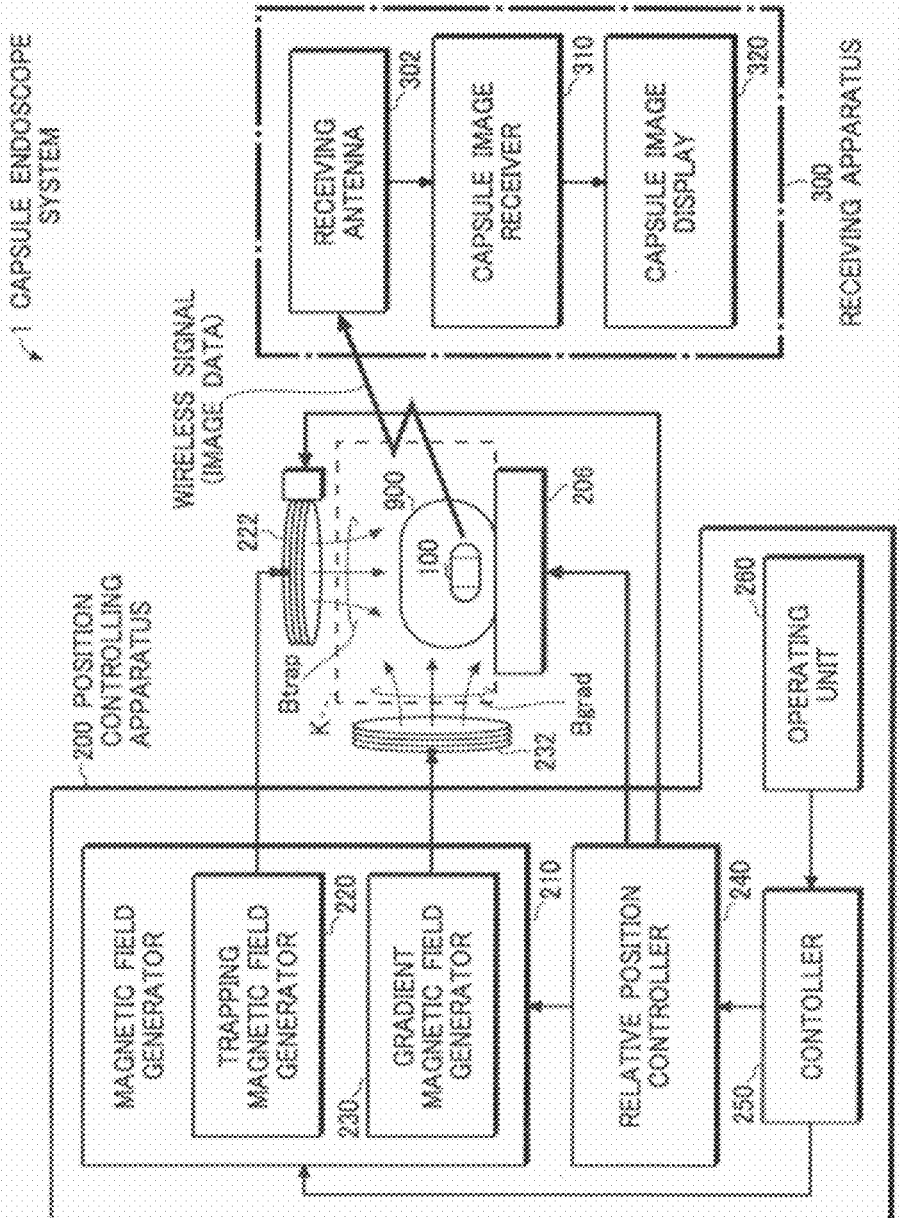
FIG. 4 is a block diagram of a configuration of the capsule endoscope system according to the first embodiment of the present invention.

The capsule endoscope system 1 using the capsule endoscope 100 is explained in detail below with reference to the accompanying drawings. FIG. 4 is a block diagram of a configuration of the capsule endoscope system 1 according to the first embodiment. FIG. 5 is a perspective view of a schematic configuration example of a position controlling apparatus 200 of the capsule endoscope system 1.

As shown in FIG. 4, the capsule endoscope system 1 includes the receiving apparatus 300 that receives image data that is transmitted as a wireless signal from the capsule endoscope 100; and the position controlling apparatus 200 that forms, in a detecting space K, a magnetic field (trapping magnetic field) Btrap and a gradient magnetic field Bgrad to be applied to the permanent magnet 110 of the capsule endoscope 100, and that controls the relative position between a subject 900 to which the capsule endoscope 100 is introduced and the central axis of the trapping magnetic field Btrap. In the explanation, the direction vertical to the ground surface is referred to as "Z-axis", the Z-axis on the center of a trapping magnetic field generating coil 222 to be described below is referred to as "central Z-axis Az". The longitudinal direction of a bed 206 to be described below is referred to as "X-axis", and the lateral direction of the bed 206 is referred to as "Y-axis" in the explanation. Therefore, in the explanation, an X-Y plane is the horizontal plane. Furthermore, it is provided that the position controlling apparatus 200 controls the relative position of the bed 206 on which the subject 900 is laid and the central Z-axis Az of the trapping magnetic field generating coil 222.

The receiving apparatus 300 includes a receiving antenna 302 that receives the wireless signal that is transmitted from the capsule endoscope 100; a capsule image receiver 310 to which the image data, which is received as the wireless signal from the capsule endoscope 100, is input and that performs a predetermined process on the image data; and a capsule image display 320 that reproduces the image data on which the capsule image receiver 310 performs the predetermined process. The image data of in-vivo images of the subject 900 that is acquired by the capsule endoscope 100 and transmitted as the wireless signal is input to the capsule image receiver 310 through the receiving antenna 302. After the predetermined process is performed on the image data, the image data is displayed on the capsule image display 320.

The position controlling apparatus 200 includes a magnetic field generator 210 that forms the trapping magnetic field Btrap and the gradient magnetic field Bgrad; a relative position controller 240 that controls the relative position between the bed 206 and the central Z-axis Az of the trapping magnetic field generating coil 222; a controller 250 that controls the magnetic field generator 210 and the relative position controller 240; and an operating unit 260 through which the user inputs various control commands to the controller 250.

The relative position controller 240 is connected to at least one of the bed 206, on which the subject 900 to be examined is laid, and/or to the trapping magnetic field generating coil 222. By moving the bed 206 and/or the trapping magnetic field generating coil 222 horizontally, the relative position between the bed 206 and the central Z-axis Az of the trapping magnetic field generating coil 222 is changed. The space above the bed 206 is the detecting space K to which the subject 900 is introduced. The bed 206 and the relative position controller 240 that includes a driving mechanism (not shown) that drives the bed 206 and/or a driving mechanism (not shown) that drives the trapping magnetic field generating coil 222 function as a relative position controlling mechanism that changes the relative position between the central Z-axis (a predetermined axis) and the subject 900. The detecting space K does not move along with the movement of the bed 206. Alternatively, the detecting space K may move along with the movement of the bed 206.

The magnetic field generator 210 includes a trapping magnetic field generator 220 that generates the trapping magnetic field Btrap; and a gradient magnetic field generator 230 that generates the gradient magnetic field Bgrad. The trapping magnetic field generator 220 is electrically connected to the trapping magnetic field generating coil 222 that is provided near the detecting space K. The trapping magnetic field generating coil 222 is provided such that the central Z-axis Az of the trapping magnetic field generating coil 222 is perpendicular to the surface of the bed 206 on which the subject is laid. A gradient magnetic field generating coil 232 that is provided near the detecting space K is electrically connected to the gradient magnetic field generator 230.

The magnetic field generator 210 that includes the trapping magnetic field generator 220, the trapping magnetic field generating coil 222 that is connected to the trapping magnetic field generator 220, the gradient magnetic field generator 230, and the gradient magnetic field generating coil 232 that is connected to the gradient magnetic field generator 230 serves as a magnetic field generating mechanism that forms, in the detecting space K in which the subject 900 is laid, a magnetic field that includes at least one of the trapping magnetic field component (i.e., the trapping magnetic field Btrap) that attracts the permanent magnet 110 to the central Z-axis Az and the gradient magnetic field component (i.e., the gradient magnetic field Bgrad) that attracts the permanent magnet 110 in the direction same as or opposite to that in which the relative position is changed.

For example, the trapping magnetic field generator 220 generates a current signal having a specific amplitude (hereinafter, "trapping signal") and inputs the trapping signal to the trapping magnetic field generating coil 222 under the control of the controller 250. Accordingly, the trapping magnetic field Btrap is formed in the detecting space K to hold the capsule endoscope 100 that includes the permanent magnet 110 in a target position (a position on the central Z-axis Az of the trapping magnetic field generating coil 222). The trapping magnetic field generator 220 generates the trapping signal having a signal pulse shape that causes the trapping magnetic field generating coil 222 to generate the trapping magnetic field Btrap with the peak of intensity on the central Z-axis Az.

The gradient magnetic field generator 230 generates a current signal (hereinafter, "gradient signal") having a specific amplitude and inputs the gradient signal to the gradient magnetic field generating coil 232 under the control of the controller 250. Accordingly, the gradient magnetic field Bgrad is formed in the detecting space K to attract the capsule endoscope 100 that includes the permanent magnet 110 in a target direction (for example, the direction in which the bed 206 is accelerated or the direction opposite to the direction in which the bed 206 is accelerated). As described below, the gradient magnetic field generating coil 232 according to the first embodiment includes at least a pair of coils (i.e., an X-axis gradient coil 232x-1/232y-1 and 232x-2/232y-2; see FIG. 18) that can form a magnetic field that includes a parallel component (an X-axis component or a Y-axis component) in the detecting space K. The gradient magnetic field generator 230 adjusts the amplitudes of gradient signals to be input to the pairs of coils, i.e., adjusts the balance of the intensity of signals to be input respectively to the coils, so that the gradient magnetic field generating coil 232 is caused to form the gradient magnetic field Bgrad whose distribution of intensity of magnetic field is gradient in the detecting space K (particularly, near the central Z-axis Az).

As shown in FIG. 5, the position controlling apparatus 200 includes a housing 202 that stores therein at least a part of the bed 206. Windows 204A and 204B are formed in the housing 202 to secure the exit from which the subject 900 is transferred to the bed 206 and the movability of the bed 206. The area above the bed 206 in the housing 202 is set as the detecting space K in which the subject 900 is laid. A part of the bed 206 may protrude from the housing 202 to the outside from both of or one of the windows 204A and 204B.

The relative position controller 240 and the magnetic field generator 210 are provided, for example, under the bed 206 and in the housing 202. The controller 250 and the operating unit 260 are, for example, a personal computer 270 that is arranged outside the housing 202. The personal computer 270, the relative position controller 240, and the magnetic field generator 210 are connected through, for example, communication cables such that they can communicate with one another. It is obvious that various modifications may be made alternatively. For example, the relative position controller 240, the magnetic field generator 210, the controller 250, and the operating unit 260 may be provided in the housing 202.

Figure 6A:
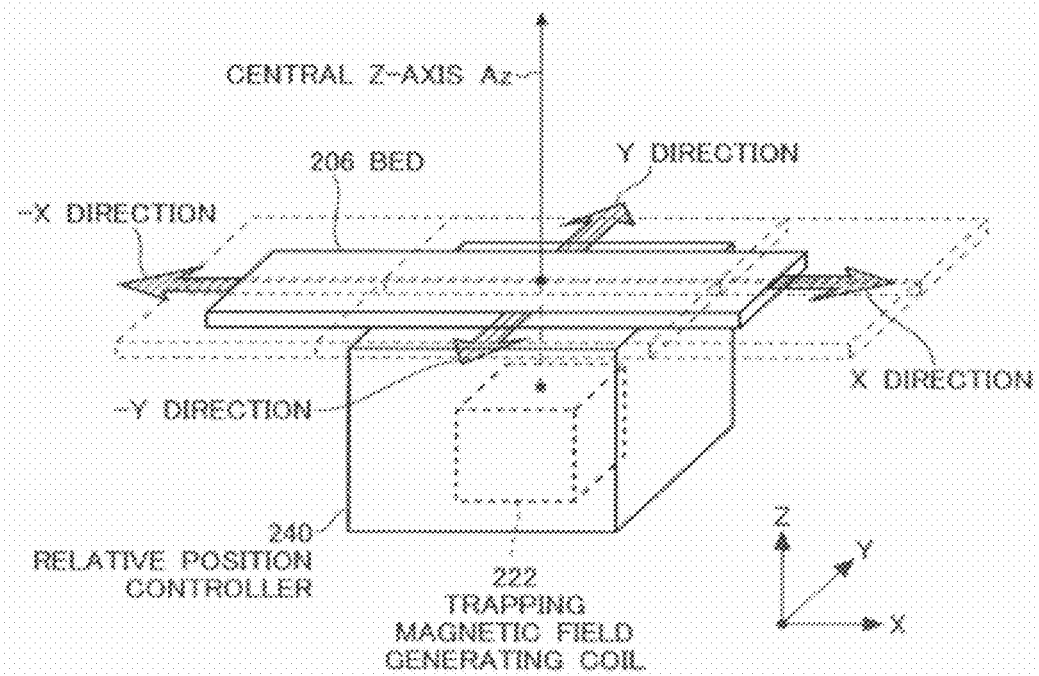
FIG. 6A is a perspective view for explaining the positional relationship between a bed and a central Z-axis of a trapping magnetic field generating coil according to the first embodiment of the present invention in the case where a relative position controlling apparatus is configured to move the bed on the horizontal plane (X-Y plane)
Figure 6B:
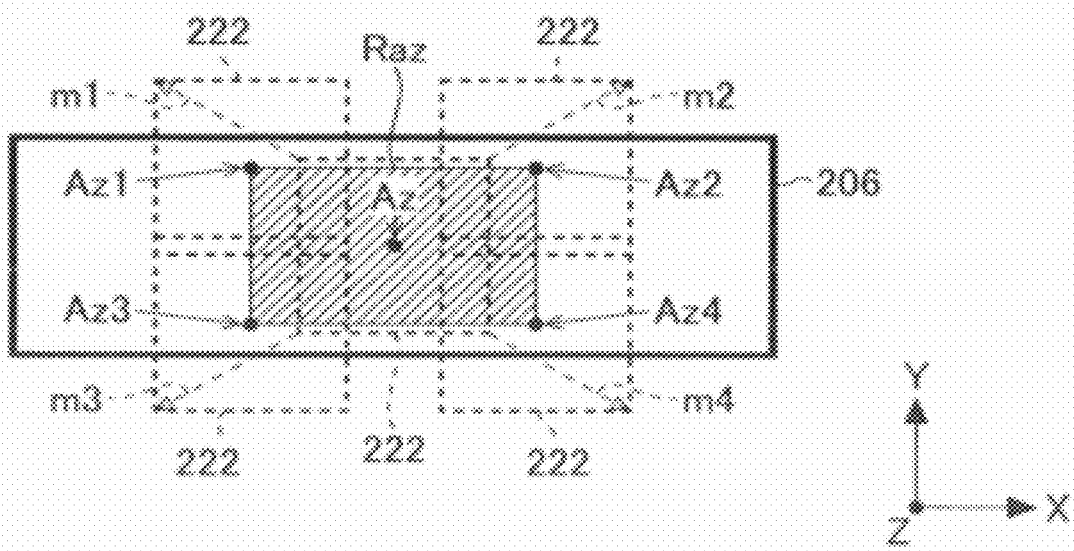
FIG. 6B is a top view for explaining the positional relationship between the bed and the central Z-axis of the trapping magnetic field generating coil, which are shown in FIG. 6A.

The positional relationship between the bed 206 (specifically, the subject 900 on the bed 206) and the trapping magnetic field generating coil 222 (specifically, the central Z-axis Az) is explained in detail below with reference to FIG. 6A. FIG. 6A is a perspective view for explaining the positional relationship between the bed 206 and the central Z-axis Az of the trapping magnetic field generating coil 222 in the case where the relative position controller 240 is configured to move the bed 206 on the horizontal plane (X-Y plane). In this case, the trapping magnetic field generating coil 222 is fixed to the housing 202. FIG. 6B is a top view for explaining the positional relationship between the bed 206 and the central Z-axis Az of the trapping magnetic field generating coil 222 that are shown in FIG. 6A. The relative position controller 240 is not shown in FIG. 6B to simplify the drawing. For clear explanation, FIG. 6B represents the case where the bed 206 is fixed and the position of the trapping magnetic field generating coil 222 with respect to the bed 206 is changed in the horizontal direction.

As shown in FIG. 6A, the trapping magnetic field generating coil 222 is fixed under the bed 206. The bed 206 is movable horizontally in the X-direction or a −X-direction and/or the Y-direction or a −Y-direction under the control of the relative position controller 240. Therefore, as shown in FIG. 6B, the central Z-axis Az of the trapping magnetic field generating coil 222 with respect to the bed 206 can be moved within an area Raz formed by connecting points Az1 to Az4. The point Az1 is the position of the central Z-axis Az that is achieved by moving the trapping magnetic field generating coil 222 in a reference position in the direction represented by the arrow m1 shown in FIG. 6B. The point Az2 is the position of the central Z-axis Az that is achieved by moving the trapping magnetic field generating coil 222 in the reference position in the direction represented by the arrow m2 shown in FIG. 6B. The point Az3 is the position of the central Z-axis Az that is achieved by moving the trapping magnetic field generating coil 222 in the reference position in the direction represented by the arrow m3 shown in FIG. 6B. The point Az4 is the position of the central Z-axis Az that is achieved by moving the trapping magnetic field generating coil 222 in the reference position in the direction represented by the arrow m4 shown in FIG. 6B.

Figure 7A:
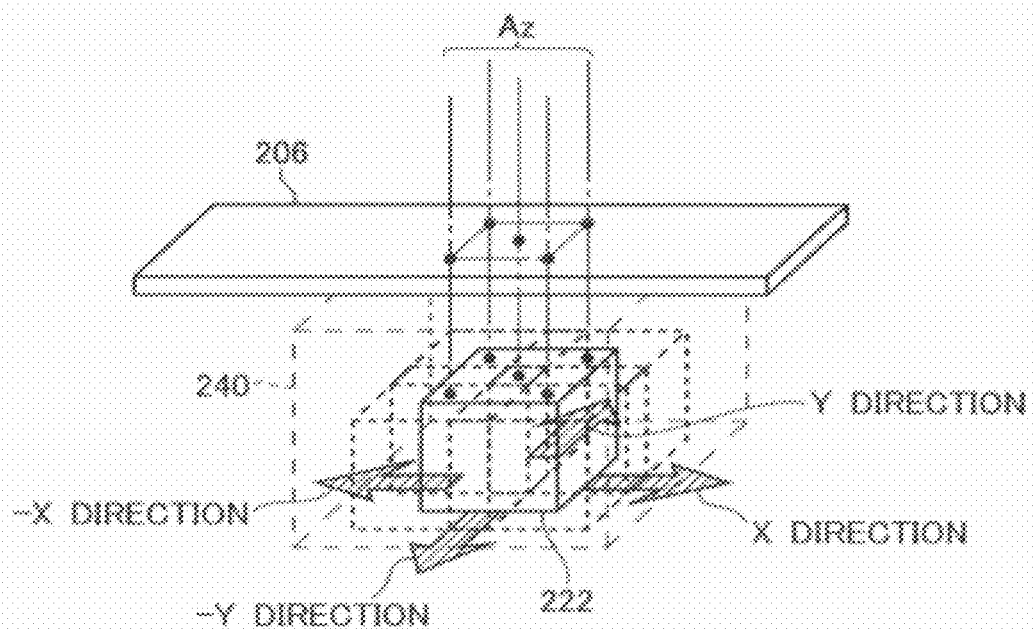
FIG. 7A is a perspective view for explaining the positional relationship between the bed and the central Z-axis of the trapping magnetic field generating coil in the case where the relative position controller is configured to move the trapping magnetic field generating coil on the horizontal plane (X-Y plane) in the first embodiment.

The relative position controller 240 may be configured to control the relative position between the bed 206 and the central Z-axis Az of the trapping magnetic field generating coil 222 by moving the trapping magnetic field generating coil 222 on the horizontal plane (X-Y plane). FIG. 7A is a perspective view for explaining the positional relationship between the bed 206 and the central Z-axis Az of the trapping magnetic field generating coil 222 in the case where the relative position controller 240 is configured to move the trapping magnetic field generating coil 222 on the horizontal plane (X-Y plane).

Figure 7B:
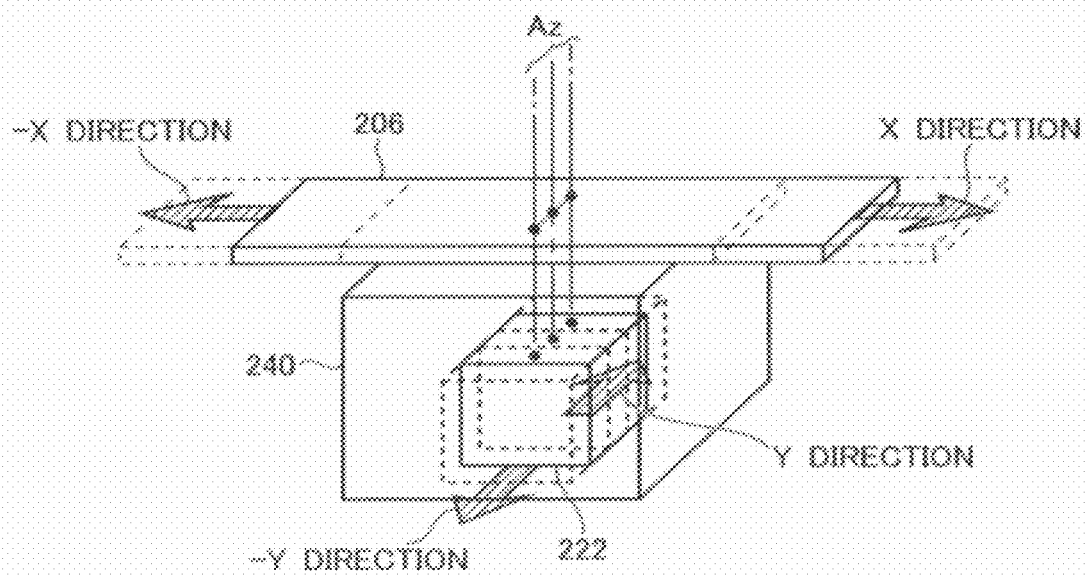
FIG. 7B is a perspective view for explaining the positional relationship between the bed and the central Z-axis of the trapping magnetic field generating coil in the case where the relative position controller is configured to move the bed in the X/−X direction and move the magnetic field generating coil in the Y/−Y direction.

The relative position controller 240 may be configured to control the relative position between the bed 206 and the central Z-axis Az of the trapping magnetic field generating coil 222 by moving the bed 206 in the X/−X direction (or Y/−Y direction) and moving the trapping magnetic field generating coil 222 in the Y/−Y direction (or X/−X direction). FIG. 7B is a perspective view for explaining the positional relationship between the bed 206 and the central Z-axis Az of the trapping magnetic field generating coil 222 in the case where the relative position controller 240 is configured to move the bed 206 in the X/−X direction and move the trapping magnetic field generating coil 222 in the Y/−Y direction.

An example of the trapping magnetic field generating coil 222 according to the first embodiment is explained in detail below. The trapping magnetic field generating coil 222 according to the first embodiment includes a plurality of coils that are symmetrically arranged with respect to the central Z-axis Az. Specifically, the trapping magnetic field generating coil 222 includes one Z-axis trapping coil or a pair of Z-axis trapping coils that generates a magnetic field in the direction of the central Z-axis Az; one X-axis trapping coil or a pair of X-axis trapping coils that generates a magnetic field in the direction of the axis (X-axis Ax) perpendicular to the central Z-axis Az; and one Y-axis trapping coil or a pair of Y-axis trapping coils that generates a magnetic field in the direction of the axis (Y-axis Ay) perpendicular to the central Z-axis Az and the X-axis Ax. The Z-axis trapping coil, the X-axis trapping coil, and the Y-axis trapping coil form a trapping magnetic field Btrap having the peak of intensity near the intersection with the central Z-axis Az on an arbitrary X-Y plane.

Figure 8:
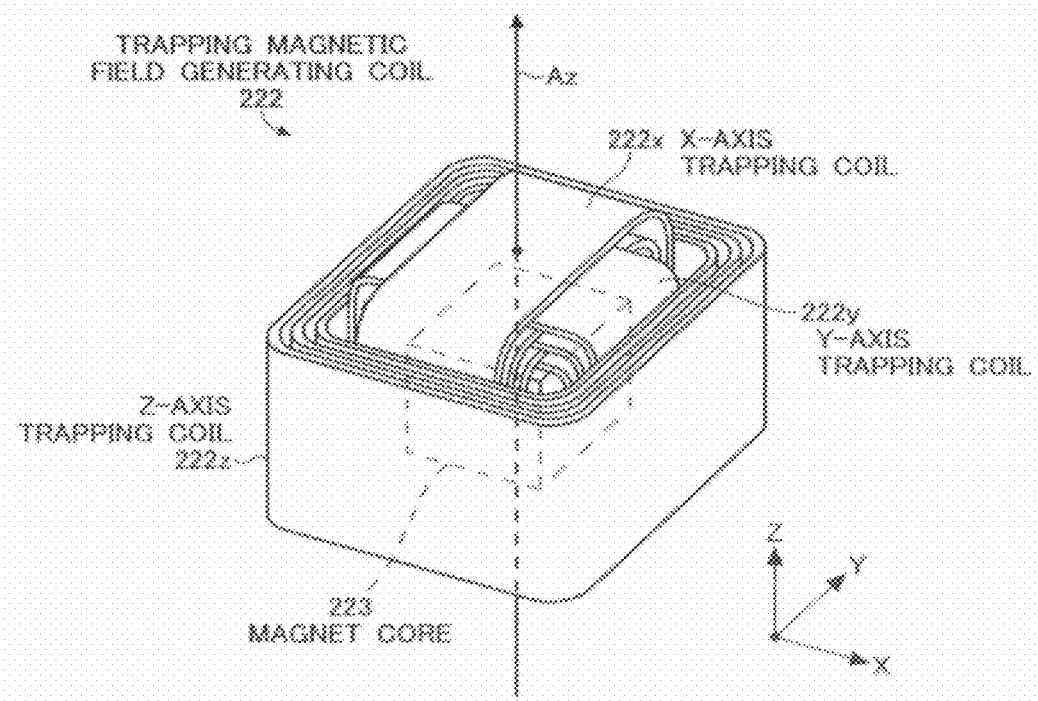
FIG. 8 is a perspective view of an example of the trapping magnetic field generating coil according to the first embodiment of the present invention.
Figure 9B:
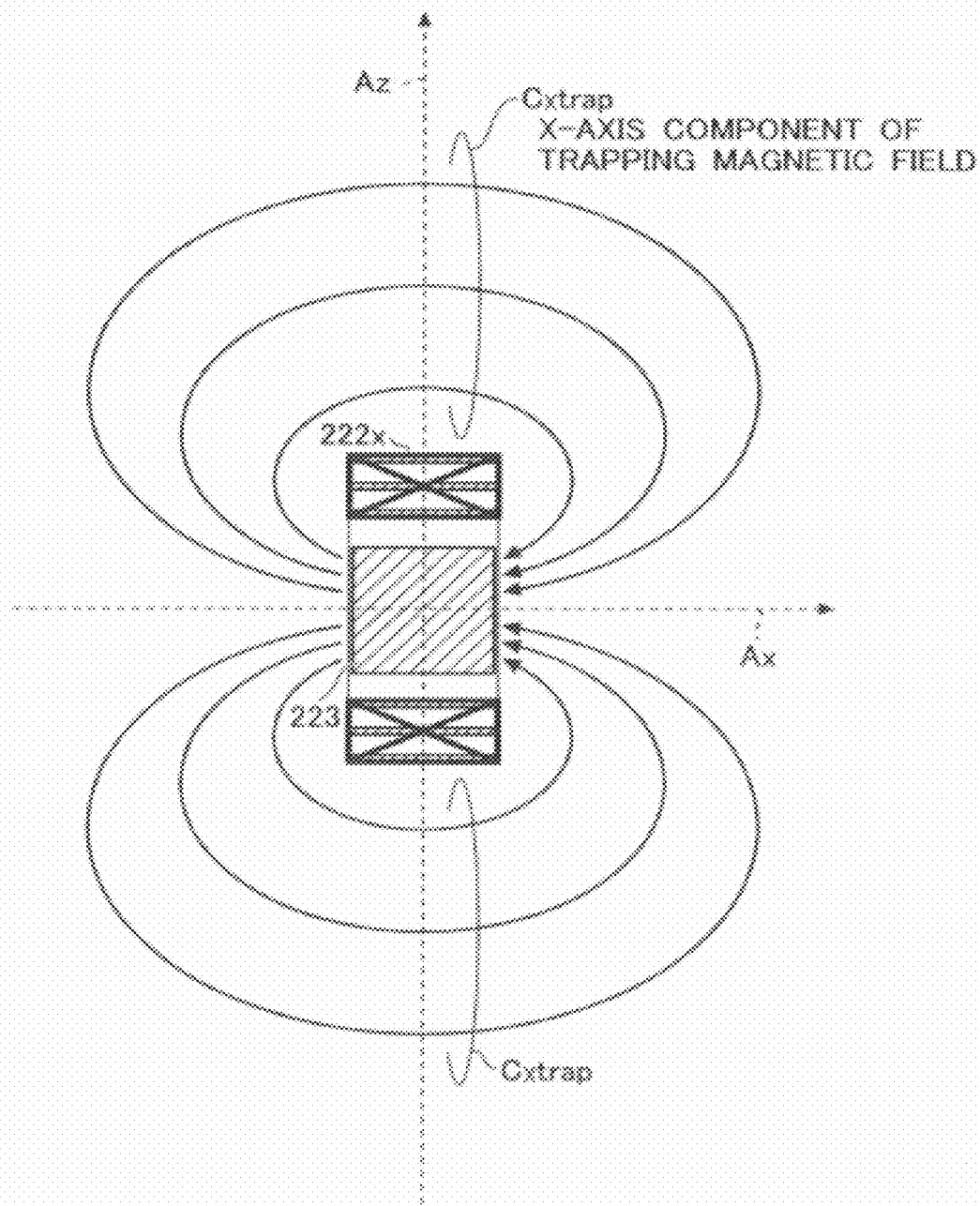
FIG. 9B is a schematic diagram of an X-axis component of the trapping magnetic field that is formed by the X-axis trapping coil shown in FIG. 9A.
Figure 11A:
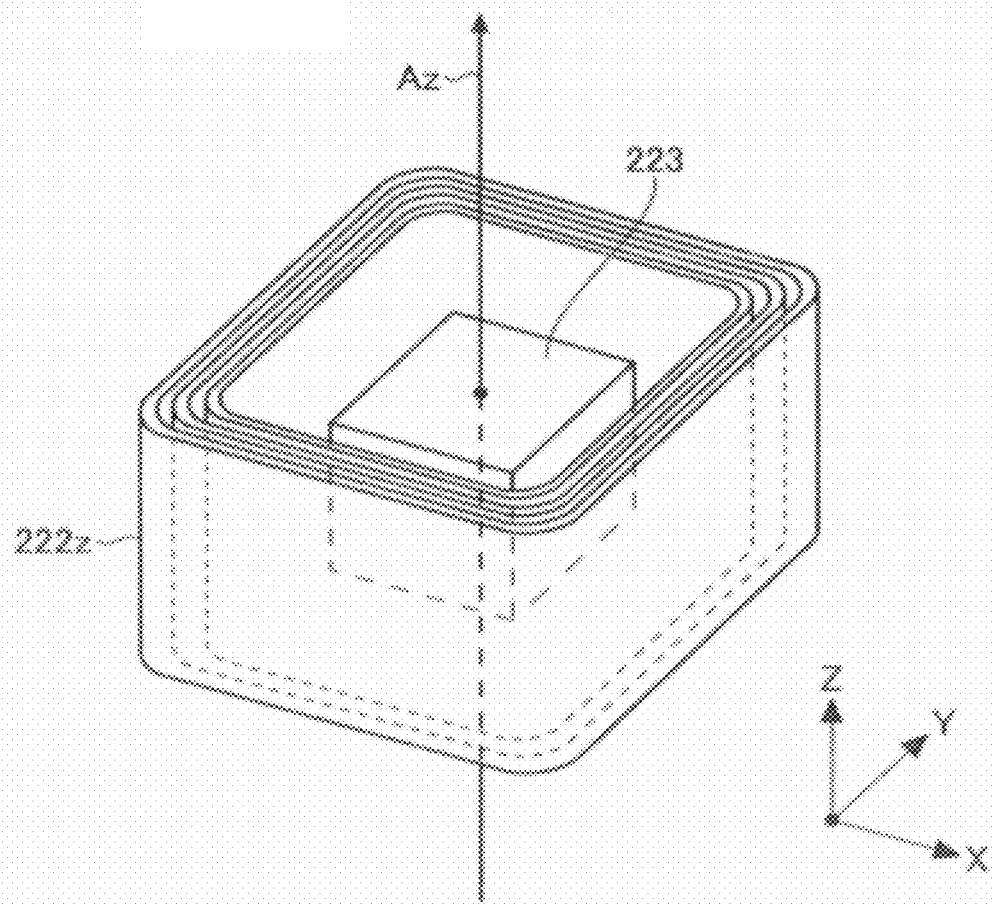
FIG. 11A is a perspective view of an example of a Z-axis trapping coil of the trapping magnetic field generating coil shown in FIG. 8.

A specific example of the trapping magnetic field generating coil 222 is explained in detail below with reference to the accompanying drawings. FIG. 8 is a perspective view of an example of the trapping magnetic field generating coil 222. FIG. 9A is a perspective view of an example of an X-axis trapping coil 222x of the trapping magnetic field generating coil 222. FIG. 9B is a schematic diagram of an X-axis component $C_X$trap of the trapping magnetic field that is formed by the X-axis trapping coil 222x of the trapping magnetic field generating coil 222. FIG. 10A is a perspective view of an example of a Y-axis trapping coil 222y of the trapping magnetic field generating coil 222. FIG. 10B is a schematic diagram of a Y-axis component $C_Y$trap of the trapping magnetic field that is formed by the Y-axis trapping magnetic field that is formed by the Y-axis trapping coil 222y. FIG. 11A is a perspective view of an example of a Y-axis trapping coil 222z of the trapping magnetic field generating coil 222. FIG. 11B is a schematic diagram of a Z-axis component $C_Z$trap of the trapping magnetic field that is formed by the Z-axis trapping coil 222z.

As shown in FIG. 8, the trapping magnetic field generating coil 222 includes the X-axis trapping coil 222x whose central axis extends in the X-axis direction; the Y-axis trapping coil 222y whose central axis extends in the Y-axis direction; and the Z-axis trapping coil 222z whose central axis extends in the Z-axis direction (the central Z-axis Az). The coils are combined such that the centers of the respective coils coincide. For example, a magnet core 223 is provided at the center of the X-axis trapping coil 222x, the Y-axis trapping coil 222y, and the Z-axis trapping coil 222z.

As shown in FIG. 9A, the number of coil turns of the X-axis trapping coil 222x is at least one, and the magnet core 223 is arranged at the center of the X-axis trapping coil 222x. Thus, as shown in FIG. 9B, the magnetic field lines of the X-axis component $C_X$trap of the trapping magnetic field that is generated by the X-axis trapping coil 222x form an 8-like shape on the plane including the central X-axis Ax of the X-axis trapping coil 222x.

As shown in FIG. 10A, the number of coil turns of the Y-axis trapping coil 222y is at least one, and the magnet core 223 is arranged at the center of the Y-axis trapping coil 222y. Thus, as shown in FIG. 10B, the magnetic field lines of the Y-axis component $C_Y$trap of the trapping magnetic field that is generated by the Y-axis trapping coil 222y form an 8-like shape of on the plane including the central Y-axis Ay of the Y-axis trapping coil 222y.

As shown in FIG. 11A, the number of coil turns of the Z-axis trapping coil 222z is at least one, and the magnet core 223 is arranged at the center of the Z-axis trapping coil 222z. Thus, as shown in FIG. 11B, the magnetic field lines of the Z-axis component $C_Z$trap of the trapping magnetic field that is generated by the Z-axis trapping coil 222z form an 8-like shape on the plane including the central Z-axis Az of the Z-axis trapping coil 222z.

As shown in FIG. 8, the X-axis trapping coil 222x and the Y-axis trapping coil 222y are combined such that each coil turn is alternate. The Z-axis trapping coil 222z is arranged such that it surrounds the assembly of the X-axis trapping coil 222x and the Y-axis trapping coil 222y on the X-Y plane. Alternatively, various modifications may be made as long as the trapping magnetic field Btrap having the peak of intensity on the central Z-axis Az can be formed in the detecting space K.

Figure 12:
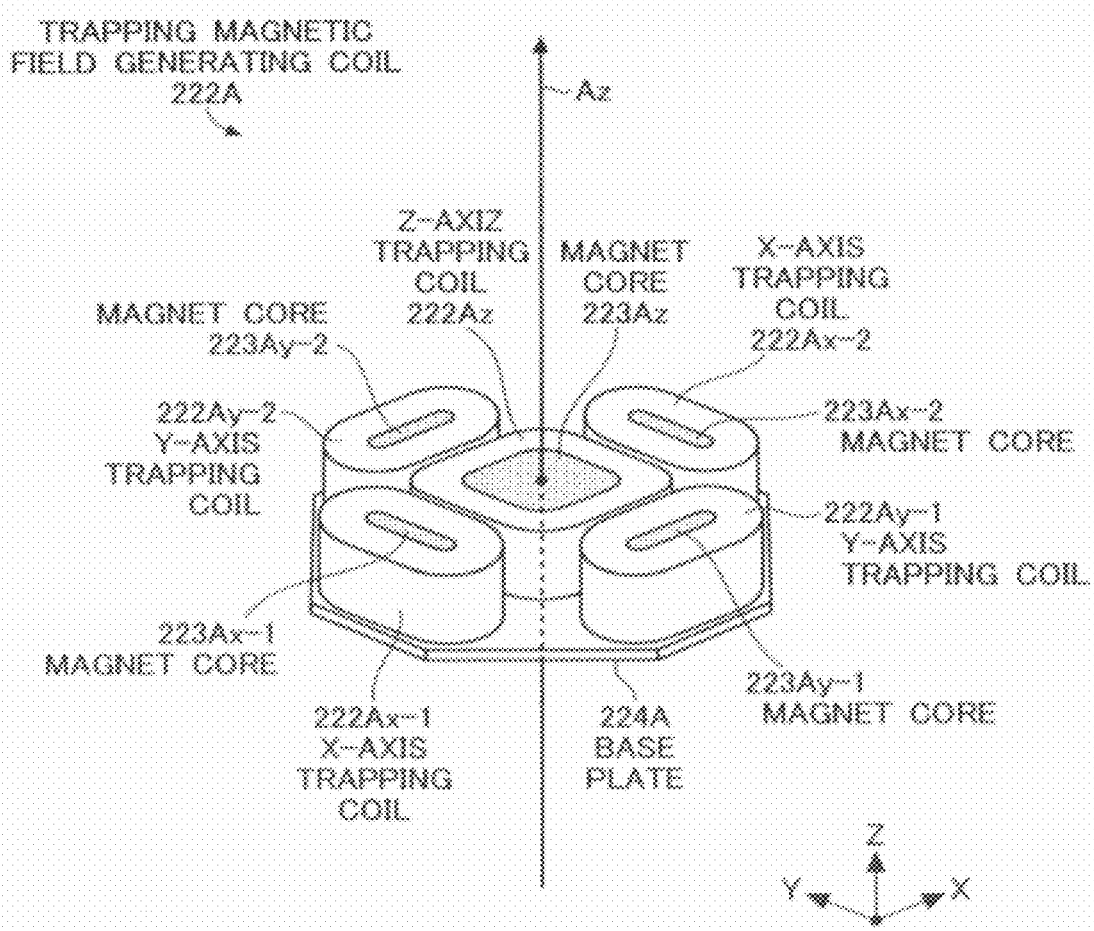
FIG. 12 is a perspective view of an example of a trapping magnetic field generating coil of Modification 1-1 of the first embodiment of the present invention.
Figure 13:
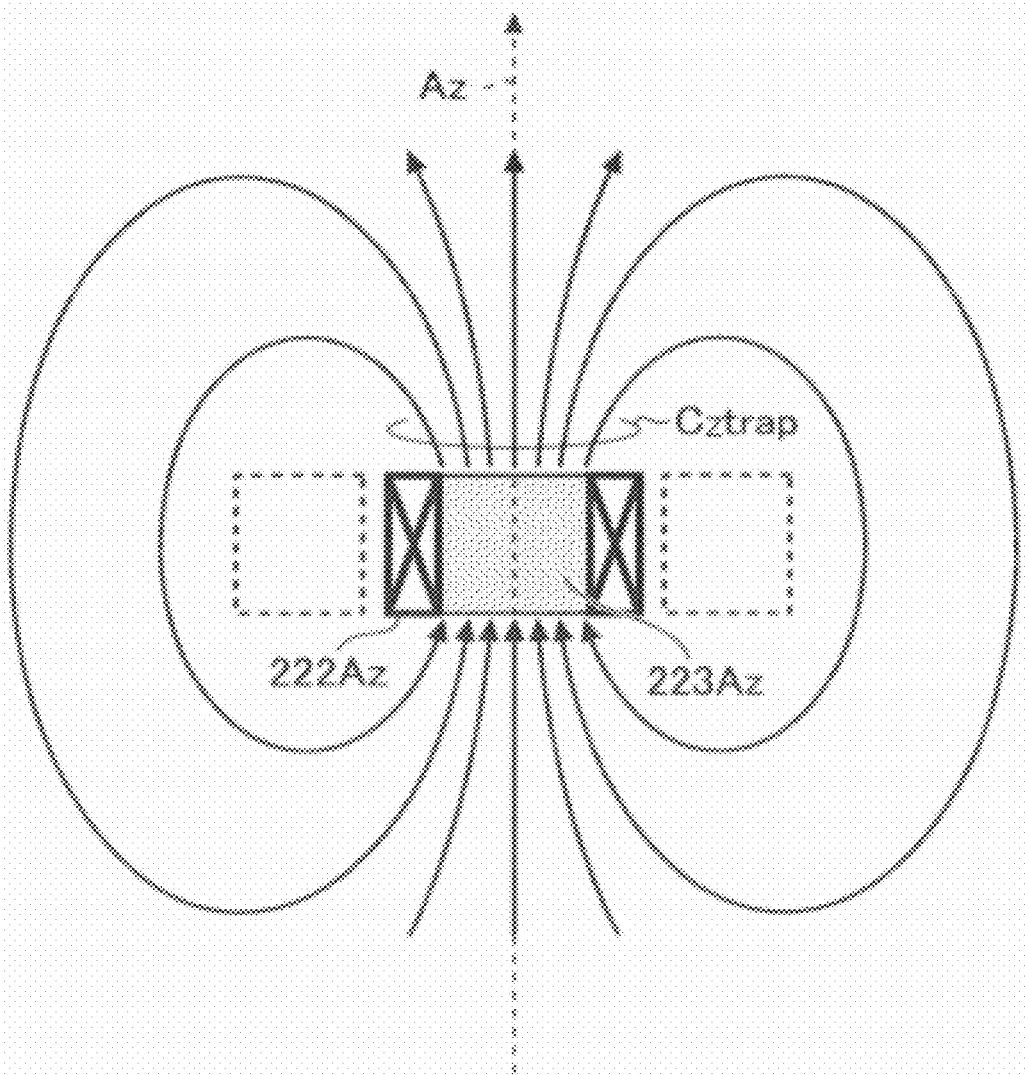
FIG. 13 is a schematic diagram of a Z-axis component of a trapping magnetic field that is formed by a Z-axis trapping coil of the trapping magnetic field generating coil shown in FIG. 12.
Figure 14:
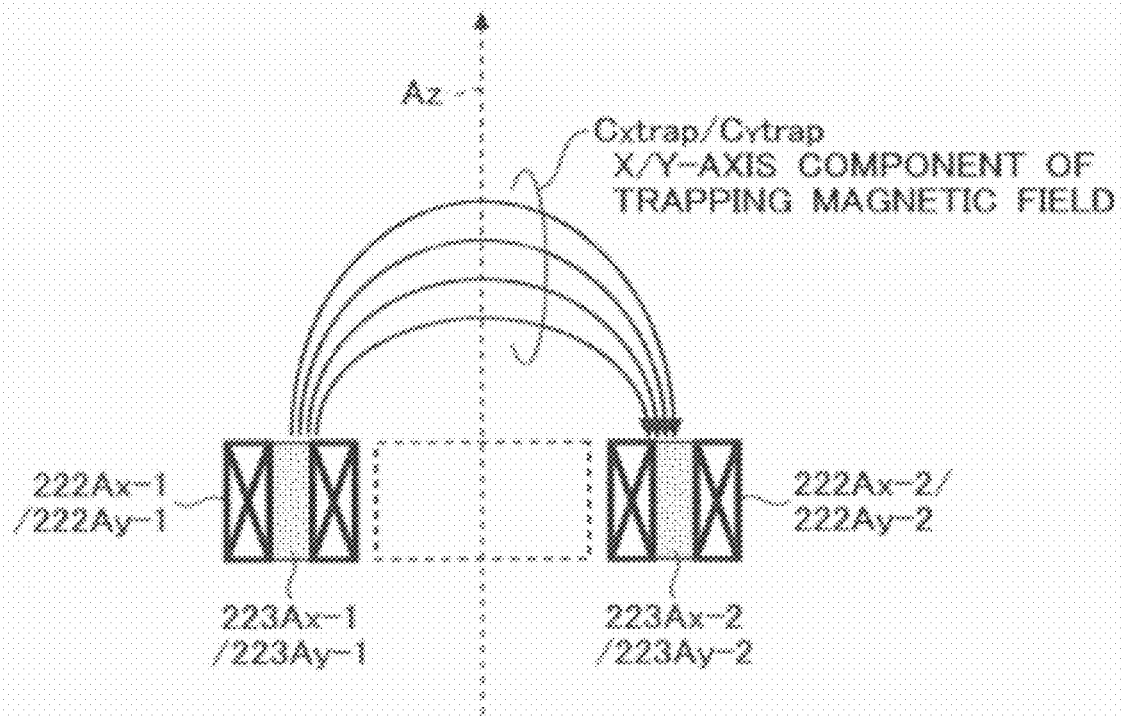
FIG. 14 is a schematic diagram of an X/Y-axis component of a trapping magnetic field that is formed by an X/Y-axis trapping coil of the trapping magnetic field generating coil shown in FIG. 12.

For example, a trapping magnetic field generating coil 222A shown in FIG. 12 may be used as the source of the trapping magnetic field Btrap. FIG. 12 is a perspective view of an example of the trapping magnetic field generating coil 222A of Modification 1-1 of the first embodiment. FIG. 13 is a schematic diagram of a Z-axis component $C_Z$trap of a trapping magnetic field that is formed by a Z-axis trapping coil 222Az of the trapping magnetic field generating coil 222A. FIG. 14 is a schematic diagram of an X/Y-axis component $C_X$trap/$C_Y$trap of a trapping magnetic field that is formed by an X/Y-axis trapping coil 222Ax-1/222Ay-1 and 222Ax-2/222Ay-2 of the trapping magnetic field generating coil 222A.

As shown in FIG. 12, the trapping magnetic field generating coil 222A includes the Z-axis trapping coil 222Az, X-axis trapping coils 222Ax-1 and 222Ax-2 in a pair, and Y-axis trapping coils 222Ay-1 and 222Ay-2 in a pair that are mounted on a base plate 224A. The trapping magnetic field generating coil 222A is provided under the bed 206 in the housing 202 as the trapping magnetic field generating coil 222 is.

The Z-axis trapping coil 222Az is arranged approximately at the center of the base plate 224A. A magnet core 223Az is provided at the center of the Z-axis trapping coil 222Az. Thus, as shown in FIG. 13, the magnetic field lines of the Z-axis component $C_Z$trap of the trapping magnetic field that is generated by the Z-axis trapping coil 222Az form an 8-like shape on the plane including the central Z-axis (which coincides with the central Z-axis Az) of the Z-axis trapping coil 222Az.

The X/Y-axis trapping coils 222Ax-1/222Ay-1 and 222Ax-2/222Ay-2 are arranged in the position where they sandwich the Z-axis trapping coil 222Az on the base plate 224A. At the center of the X/Y-axis trapping coils 222Ax-1/222Ay-1 and 222Ax-2/222Ay-2, magnet cores 223Ax-1/223Ay-1 and 223Ax-2/223Ay-2 are provided, respectively. Therefore, as shown in FIG. 14, the magnetic field lines of the X/Y-axis component $C_X$trap/$C_Y$trap of the trapping magnetic field that is generated by the X/Y-axis trapping coils 222Ax-1/222Ay-1 and 222Ax-2/222Ay-2 extend from the X/Y-axis trapping coil 222Ax-1/222Ay-1 to the X/Y-axis trapping coil 222Ax-2/222Ay-2, thereby forming a swelling shape.

Figure 15:
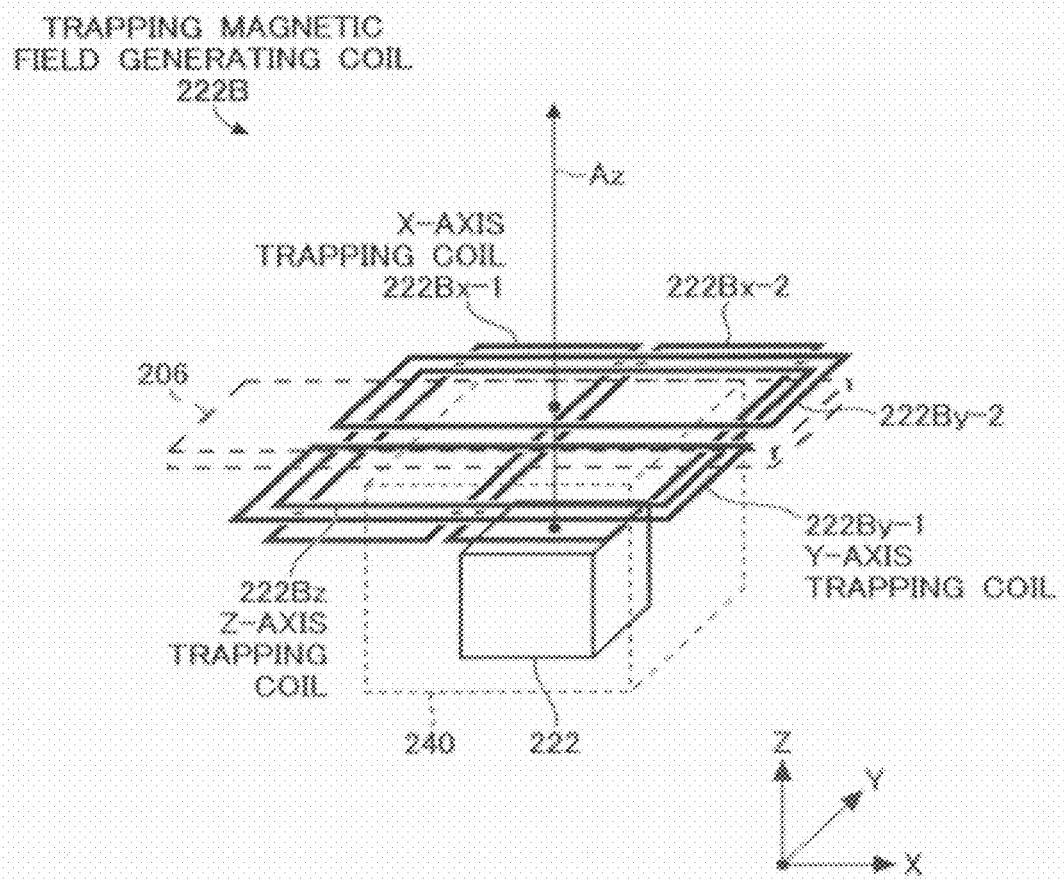
FIG. 15 is a perspective view of an example of a trapping magnetic field generating coil of Modification 1-2 of the first embodiment of the present invention.

The trapping magnetic field generating coil 222A can be modified as shown in FIG. 15. FIG. 15 is a perspective view of an example of a trapping magnetic field generating coil 222B of Modification 1-2 of the first embodiment.

As shown in FIG. 15, the trapping magnetic field generating coil 222B includes X-axis trapping coils 222Bx-1 and 222Bx-2, Y-axis trapping coils 222By-1 and 222By-2, and a Z-axis trapping coil 222Bz that are arranged on a plane approximately parallel to the mounting surface of the bed 206. The X-axis trapping coils 222Bx-1 and 222Bx-2 in a pair are arranged along the X-axis and under the bed 206. Similarly, the Y-axis trapping coils 222By-1 and 222By-2 are arranged along the Y-axis under the bed 206. The Z-axis trapping coil 222Bz is arranged under the bed 206. The X-axis trapping coils 222Bx-1/222Bx-2, the Y-axis trapping coils 222By-1/222By-2, and the Z-axis trapping coil 222Bz may overlap. The lines of the magnetic fields formed by the X-axis trapping coils 222Bx-1 and 222Bx-2, the Y-axis trapping coils 222By-1 and 222By-2, and the Z-axis trapping coil 222Bz are same as those of the trapping magnetic field generating coil 222A of Modification 1-1.

The trapping magnetic field Btrap that is generated by the trapping magnetic field generating coil 222 is explained in detail below with reference to the accompanying drawings. FIG. 16 is a diagram representing the relation between the distribution of intensity of the trapping magnetic field Btrap of the first embodiment and trapping forces Ft1 and Ft2 that are applied to the capsule endoscope 100 because of the trapping magnetic field Btrap. A portion (a) of FIG. 16 illustrates how the trapping forces Ft1 and Ft2 are applied to the capsule endoscope 100 that is floating in the liquid 910. A portion (b) of FIG. 16 illustrates an example of distribution of intensity of the trapping magnetic field Btrap that is formed in the detecting space K by the trapping magnetic field generating coil 222.

As shown in (b) of FIG. 16, the trapping magnetic field generating coil 222 forms the trapping magnetic field Btrap that has the peak of intensity on the central Z-axis Az in the detecting space K. Therefore, as shown in (a) of FIG. 16, the trapping forces Ft1 and Ft2 that attract the permanent magnet 110 in the capsule endoscope 100 to the central Z-axis Az are caused. For example, when the position of the capsule endoscope 100 near the fluid level of the liquid 910 deviates in the −X direction/−Y direction from the central Z-axis Az, the trapping force Ft1 that attracts the capsule endoscope 100 to the central Z-axis Az is applied to the capsule endoscope 100. For example, when the position of the capsule endoscope 100 near the fluid level of the liquid 910 deviates in the X direction/Y direction from the central Z-axis Az, the trapping force Ft2 that attracts the capsule endoscope 100 to the central Z-axis Az is applied to the capsule endoscope 100. As a result, the capsule endoscope 100 can be held near the central Z-axis Az. In the first embodiment, because the specific gravity of the capsule endoscope 100 to the liquid 910 is smaller than 1, the position of the capsule endoscope 100 on the central Z-axis Az is near the fluid level of the liquid 910. The fluid level of the liquid 910 corresponds to the X-Y plane. The lateral axis shown in (b) of FIG. 16 is on the X-axis or the Y-axis.

Figure 17:
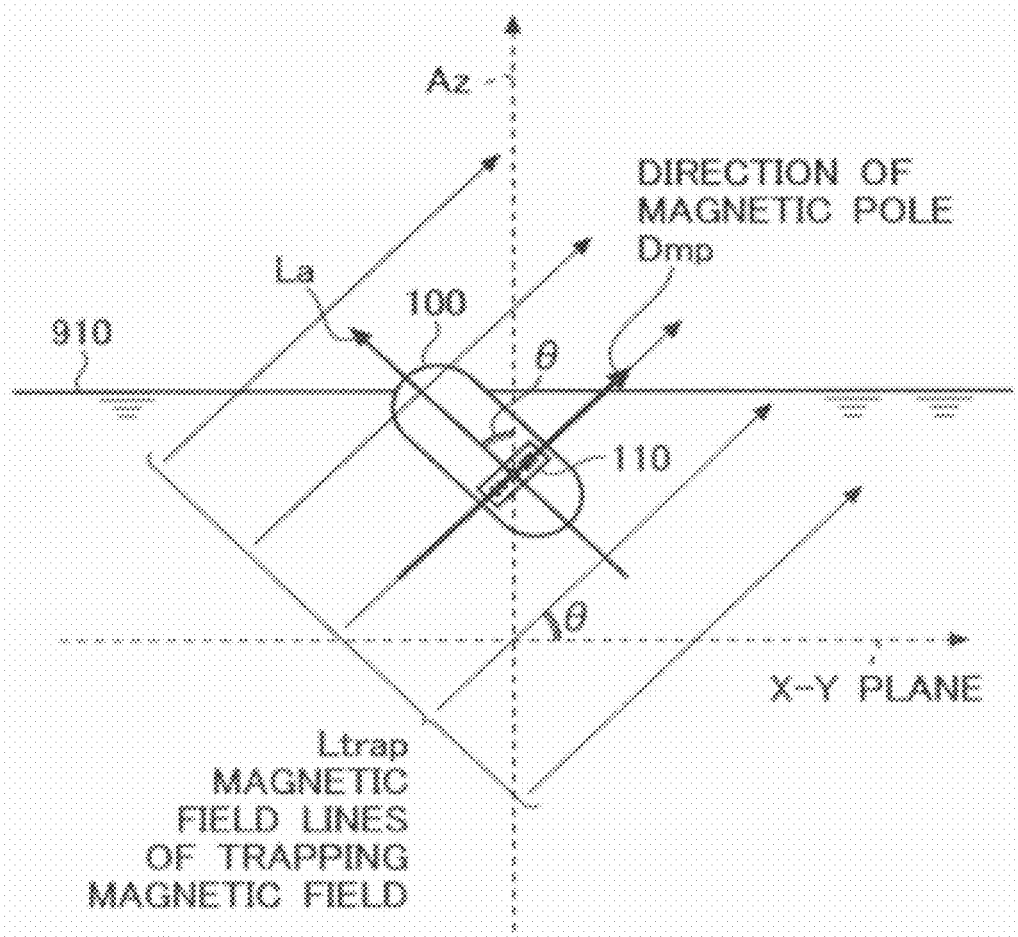
FIG. 17 is a diagram for explaining the direction of the capsule endoscope that is controlled by the trapping magnetic field in the first embodiment of the present invention.

The permanent magnet 110 is fixed to the casing 120 of the capsule endoscope 100. As shown in FIG. 17, because the trapping magnetic field Btrap is applied to the permanent magnet 110, the direction Dmp of the magnetic pole of the permanent magnet 110 becomes parallel to the direction of magnetic field lines Ltrap of the trapping magnetic field Btrap. As a result, the direction of the longitudinal axis La of the capsule endoscope 100 becomes perpendicular to the direction of the magnetic field lines Ltrap. As described above, the specific gravity of the capsule endoscope 100 to the liquid 910 is smaller than 1. Therefore, the Z-axis component in the direction of the longitudinal axis La of the capsule endoscope 100 is always positive (vertical). In the first embodiment, two parameters (i.e., the direction of the magnetic field lines of the trapping magnetic field Btrap and the specific gravity (<1) of the capsule endoscope 100 to the liquid 910) are used to uniquely control the posture of the capsule endoscope 100 in the liquid 910. FIG. 17 is a diagram for explaining the direction of the capsule endoscope 100 that is controlled by the tapping magnetic field Btrap.

For example, when the direction of the magnetic field lines Ltrap near the central Z-axis Az on the fluid level of the liquid 910 has an elevation angle θ to the X-Y plane, the direction of the longitudinal axis La of the capsule endoscope 100 has an angle θ to the central Z-axis Az and the Z-axis component of the longitudinal axis La is upward (+Z-axis direction). In the first embodiment, with the intensity of the trapping magnetic field Btrap, the direction of the magnetic field lines Ltrap and the direction of the magnetic pole of the permanent magnet 110 can approximately coincide with each other to such an extent that an error can be ignored.

An example of the gradient magnetic field generating coil 232 according to the first embodiment is explained in detail below with reference to the accompanying drawings. FIG. 18 is a perspective view of an example of the gradient magnetic field generating coil 232. FIG. 19A is a schematic diagram of an example of asymmetric magnetic fields Basx1/Basy1 and Basx2/Basy2 that are formed by X/Y-axis gradient coils 232x-1/232y-1 and 232x-2/232y-2 of the gradient magnetic field generating coil 232. FIG. 19B is a diagram of an example of the distribution of intensity of the gradient magnetic field Bgrad that is formed by the X/Y-axis gradient coil 232x-1/232y-1 and 232x-2/232y-2 that are shown in FIG. 19A.

As shown in FIG. 18, the gradient magnetic field generating coil 232 includes the X-axis gradient coils 232x-1 and 232x-2 in a pair that are arranged such that they sandwich the detecting space K above the bed 206 from the X-axis direction and the −X-axis direction; and the Y-axis gradient coils 232y-1 and 232y-2 in a pair that are similarly arranged such that they sandwich the detecting space K from the Y-axis direction and the −Y-axis direction. The gradient magnetic field generating coil 232 may be configured such that its position is controlled or not controlled by the relative position controller 240. The case where the gradient magnetic field generating coil 232 is fixed with respect to the detecting space K, i.e., the position of the gradient magnetic field generating coil 232 is not controlled by the relative position controller 240, is explained below.

The X/Y-axis gradient coils 232x-1/232y-1 and 232x-2/232y-2 generate the asymmetric magnetic fields Basx1/Basy1 and Basx2/Basy2, respectively. The asymmetric magnetic fields Basx1/Basy1 and Basx2/Basy2 have different intensities. In other words, the gradient magnetic field generator 230 shown in FIG. 4 can control the intensities of the asymmetric magnetic fields Basx1/Basy1 and Basx2/Basy2 that are generated by the X/Y-axis gradient coils 232x-1/232y-1 and 232x-2/232y-2, respectively.

In the first embodiment, as shown in FIG. 19A, by adjusting the balance between the asymmetric magnetic fields Basx1/Basy1 and Basx2/Basy2 that are generated by the X/Y-axis gradient coils 232x-1/232y-1 and 232x-2/232y-2 that are opposed to each other, the gradient magnetic fields Bgrad for urging the capsule endoscope 100 (specifically, the permanent magnet 110) in a target direction is formed in the detecting space K. In the example represented by FIGS. 19A and 19B, the gradient magnetic field Bgrad that attracts the capsule endoscope 100 in the X/Y-axis direction is formed.

The source of the gradient magnetic field Bgrad is not limited to the gradient magnetic field generating coil 232 shown in FIG. 18. Alternatively, for example, a gradient magnetic field generating coil 232A shown in FIG. 20 may be used. FIG. 20 is a perspective view of an example of the gradient magnetic field generating coil 232A of Modification 1-3 of the first embodiment. FIG. 21A is a schematic diagram of an example of asymmetric magnetic fields Basx1a/Basy1a and Basx2a/Basy2a that are formed by X/Y-axis gradient coils 232Ax-1/232Ay-1 and 232Ax-2/232Ay-2 of the gradient magnetic field generating coil 232A, respectively. FIG. 21B is a diagram of an example of the distribution of the intensity of the gradient magnetic field Bgrad that is formed by the X/Y-axis gradient coils 232Ax-1/232Ay-1 and 232Ax-2/232Ay-2, which are shown in FIG. 21A.

As shown in FIG. 20, the gradient magnetic field generating coil 232A includes the X-axis gradient coils 232Ax-1 and 232Ax-2 and the Y-axis gradient coils 232Ay-1 and 232Ay-2 that are arranged on planes approximately parallel to the mounting surface of the bed 206. The X-axis gradient coils 232Ax-1 and 232Ax-2 in a pair are arranged under the bed 206 along the X-axis. Similarly, the Y-axis gradient coils 232Ay-1 and 232Ay-2 in a pair are arranged under the bed 206 along the Y-axis. The X-axis gradient coils 232Ax-1/232Ax-2 and the Y-axis gradient coils 232Ay-1/232Ay-2 may overlap with each other.

The X/Y-axis gradient coils 232Ax-1/232Ay-1 and 232Ax-2/232Ay-2 generate the asymmetric magnetic fields Basx1a/Basy1a and Basx2a/Basy2a that have different intensities as the X/Y-axis gradient coils 232x-1/232y-1 and 232x-2/232y-2 do.

By adjusting the balance between the intensities of the asymmetric magnetic fields Basx1a/Basy1a and Basx2a/Basy2a that are generated by the X/Y-axis gradient coils 232Ax-1/232Ay-1 and 232Ax-2/232Ay-2, that are opposed to each other, as shown in FIG. 21A, the gradient magnetic field Bgrad for urging the capsule endoscope 100 (specifically, the permanent magnet 110) in a target direction can be formed in the detecting space K as shown in FIG. 21B.

Figure 22:
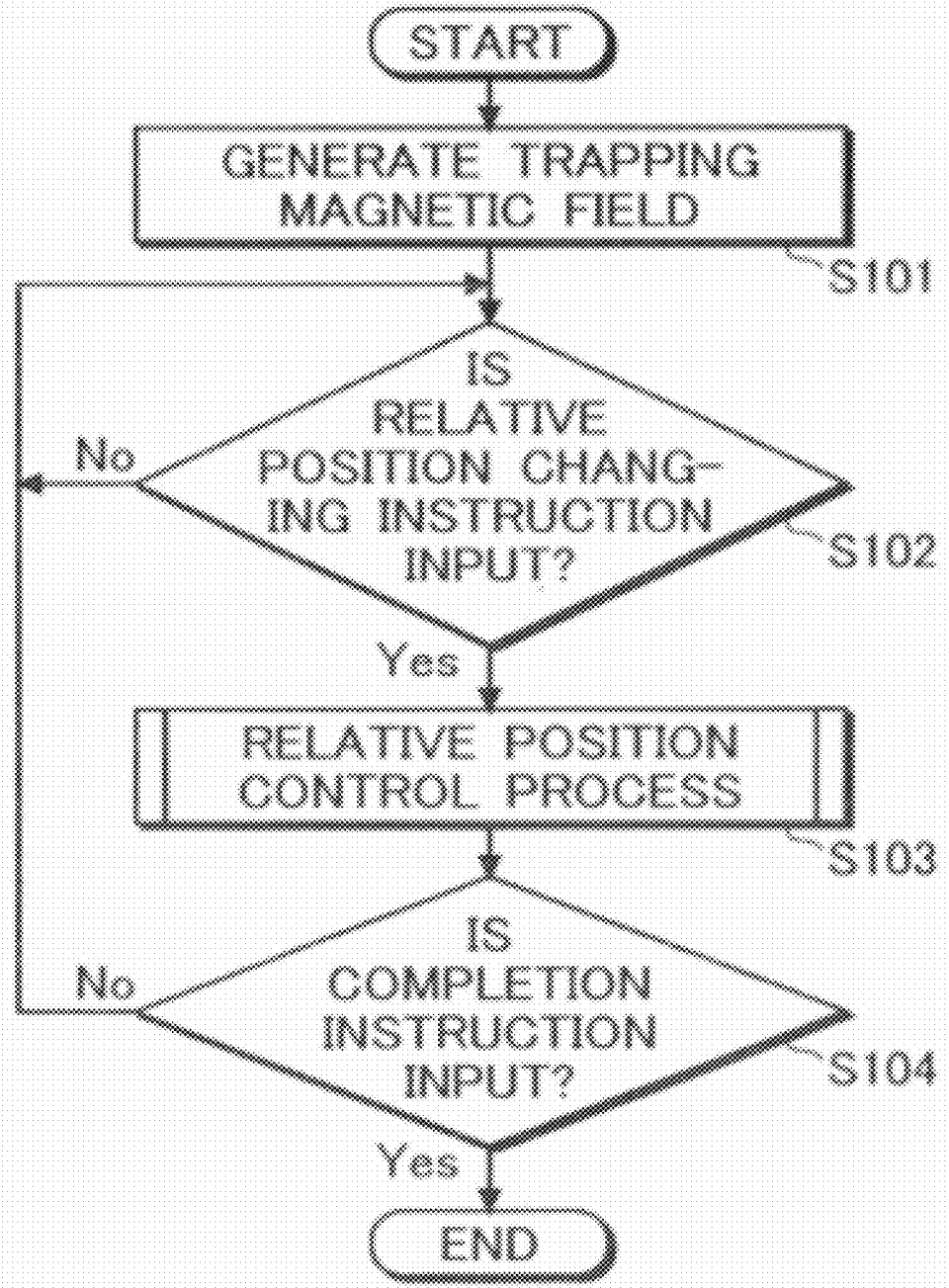
FIG. 22 is a flowchart of an example of overall operations of the position controlling apparatus according to the first embodiment of the present invention, which is performed to change the relative position between the bed and the trapping magnetic field generating coil.
Figure 23:
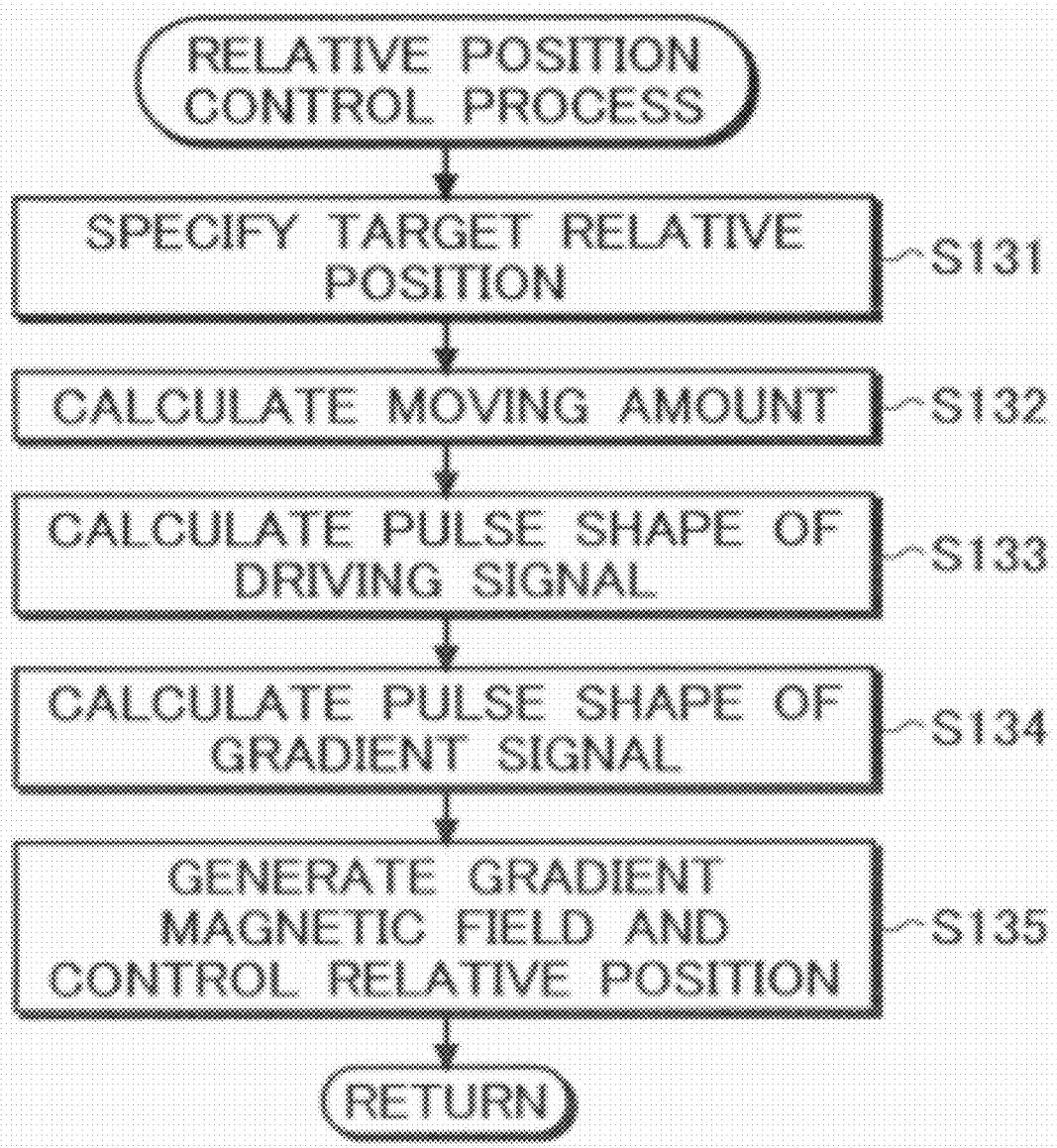
FIG. 23 is a flowchart of a specific example of a relative position control process shown in FIG. 22.

Operations of the capsule endoscope system 1 according to the first embodiment are explained in detail below with reference to the accompanying drawings. Explanation is provided mainly for an operation of the position controlling apparatus 200 of the capsule endoscope system 1, which is performed to change the relative position between the bed 206 (i.e., the subject 900) and the trapping magnetic field generating coil 222 (i.e., the central Z-axis Az). FIG. 22 is a flowchart of an example of operations of the position controlling apparatus 200, which is performed to change the relative position between the bed 206 and the trapping magnetic field generating coil 222. FIG. 23 is a flowchart of a specific example of a relative position control process (step S103) shown in FIG. 22.

As shown in FIG. 22, after being started, the position controlling apparatus 200 drives the trapping magnetic field generator 220 to form the trapping magnetic field Btrap in the detecting space K (step S01). Specifically, the position controlling apparatus 200 causes the trapping magnetic field generator 220 of the magnetic field generator 210 to generate a signal having a predetermined pulse shape and input the signal to the trapping magnetic field generating coil 222. Accordingly, the trapping magnetic field Btrap that holds the capsule endoscope 100 in the subject 900 on the central Z-axis Az is formed in the detecting space K and forces (trapping forces Ft1 and Ft2) that attract the capsule endoscope 100 to the central Z-axis Az are applied to the capsule endoscope 100 (see FIG. 16). At this stage, on the bed 206, i.e., in the detecting space K, for example, the subject 900 to whose stomach the liquid 910 and the capsule endoscope 100 are introduced is laid. Until an instruction for completing forming the trapping magnetic field Btrap is input (e.g., until this operation is completed), the trapping magnetic field Btrap is formed in the detecting space K.

Subsequently, the position controlling apparatus 200 determines whether the user inputs a relative position changing instruction for changing the relative position between the subject 900 and the central Z-axis Az (step S102) and waits to start the operation until the relative position changing instruction is input (NO at step S102). The relative position changing instruction that is input to the operating unit 260 is input to the relative position controller 240 and the magnetic field generator 210 through the controller 250.

When the relative position changing instruction is input (YES at step S102), the position controlling apparatus 200 performs the relative position control process for changing the relative position between the bed 206 and the trapping magnetic field generating coil 222 (step S103). A specific example of the relative position control process is explained in detail below with reference to FIG. 23.

When the relative position between the bed 206 and the trapping magnetic field generating coil 222 is changed through the relative position control process, the position controlling apparatus 200 determines whether a completing instruction is input from the operation unit 260 (step S104). When the completing instruction is input (YES at step S104), the position controlling apparatus 200 completes the operation. In contrast, when a completion instruction is not input (NO at step S104), the position controlling apparatus 200 returns to step S102 and performs the subsequent processes.

Specific examples of the relative position changing process at step S103 shown in FIG. 22 is explained in detail below with reference to FIG. 23. The case where the relative position controller 240 changes the relative position between the bed 206 (i.e., the subject 900) and the trapping magnetic field generating coil 222 (i.e., the central Z-axis Az) by moving only the bed 206 is explained below as an example.

As shown in FIG. 23, in the relative position controlling process of the position controlling apparatus 200, the controller 250 specifies the relative position (target relative position) that is input from the operating unit 260 (Step S131) and the controller 250 calculates the amount by which the bed 206 is moved (hereinafter, "moving amount") to move the bed 206 to the target relative position (step S132). In this example, the controller 250 calculates the amount (vector) by which the bed 206 is moved on the horizontal plane (X-Y plane).

Subsequently, in the position controlling apparatus 200, the controller 250 calculates a pulse shape (hereinafter, "driving signal pulse shape") of a driving signal to be input to the driving mechanism (not shown) that is connected to the bed 206 to move the bed 206 by the moving amount (vector) that is calculated at step S132 (step S133). The controller 250 inputs the driving signal pulse shape to the relative position controller 240.

The position controlling apparatus 200 calculates a pulse shape (hereinafter, "gradient signal pulse shape") of a signal (hereinafter, "gradient signal") for causing the gradient magnetic field generating coil 232 to generate the gradient magnetic field Bgrad whose intensity changes as the bed 206 moves based on the driving signal pulse shape that is calculated at step S133 (step S134). The specific examples of the gradient signal pulse shape are described in the explanation for Operation patterns 1 to 6 to be given below.

Subsequently, by inputting the driving signal pulse shape that is generated by the controller 250 to the relative position controller 240 and the gradient signal pulse shape that is generated by the controller 250 to the magnetic field generator 210, the position controlling apparatus 200 moves the bed 206 to set the relative position between the bed 206 and the trapping magnetic field generating coil 222 to the target relative position and forms, in the detecting space K, the gradient magnetic field Bgrad that causes the capsule endoscope 100 to generate a force for inhibiting the capsule endoscope 100 from deviating from the central Z-axis Az (step S135). Thereafter, the position controlling apparatus 200 returns to the operation represented in FIG. 22. In this manner, the capsule endoscope 100 is prevented from being away from the central Z-axis Az when the relative position between the bed 206 and the trapping magnetic field generating coil 222 is changed.

The operation patterns of the relative position controller 240 and the magnetic field generator 210 are explained in detail below with reference to the accompanying drawings. Explanations are given below, taking the following cases as examples: the case where, when the relative position controller 240 moves the bed 206 horizontally, the gradient magnetic field Bgrad is generated while the bed 206 is moved (Operation pattern 1), when the bed 206 starts to be moved (Operation pattern 2) or while the bed 206 is accelerated or decelerated (Operation pattern 3); and the case where, when the relative position controller 240 moves the trapping magnetic field generating coil 222 horizontally, the gradient magnetic field Bgrad is generated while the trapping magnetic field generating coil 222 is moved (Operation pattern 4), when the trapping magnetic field generating coil 222 starts to be moved (Operation pattern 5), or while the trapping magnetic field generating coil 222 is accelerated or decelerated (Operation pattern 6).

FIG. 24A is a timing chart for explaining Operation pattern 1 according to the first embodiment. FIG. 24B is a timing chart for explaining Operation pattern 2 according to the first embodiment. FIG. 24C is a timing chart for explaining Operation pattern 3 according to the first embodiment. FIG. 25 is a schematic diagram of an example of force that is generated in the capsule endoscope 100 and the gradient magnetic field Bgrad that is formed in the detecting space K while the bed 206 is accelerated in Operation pattern 3 represented in FIG. 24C. FIG. 26 is a schematic diagram of an example of the force that is generated in the capsule endoscope 100 and the gradient magnetic field Bgrad that is formed in the detecting space K while the bed 206 is decelerated in Operation pattern 3 represented in FIG. 24C. FIG. 27A is a timing chart for explaining Operation pattern 4 according to the first embodiment. FIG. 27B is a timing chart for explaining Operation pattern 5 according to the first embodiment. FIG. 27C is a timing chart for explaining Operation pattern 6 according to the first embodiment. FIG. 28 is a schematic diagram of an example of the force that is generated in the capsule endoscope 100 and the gradient magnetic field Bgrad that is formed in the detecting space K while the bed 206 is accelerated in Operation pattern 6 represented in FIG. 27C. FIG. 29 is a schematic diagram of an example of the force generated in the capsule endoscope 100 and the gradient magnetic field Bgrad that is formed in the detecting space K while the bed 206 is decelerated in Operation pattern 6 represented in FIG. 27C.

Because the trapping signal pulse shape and the intensity of trapping magnetic field are the same among Operation patterns 1 to 6, the trapping signal pulse shape and the intensity of trapping magnetic field are not shown in FIGS. 24B, 24C, and 27A to 27C. In the examples represented in FIGS. 24A to 24C and 27A to 27C, a gradient signal having a square wave is taken as an example. However, it is obvious that various modifications, such as a trapezoidal gradient signal, can be taken alternatively.

As shown in FIG. 24A, in Operation pattern 1, the magnetic field generator 210 causes the gradient magnetic field generator 230 to generate a gradient signal (see Timing t11 to t12 shown in (d) of FIG. 24A) while the relative position controller 240 moves the bed 206 (see Timing t11 to t12 of (c) of FIG. 24A) and inputs the gradient signal to the gradient magnetic field generating coil 232.

When the bed 206 is moved, to hold the capsule endoscope 100 near the central Z-axis Az, it is necessary to move the capsule endoscope 100 in the direction opposite to that in which the bed 206 is moved in the system in the subject 900 that moves with the bed 206 (i.e., in the liquid 910). In other words, it is necessary to attract the capsule endoscope 100 in the direction opposite to that in which the bed 206 is moved near the fluid level of the liquid 910. However, when the capsule endoscope 100 is to be attracted with respect to the liquid 910, a frictional force in the direction in which the capsule endoscope 100 is attracted (i.e., the direction in which the bed 206 is moved) is applied to the capsule endoscope 100. Therefore, the capsule endoscope 100 is to move in the direction in which the bed 206 is moved. To deal with the inconvenience, in Operation pattern 1, while the bed 206 is moved, the gradient magnetic field Bgrad that causes the permanent magnet 110 to generate a force to attract the capsule endoscope 100 in the direction opposite to that in which the bed 206 is moved is formed in the detecting space K (see Timing t11 to t12 shown in (e) of FIG. 24A). Accordingly, the frictional force that is generated in the capsule endoscope 100 can be canceled, so that the capsule endoscope 100 can be held near the peak of the trapping magnetic field Btrap (i.e., near the central Z-axis Az).

By driving the trapping magnetic field generator 220 during the whole operation or appropriately, the magnetic field generator 210 causes the trapping magnetic field generator 220 to generate a trapping signal (see (a) of FIG. 24A) and input the trapping signal to the trapping magnetic field generating coil 222. Therefore, the trapping magnetic field Btrap for holding the capsule endoscope 100 on the central Z-axis Az is formed in the detecting space K during the whole operation of the magnetic field generator 210 or appropriately (see (b) of FIG. 24A).

As shown in FIG. 24B, in Operation pattern 2, when the bed 206 starts to be moved by the relative position controller 240 (see Timing t21 to t22 shown in (a) of FIG. 24B), the magnetic field generator 210 causes the gradient magnetic field generator 230 to generate a gradient signal (see Timing t21 to t22 shown in (b) of FIG. 24B) and input the gradient signal to the gradient magnetic field generating coil 232.

When the bed 206 is moved, particularly when the bed 206 starts to be moved, the liquid 910 that is introduced into the subject 900, which moves with the bed 206, remains on the side opposite to the direction in which the bed 206 is moved because of the inertia force. Thereafter, the liquid 910 returns to the still state by wave breaking. Because of the wave breaking, a horizontal force larger than that obtained when the bed 206 is moved at a constant speed is applied to the capsule endoscope 100. The force is in the same direction as that in which the bed 206 is moved. Thus, the capsule endoscope 100 is to deviate strongly from the central Z-axis Az particularly when the bed 206 starts to be moved.

To deal with the inconvenience, in Operation pattern 2, when the bed 206 starts to be moved, the gradient magnetic field Bgrad that causes the permanent magnet 110 to generate a force that attracts the capsule endoscope 100 in the direction opposite to that in which the bed 206 is moved is formed in the detecting space K temporarily (see Timing t21 to t22 shown in (c) of FIG. 24B). Accordingly, the large force that is applied by the liquid 910 to the capsule endoscope 100 can be canceled when the bed 206 starts to be moved. Thus, the capsule endoscope 100 can be held near the peak of the trapping magnetic field Btrap (i.e., near the central Z-axis Az).

In Operation pattern 2, the frictional force that the liquid 910 causes the capsule endoscope 100 to generate when the bed 206 moves at a constant speed is ignored. Operation pattern 1 may be combined with Operation pattern 2 to cancel the frictional force that the liquid 910 applies to the capsule endoscope 100 when the bed 206 moves at a constant speed. In Operation pattern 2, the force that the capsule endoscope 100 receives from the liquid 910 is canceled by wave breaking caused when the bed 206 starts to be moved. Alternatively, the force that the capsule endoscope 100 receives from the liquid 910 may be canceled by wave breaking caused when the bed 206 stops.

As shown in FIG. 24C, in Operation pattern 3, while the relative position controller 240 accelerates the bed 206 (see Timing t31 to t32 shown in (b) of FIG. 24C), i.e., while the relative position controller 240 inputs a driving signal for accelerating the bed 206 to the driving mechanism (not shown) (see Timing t31 to t32 shown in (a) of FIG. 24C), the magnetic field generator 210 causes the gradient magnetic field generator 230 to generate a gradient signal (see Timing t31 to t32 shown in (d) of FIG. 24C) and input the gradient signal to the gradient magnetic field generating coil 232.

As shown in a portion (a) of FIG. 25, while the bed 206 is accelerated, a force that is to move with the system in the subject 900 on the bed 206, i.e., an inertia force F_ina that is to move as the liquid 910, which is introduced into the subject 900, moves is applied to the capsule endoscope 100. The inertia force F_ina works in the direction same as that in which the bed 206 is accelerated, i.e., the direction in which the bed 206 is moved. Therefore, the capsule endoscope 100 is to deviate from the central Z-axis Az while the bed 206 is accelerated.

To deal with the above inconvenience, in Operation pattern 3, while the bed 206 is accelerated, the gradient magnetic field Bgrad that causes the permanent magnet 110 to generate a force (a canceling force F_cna) in the direction opposite to that in which the bed 206 is accelerated is temporarily formed in the detecting space K (see timing t31 to t32 shown in (e) of FIG. 24C and a portion (b) of FIG. 25). Thus, while the bed 206 is accelerated, the inertia force F_ina that is generated in the capsule endoscope 100 can be canceled. Accordingly, the capsule endoscope 100 can be held near the peak of the trapping magnetic field Btrap (i.e., near the central Z-axis Az).

In contrast, as shown in FIG. 24C, in Operation pattern 3, while the bed 206 is decelerated by the relative position controller 240 (see Timing t33 to t34 shown in (b) of FIG. 24C), i.e., while the relative position controller 240 inputs a driving signal for decelerating the bed 206 to the driving mechanism (not shown) (see Timing t33 to t34 shown in (a) of FIG. 24C), the magnetic field generator 210 causes the gradient magnetic field generator 230 to generate a gradient signal (see Timing t33 to t34 shown in (d) of FIG. 24C) and input the gradient signal to the gradient magnetic field generating coil 232.

As shown in a portion (a) of FIG. 26, while the bed 206 is decelerated, an inertia force F_inb in the direction opposite to the inertia force F_ina that is applied while the bed 206 is accelerated is applied to the capsule endoscope 100. Thus, the capsule endoscope 100 is to deviate from the central Z-axis Az particularly while the bed 206 is decelerated.

To deal with the above inconvenience, while the bed 206 is decelerated, the gradient magnetic field Bgrad that causes the permanent magnet 110 to cause a force (a canceling force F_cnb) in the direction opposite to that in which the bed 206 is decelerated is temporarily formed in the detecting space K (see timing t33 to t34 shown in (e) of FIG. 24C and a portion (b) of FIG. 26). Thus, while the bed 206 is decelerated, the inertia force F_inb that is generated in the capsule endoscope 100 can be canceled. Accordingly, the capsule endoscope 100 can be held near the peak of the trapping magnetic field Btrap (i.e., near the central Z-axis Az).

In Operation pattern 3, following forces are ignored: the frictional force that the liquid 910 applies to the capsule endoscope 100 when the bed 206 moves at a constant speed; and the force that the capsule endoscope 100 receives from the liquid 910 due to wave braking when the bed 206 starts to be moved. Operation pattern 1 and/or Operation pattern 2 may be combined with Operation pattern 3 to cancel the frictional force that the liquid 910 applies to the capsule endoscope 100 when the bed 206 moves at a constant speed and/or the force that the capsule endoscope 100 receives from the liquid 910 due to wave braking when the bed 206 starts to be moved.

As shown in FIG. 27A, in Operation pattern 4, while the relative position controller 240 moves the trapping magnetic field generating coil 222 (see Timing t41 to t42 shown in (a) of FIG. 27A), the magnetic field generator 210 causes the gradient magnetic field generator 230 to generate a gradient signal (see Timing t41 to t42 shown in (b) of FIG. 27A) and input the gradient signal to the gradient magnetic field generating coil 232.

When the trapping magnetic field generating coil 222 is moved, in order to hold the capsule endoscope 100 near the central Z-axis Az, it is necessary to move the capsule endoscope 100 in the same direction as that in which the trapping magnetic field generating coil 222 is moved in the liquid 910 that is introduced into the subject 900. In other words, it is necessary to attract the capsule endoscope 100 near the fluid level of the liquid 910 in the same direction as that in which the trapping magnetic field generating coil 222 is moved. However, when the capsule endoscope 100 is to be attracted with respect to the liquid 910, a frictional force in the direction opposite to that in which the capsule endoscope 100 is moved (the direction in which the trapping magnetic field generating coil 222 is moved) is generated in the capsule endoscope 100. Thus, the capsule endoscope 100 cannot follow the peak of the trapping magnetic field Btrap that moves as the trapping magnetic field generating coil 222 moves, so that the capsule endoscope 100 moves following the trapping magnetic field generating coil 222. In Operation pattern 4, while the trapping magnetic field generating coil 222 is moved, the gradient magnetic field Bgrad that causes the permanent magnet 110 to generate a force that attracts the capsule endoscope 100 in the same direction as that in which the trapping magnetic field generating coil 222 is moved is formed in the detecting space K (see Timing t41 to t42 shown in (c) of FIG. 27A). Thus, the frictional force that is generated in the capsule endoscope 100 is canceled. Accordingly, the capsule endoscope 100 can be held near the peak of the trapping magnetic field Btrap (i.e., near the central Z-axis Az).

As shown in FIG. 27B, in Operation pattern 5, when the relative position controller 240 starts moving the trapping magnetic field generating coil 222 (see Timing t51 to t52 shown in (a) of FIG. 27B), the magnetic field generator 210 causes the gradient magnetic field generator 230 to generate a gradient signal (see Timing t51 to t52 shown in (b) of FIG. 27B) and input the gradient signal to the gradient magnetic field generating coil 232.

When the gradient magnetic field generating coil 232 is moved, particularly when the gradient magnetic field generating coil 232 starts to be moved, an inertia force to hold the capsule endoscope 100 in the present position is applied to the capsule endoscope 100. Therefore, the capsule endoscope 100 cannot follow the peak of the trapping magnetic field Btrap that moves as the trapping magnetic field generating coil 222 moves, and the capsule endoscope 100 moves following the trapping magnetic field generating coil 222.

To deal with the above inconvenience, in Operation pattern 5, when the trapping magnetic field generating coil 222 starts to be moved, the gradient magnetic field Bgrad that causes the permanent magnet 110 to generate a force that attracts the capsule endoscope 100 in the same direction as that in which the trapping magnetic field generating coil 222 is moved is temporarily formed in the detecting space K (see Timing t51 to t52 shown in (c) of FIG. 27B). Thus, the capsule endoscope 100 can start to be moved along with the start of moving the trapping magnetic field generating coil 222. Accordingly, the capsule endoscope 100 can be held near the peak of the trapping magnetic field Btrap (i.e., near the central Z-axis Az).

In Operation pattern 5, the frictional force that the liquid 910 causes the capsule endoscope 100 to generate when the trapping magnetic field generating coil 222 moves at a constant speed is ignored. Operation pattern 4 may be combined with Operation pattern 5 to cancel the frictional force that the liquid 910 applies to the capsule endoscope 100 when the trapping magnetic field generating coil 222 moves at a constant speed. In Operation pattern 5, a delay of start of moving the capsule endoscope 100 caused when the trapping magnetic field generating coil 222 is canceled. Alternatively, a delay of stopping the capsule endoscope 100 may be canceled with, for example, an inertia force when the trapping magnetic field generating coil 222 is stopped.

As shown in FIG. 27C, in Operation pattern 6, while the relative position controller 240 accelerates the trapping magnetic field generating coil 222 (see Timing t61 and t62 shown in (b) of FIG. 27C), i.e., while the relative position controller 240 inputs a driving signal for accelerating the trapping magnetic field generating coil 222 to the driving mechanism (not shown) (see Timing t61 and t62 shown in (a) of FIG. 27C), the magnetic field generator 210 causes the gradient magnetic field generator 230 to generate a gradient signal (see Timing t61 and t62 shown in (d) of FIG. 27C) and input the gradient signal to the gradient magnetic field generating coil 232.

As shown in a portion (a) of FIG. 28, while the trapping magnetic field generating coil 222 is accelerated, a force that is to hold the capsule endoscope 100 at the present position, i.e., an inertia force F_inc, is applied to the capsule endoscope 100. The inertia force F_inc is in the direction opposite to that in which the trapping magnetic field generating coil 222 is accelerated, i.e., in the direction in which the trapping magnetic field generating coil 222 is moved. Therefore, the capsule endoscope 100 is to deviate from the central Z-axis Az while the trapping magnetic field generating coil 222 is accelerated.

To deal with the above inconvenience, in Operation pattern 6, while the trapping magnetic field generating coil 222 is accelerated, the gradient magnetic field Bgrad that causes the permanent magnet 110 to generate a force (a canceling force F_cnc) in the direction same as that in which the trapping magnetic field generating coil 222 is accelerated is temporarily formed in the detecting space K (see timing t61 to t62 shown in (e) of FIG. 27C and a portion (b) of FIG. 28). Thus, while the trapping magnetic field generating coil 222 is accelerated, the inertia force F_inc that is generated in the capsule endoscope 100 can be canceled. Accordingly, the capsule endoscope 100 can be held near the peak of the trapping magnetic field Btrap (i.e., near the central Z-axis Az).

As shown in FIG. 27C, in Operation pattern 6, while the relative position controller 240 decelerates the trapping magnetic field generating coil 222 (see Timing t63 and t64 shown in (b) of FIG. 27C), i.e., while the relative position controller 240 inputs a driving signal for decelerating the trapping magnetic field generating coil 222 to the driving mechanism (not shown) (see Timing t63 and t64 shown in (a) of FIG. 27C), the magnetic field generator 210 causes the gradient magnetic field generator 230 to generate a gradient signal (see Timing t63 to t64 shown in (d) of FIG. 27C) and input the gradient signal to the gradient magnetic field generating coil 232.

As shown in a portion (a) of FIG. 29, while the trapping magnetic field generating coil 222 is decelerated, an inertia force F_ind that is caused because of the movement following the movement of the trapping magnetic field generating coil 222 is applied to the capsule endoscope 100. The inertia force F_ind is in the direction opposite to that of the inertia force F_inc that is caused when the trapping magnetic field generating coil 222 is accelerated. Thus, the capsule endoscope 100 is to deviate from the central Z-axis Az particularly while the trapping magnetic field generating coil 222 is decelerated.

To deal with the above inconvenience, in Operation pattern 6, while the trapping magnetic field generating coil 222 is decelerated, the gradient magnetic field Bgrad that causes the permanent magnet 110 to generate a force (a canceling force F_cnd) in the direction same as that in which the trapping magnetic field generating coil 222 is decelerated is temporarily formed in the detecting space K (see timing t63 to t64 shown in (e) of FIG. 27C and a portion (b) of FIG. 29). Thus, while the trapping magnetic field generating coil 222 is decelerated, the inertia force F_ind that is generated in the capsule endoscope 100 can be canceled. Accordingly, the capsule endoscope 100 can be held near the peak of the trapping magnetic field Btrap (i.e., near the central Z-axis Az).

As described above, in the first embodiment, when the relative position between the subject 900 and the central Z-axis Az of the trapping magnetic field generating coil 222 is changed, the gradient magnetic field Bgrad that attracts the capsule endoscope 100 (specifically, the permanent magnet 110) in the direction same as or opposite to that in which the relative position is changed is formed in the detecting space K. In other words, the magnetic field that includes at least one of the trapping magnetic field component (i.e., the trapping magnetic field Btrap) that attracts the permanent magnet 110 to the central Z-axis Az and the gradient magnetic field component (i.e., the gradient magnetic field Bgrad) that attracts the permanent magnet 110 in the direction same as or opposite to the direction in which the relative position is changed is formed in the detecting space K in which the subject 900 is laid. Thus, in the first embodiment, deviation of the capsule endoscope 100 from the central Z-axis Az is reduced when the relative position is changed. Accordingly, the state where the capsule endoscope 100 is trapped in a desirable trapping position can be maintained accurately.

In the first embodiment, the case where the capsule endoscope 100 floats near the fluid level of the liquid 910 is taken as an example. Alternatively, for example, a magnetic field that attracts the permanent magnet 110 vertically, i.e., in the direction in which the permanent magnet 110 is attracted into the liquid 910 may be generated, so that the capsule endoscope 100 submerges in the liquid 910.

A capsule endoscope system 2 according to a second embodiment of the present invention is explained in detail below with reference to the accompanying drawings. In the second embodiment, the capsule endoscope system 2 using, as a body insertable apparatus, the capsule endoscope 100 same as that of the first embodiment is taken as an example. However, as in the case of the first embodiment, various body-insertable apparatuses can be used, such as a single-eye or multi-eye capsule endoscope that takes in-vivo images of a subject by performing an image-taking operation while moving through the lumen from the esophagus to the anus of the subject. In the following explanation, the constituents same as those of the first embodiment are denoted by the same reference numerals and the same explanations are not repeated.

Figure 30:
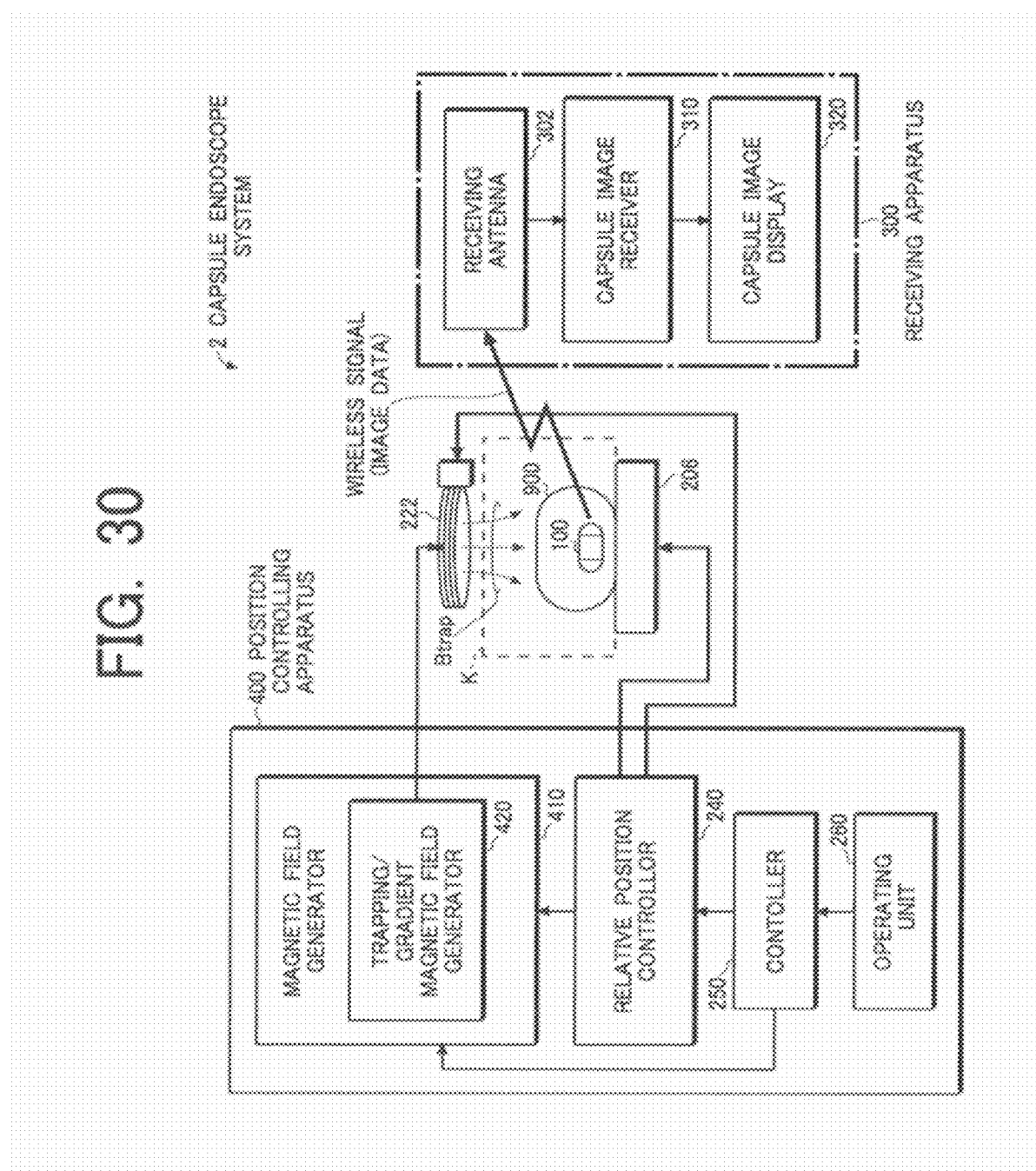
FIG. 30 is a block diagram of a configuration of a capsule endoscope system according to a second embodiment of the present invention.

FIG. 30 is a block diagram of a configuration of the capsule endoscope system 2 according to the second embodiment. As shown in FIG. 30, the configuration of the capsule endoscope system 2 is similar to that of the first embodiment except that the position controlling apparatus 200 is replaced by a position controlling apparatus 400.

The position controlling apparatus 400 includes a magnetic field generator 410 that forms a trapping magnetic field Btrap to be described below; the relative position controller 240 that controls the relative position between the subject 900 and the central Z-axis Az of the trapping magnetic field Btrap; the controller 250 that controls the magnetic field generator 410 and the relative position controller 240; and the operating unit 260 through which a user inputs various controlling commands to the controller 250. The relative position controller 240, the controller 250, and the operating unit 260 are same as those of the first embodiment.

The magnetic field generator 410 includes a trapping/gradient magnetic field generator 420 that generates a trapping magnetic field Btrap. The trapping/gradient magnetic field generator 420 is electrically connected to the trapping magnetic field generating coil 222 same as that of the first embodiment. As in the case of the first embodiment, the trapping magnetic field generating coil 222 is provided in a housing (corresponding to the housing 202 shown in FIG. 5) of the position controlling apparatus 400 and under the bed 206, for example.

When the relative position between the bed 206 and the central Z-axis Az of the trapping magnetic field generating coil 222 is not changed, the trapping/gradient magnetic field generator 420 generates a current signal (hereinafter, "trapping signal") having a specific amplitude and inputs the trapping signal to the trapping magnetic field generating coil 222 under the control of the controller 250. Accordingly, the trapping magnetic field Btrap for holding the capsule endoscope 100 that includes the permanent magnet 110 in a target position (position on the central Z-axis Az of the component of the trapping magnetic field Btrap) is formed in the detecting space K.

When the relative position controller 240 changes the relative position between the bed 206 and the central Z-axis of the trapping magnetic field generating coil 222, the trapping/gradient magnetic field generator 420 generates a current signal (hereinafter, "shifted peak trapping signal") that causes the trapping magnetic field generating coil 222 to form a shifted peak trapping magnetic field Bstrp whose peak of intensity is shifted in a target direction and input the shifted peak trapping signal to the trapping magnetic field generating coil 222, for example, under the control of the controller 250. Accordingly, the trapping magnetic field Bstrp that can hold the capsule endoscope 100, which includes the permanent magnet 110, near the central Z-axis Az while urging the capsule endoscope 100 in a target direction (for example, the direction in which the bed 206 is accelerated or the direction opposite to that in which the bed 206 is accelerated) can be formed in the detecting space K. This inhibits the capsule endoscope 100 from deviating from the central Z-axis Az when the relative position between the bed 206 and the central Z-axis Az of the trapping magnetic field generating coil 222 is changed.

As described above, in the second embodiment, The trapping/gradient magnetic field generator 420 and the magnetic field generator 410 that includes the trapping magnetic field generating coil 222, which is connected to the trapping/gradient magnetic field generator 420, function as a magnetic field generating mechanism that forms, in the detecting space K in which the subject 900 is laid, a magnetic field (the trapping magnetic field Btrap or the shifted peak trapping magnetic field Bstrp) that includes at least one of the trapping magnetic field component (i.e., the trapping magnetic field Btrap) that attracts the permanent magnet 110 to the central Z-axis Az and the gradient magnetic field component (i.e., the gradient magnetic field Bgrad) that attracts the permanent magnet 110 in the direction same as or opposite to that in which the relative position is changed.

The shifted peak trapping signal, which is generated by the trapping/gradient magnetic field generator 420, and the shifted peak trapping magnetic field Bstrp, which is formed by the trapping magnetic field generating coil 222 in the detecting space K, are explained in detail below.

As explained with respect to Operation patterns 1 to 6 of the first embodiment, when the relative position between the trapping magnetic field generating coil 222 and the bed 206 is changed, a force in the direction in which the bed 206 is moved or the direction opposite to that in which the bed 206 is moved is applied to the capsule endoscope 100. For this reason, when the relative position between the bed 206 and the trapping magnetic field generating coil 222 is changed horizontally, the capsule endoscope 100 is to deviate from the central Z-axis Az of the trapping magnetic field generating coil 222.

To deal with the above inconvenience, in the second embodiment, when the relative position between the bed 206 and the central Z-axis Az of the trapping magnetic field generating coil 222 is changed, the trapping magnetic field generating coil 222 is caused to form the shifted peak trapping magnetic field Bstrp whose peak of intensity is shifted in a target direction.

The target direction is, for example, in the same situation as Operation pattern 1, the direction opposite to that in which the bed 206 is moved; in the same situation as Operation pattern 2, the direction opposite to that in which the bed 206 is moved; in the same situation as Operation pattern 3, the direction opposite to that in which the bed 206 is accelerated while the bed 206 is accelerated, or the direction opposite to that in which the bed 206 is decelerated while the bed 206 is decelerated; in the same situation as Operation pattern 4, the direction same as that in which trapping magnetic field generating coil 222 is moved; in the same situation as Operation pattern 5, the same direction as that in which the trapping magnetic field generating coil 222 is moved; and, in the same situation as Operation pattern 6, the same direction as that in which the trapping magnetic field generating coil 222 is accelerated while the trapping magnetic field generating coil 222 is accelerated, and the same direction as that in which the trapping magnetic field generating coil 222 is decelerated while the trapping magnetic field generating coil 222 is decelerated.

The trapping magnetic field Btrap/shifted peak trapping magnetic field Bstrp, which is formed by the trapping magnetic field generating coil 222, and the force that is received by the permanent magnet 110 of the capsule endoscope 100 due to the trapping magnetic field Btrap/shifted peak trapping magnetic field Bstrp are explained in detail below with reference to the accompanying drawings.

When the permanent magnet 110 in the capsule endoscope 100 is regarded as a magnetic dipole moment M, a force F that the magnetic dipole moment M receives due to a magnetic field B, which is formed by the coil, is represented by the following Equation (1) where Fx, Fy, and Fz are an X component, a Y component, and a Z component of the force F, respectively, and Mx, My, and $M_Z$ are an X component, a Y component, and a Z component of the magnetic dipole moment M, respectively.

$$\begin{pmatrix} Fx \\ Fy \\ Fz \end{pmatrix} = \begin{pmatrix} \frac{dB_X}{dx} & \frac{dB_Y}{dx} & \frac{dB_Z}{dx} \\ \frac{dB_X}{dy} & \frac{dB_Y}{dy} & \frac{dB_Z}{dy} \\ \frac{dB_X}{dz} & \frac{dB_Y}{dz} & \frac{dB_Z}{dz} \end{pmatrix} \begin{pmatrix} M_X \\ M_Y \\ M_Z \end{pmatrix} \quad (1)$$

$$= \begin{pmatrix} M_X\left(\frac{dB_X}{dx}\right) + M_Y\left(\frac{dB_Y}{dx}\right) + M_Z\left(\frac{dB_Z}{dx}\right) \\ M_X\left(\frac{dB_X}{dy}\right) + M_Y\left(\frac{dB_Y}{dy}\right) + M_Z\left(\frac{dB_Z}{dy}\right) \\ M_X\left(\frac{dB_X}{dz}\right) + M_Y\left(\frac{dB_Y}{dz}\right) + M_Z\left(\frac{dB_Z}{dz}\right) \end{pmatrix}$$

Based on Equation (1), a force FZ that the magnetic dipole moment M receives from a magnetic field (regarded as a magnetic field BZ) formed by the Z-axis trapping coil 222z of the trapping magnetic field generating coil 222 is represented by the following Equation (2).

$$\begin{pmatrix} FZx \\ FZy \\ FZz \end{pmatrix} = \begin{pmatrix} M_X\left(\frac{dBZ_X}{dx}\right) + M_Y\left(\frac{dBZ_Y}{dx}\right) + M_Z\left(\frac{dBZ_Z}{dx}\right) \\ M_X\left(\frac{dBZ_X}{dy}\right) + M_Y\left(\frac{dBZ_Y}{dy}\right) + M_Z\left(\frac{dBZ_Z}{dy}\right) \\ M_X\left(\frac{dBZ_X}{dz}\right) + M_Y\left(\frac{dBZ_Y}{dz}\right) + M_Z\left(\frac{dBZ_Z}{dz}\right) \end{pmatrix} \quad (2)$$

Figure 31A:
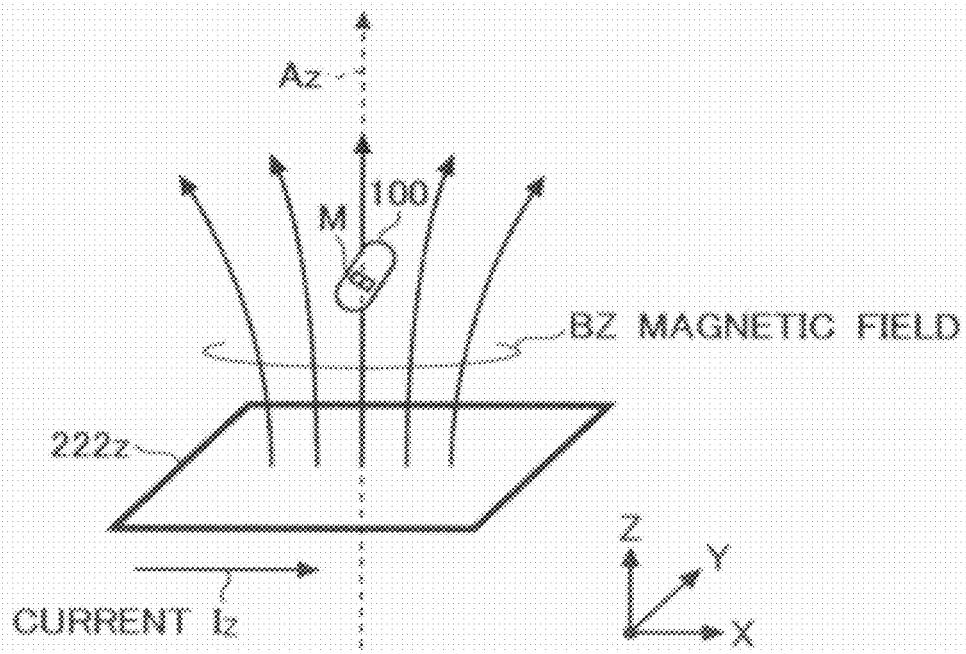
FIG. 31A is a schematic diagram of a magnetic field that is formed near the central Z-axis by the Z-axis trapping coil when a current is applied to the Z-axis trapping coil in the second embodiment.
Figure 31B:
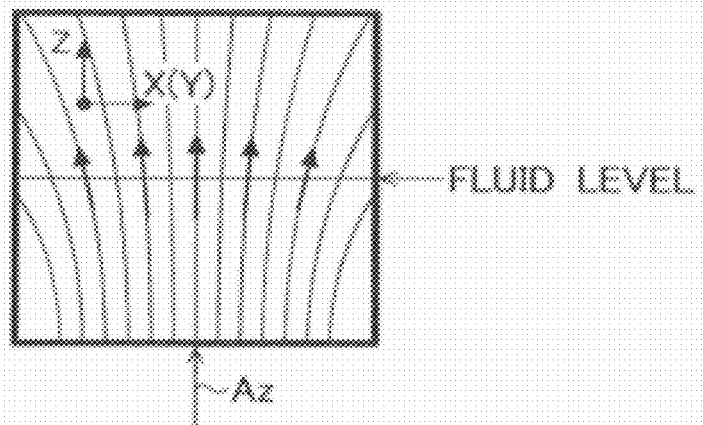
FIG. 31B is a diagram representing a component of the magnetic field shown in FIG. 31A on a plane including the central Z-axis.
Figure 32A:
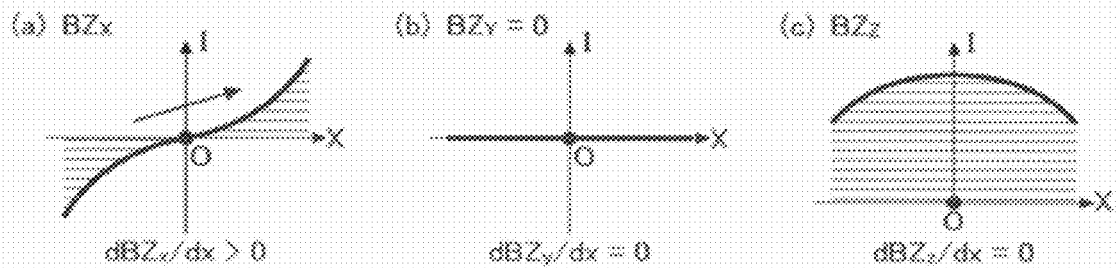
FIG. 32A is a diagram representing the intensity of the magnetic field shown in FIGS. 31A and 31B in the X-axis direction.
Figure 32B:
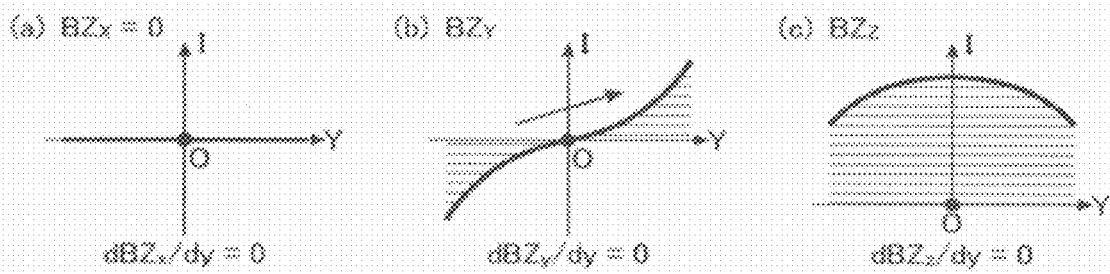
FIG. 32B is a diagram representing the intensity of the magnetic field shown in FIGS. 31A and 31B in the Y-axis direction.
Figure 32C:
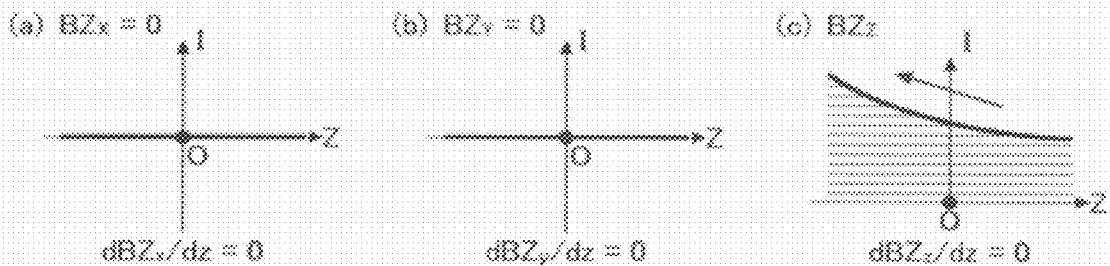
FIG. 32C is a diagram representing the intensity of the magnetic field shown in FIGS. 31A and 31B in the Z-axis direction.

The force F that is applied to the permanent magnet 110 on the central Z-axis Az is examined below. First, the magnetic field BZ that is formed near the central Z-axis Az by the Z-axis trapping coil 222z is examined. FIG. 31A is a schematic diagram of the magnetic field BZ that is formed near the central Z-axis Az by the Z-axis trapping coil 222z when a current IZ is applied to the Z-axis trapping coil 222z in the second embodiment. FIG. 31B is a diagram representing components of the magnetic field BZ shown in FIG. 31A on a plane including the central Z-axis Az. FIG. 32A is a diagram representing the intensity of the magnetic field BZ in the X-axis direction. FIG. 32B is a diagram representing the intensity of the magnetic field BZ in the Y-axis direction. FIG. 32C is a diagram representing the intensity of the magnetic field BZ in the Z-axis direction. FIGS. 32A to 32C represent magnetic field intensity in each axis direction in the case where the magnetic field BZ is positive, i.e., the magnetic field component on the central Z-axis Az extends vertically upward. An origin O shown in FIGS. 32A to 32C is the intersection between the central Z-axis Az and an arbitrary X-Y plane (for example, the fluid level of the liquid 910).

As shown in FIGS. 31A and 31B, when the current Iz is input to the Z-axis trapping coil 222z, the magnetic field BZ that is parallel to the central Z-axis Az on the central Z-axis Az, and whose magnetic field lines are oblique to the central Z-axis Az as the magnetic field BZ deviates from the central Z-axis Az, is formed on the plane including the central Z-axis Az and near the fluid level of the liquid 910.

The intensity (gradient) of the magnetic field BZ on the X-axis is as shown in FIG. 32A. A portion (a) of FIG. 32A represents the intensity $BZ_X$ of a component in the X-axis direction of the magnetic field BZ on the X-axis. A portion (b) of FIG. 32A represents the intensity $BZ_Y$ of a component in the Y-axis direction of the magnetic field BZ on the X-axis. A portion (c) of FIG. 32A represents the intensity $BZ_Z$ of a component in the Z-axis direction of the magnetic field BZ on the X-axis.

As shown in (a) of FIG. 32A, the positive/negative value of the intensity $BZ_X$ of the component in the X-axis direction of the magnetic field BZ on the X-axis, i.e., the direction of the component, reverse at the border of the origin O on the X-axis. The absolute value of the intensity $BZ_X$ on the X-axis becomes large as the position deviates from the origin O. Accordingly, the intensity $BZ_X$ near the origin O (for example, near the intersection between the central Z-axis Az and the fluid level of the liquid 910) has a gradient with which the magnetic dipole moment M (the permanent magnet 110) is attracted to the +X side. As shown in (c) of FIG. 32A, the distribution of the intensity $BZ_Z$ of the Z-axis component of the magnetic field BZ on the X-axis is such that the peak of the intensity $BZ_Z$ is at the origin O on the X-axis, thereby forming a swelling shape. As shown in (b) of FIG. 32A, the intensity $BZ_Y$ of the component on the Y-axis of the magnetic field BZ in the X-axis direction is 0($BZ_Y$=0).

The intensity (gradient) of the magnetic field BZ on the Y-axis is as shown in FIG. 32B. A portion (a) of FIG. 32B represents the intensity $BZ_X$ of a component in the X-axis direction of the magnetic field BZ on the Y-axis. A portion (b)

of FIG. 32B represents the intensity $BZ_Y$ of a component of the Y-axis direction of the magnetic field BZ on the Y-axis. A portion (c) of FIG. 32B represents the intensity $BZ_Z$ of a component of the Z-axis direction of the magnetic field BZ on the Y-axis.

As shown in (b) and (c) of FIG. 32B, the intensity $BZ_Y$ of the component in the Y-axis direction of the magnetic field BZ on the Y-axis and the intensity $BZ_Z$ of the component in the Z-axis direction of the magnetic field BZ on the Y-axis are respectively similar to the intensity $BZ_X$ of the component in the X-axis direction of the magnetic field BZ on the X-axis, which is represented in (c) of FIG. 32A, and the intensity $BZ_Z$ of the component in the Z-axis direction of the magnetic field BZ on the X-axis, which is represented in (c) of FIG. 32A. As shown in (a) of FIG. 32B, the intensity $BZ_X$ of the component in the X-axis direction of the magnetic field BZ in the Y-axis direction is $0 (BZ_X=0)$.

The intensity (gradient) of the magnetic field BZ on the Z-axis is as shown in FIG. 32C. A portion (a) of FIG. 32C represents the intensity $BZ_X$ of a component of the X-axis direction of the magnetic field BZ on the Z-axis. A portion (b) of FIG. 32C represents the intensity $BZ_Y$ of a component in the Y-axis direction of the magnetic field BZ on the Z-axis. A portion (c) of FIG. 32C represents the intensity $BZ_Z$ of a component in the Z-axis direction of the magnetic field BZ on the Z-axis.

As shown in (c) of FIG. 32C, the intensity $BZ_Z$ of the component in the Z-axis direction of the magnetic field BZ on the Z-axis becomes smaller towards the side of the +Z direction. Therefore, the intensity $BZ_Z$ near the origin O (for example, near the intersection between the central Z-axis Az and the fluid level of the liquid 910) has a gradient with which the magnetic dipole moment M (the permanent magnet 110) is attracted to the −Z side. As shown in (a) and (b) of FIG. 32C, the intensity $BZ_X$ of the component in the X-axis direction of the magnetic field BZ on the Z-axis and the intensity $BZ_Y$ of the component in the Y-axis direction of the magnetic field BZ on the Z-axis are respectively $0 (BZ_X=0, BZ_Y=0)$.

The characteristics represented by FIGS. 32A to 32C reverse when the magnetic field BZ is negative, i.e., when the direction of the magnetic field BZ reverses.

The magnetic field BZ that is formed by the Z-axis trapping coil 222z is symmetric on the central Z-axis Az. Therefore, the following Equation 3 is satisfied.

$$dBZ_X/dx = dBZ_Y/dy \quad (3)$$

Based on Equations (2) and (3), the force FZ that the permanent magnet 110 (magnetic dipole moment M) of the capsule endoscope 100 receives due to the magnetic field BZ, which is formed by the Z-axis trapping coil 222z, is represented by the following Equation (4).

$$\begin{pmatrix} FZx \\ FZy \\ FZz \end{pmatrix} = \begin{pmatrix} M_X\left(\frac{dBZ_X}{dx}\right) \\ M_X\left(\frac{dBZ_X}{dx}\right) \\ M_X\left(\frac{dBZ_Z}{dz}\right) \end{pmatrix} \quad (4)$$

Based on Equation (1), a force FX that the magnetic dipole moment M receives from a magnetic field (regarded as a magnetic field BX) formed by the X-axis trapping coil 222x of the trapping magnetic field generating coil 222 is represented by the following Equation (5).

$$\begin{pmatrix} FZx \\ FZy \\ FZz \end{pmatrix} = \begin{pmatrix} M_X\left(\frac{dBX_X}{dx}\right) + M_Y\left(\frac{dBX_Y}{dx}\right) + M_Z\left(\frac{dBX_Z}{dx}\right) \\ M_X\left(\frac{dBX_X}{dy}\right) + M_Y\left(\frac{dBX_Y}{dy}\right) + M_Z\left(\frac{dBX_Z}{dy}\right) \\ M_X\left(\frac{dBX_X}{dz}\right) + M_Y\left(\frac{dBX_Y}{dz}\right) + M_Z\left(\frac{dBX_Z}{dz}\right) \end{pmatrix} \quad (5)$$

Figure 33A:
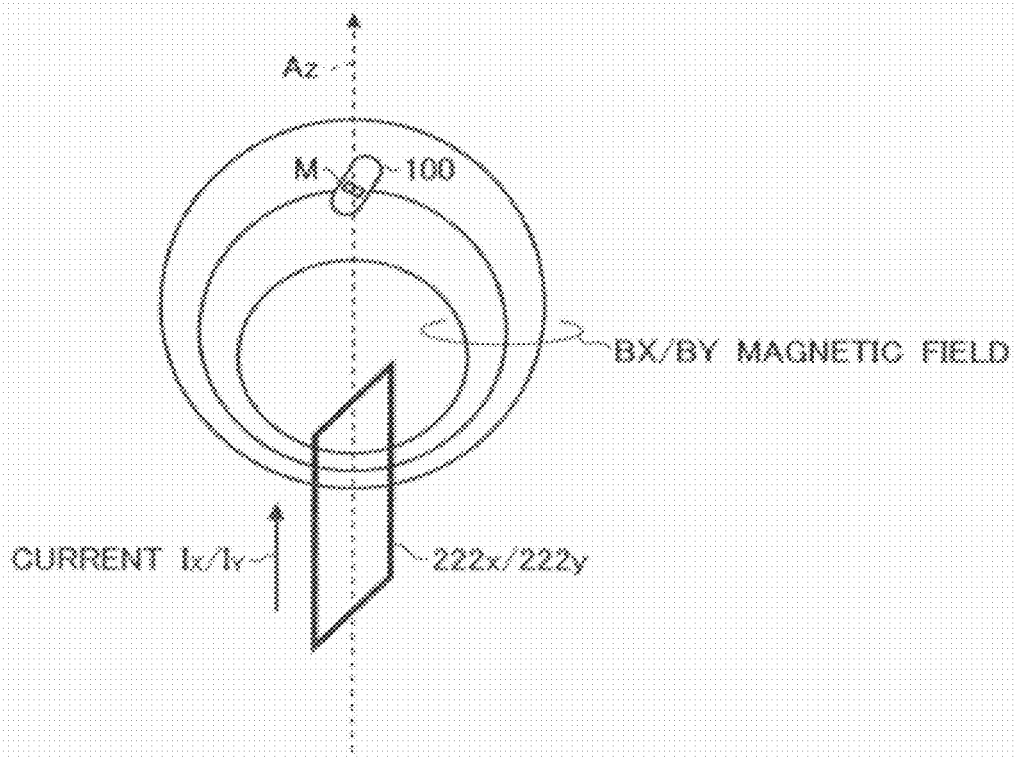
FIG. 33A is a schematic diagram of a magnetic field that is formed near the central Z-axis by the X-axis trapping coil when a current is applied to the X-axis trapping coil in the second embodiment of the present invention.
Figure 33B:
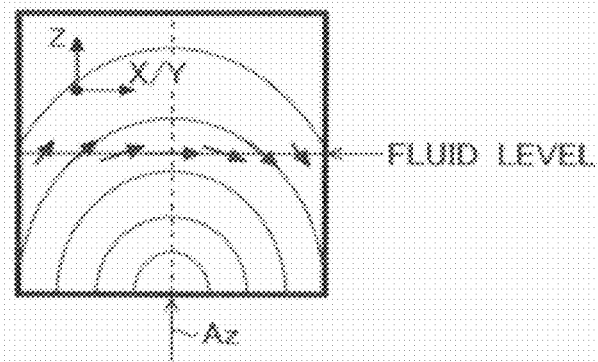
FIG. 33B is a diagram representing a component of the magnetic field shown in FIG. 33A on a plane including the central Z-axis.
Figure 34A:
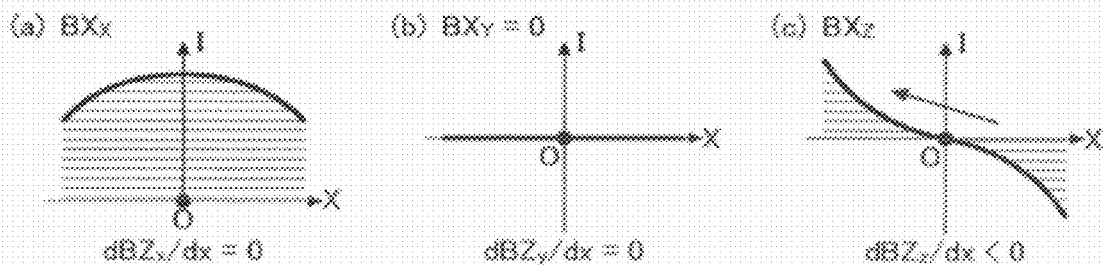
FIG. 34A is a diagram representing the intensity of the magnetic field shown in FIGS. 33A and 33B in the X-axis direction.
Figure 34B:
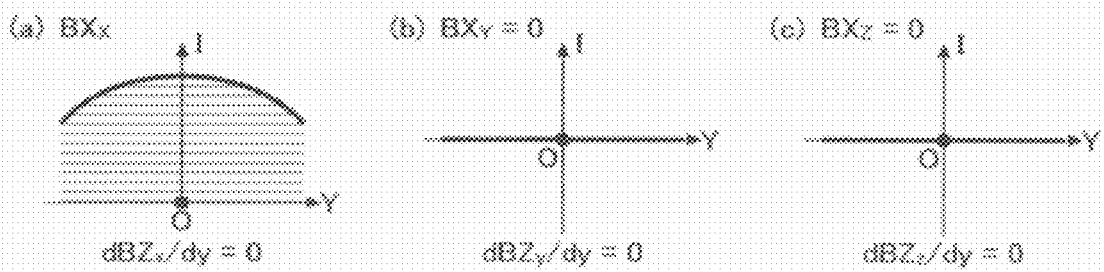
FIG. 34B is a diagram representing the intensity of the magnetic field shown in FIGS. 33A and 33B in the Y-axis direction.
Figure 34C:
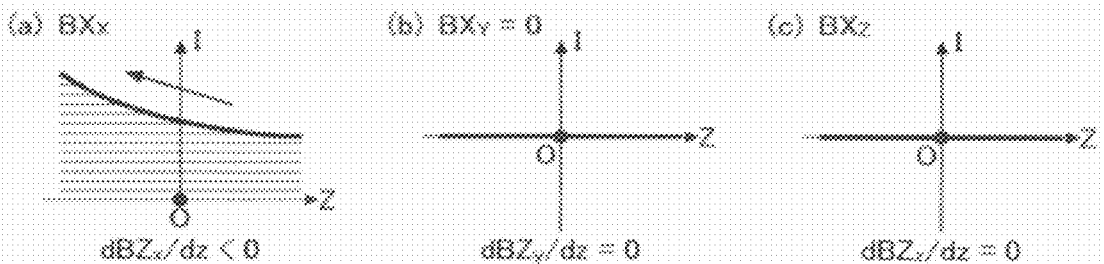
FIG. 34C is a diagram representing the intensity of the magnetic field shown in FIGS. 33A and 33B in the Z-axis direction.

The magnetic field BX that is generated near the central Z-axis Az by the X-axis trapping coil 222x is examined below. FIG. 33A is a schematic diagram of the magnetic field BX that is formed near the central Z-axis Az by the X-axis trapping coil 222x when a current 1x is applied to the X-axis trapping coil 222x in the second embodiment. FIG. 33B is a diagram representing a component of the magnetic field BX shown in FIG. 33A on a plane including the central Z-axis Az. FIG. 34A is a diagram representing the intensity of the magnetic field BX in the X-axis direction FIG. 34B is a diagram representing the intensity of the magnetic field BX in the Y-axis direction. FIG. 34C is a diagram representing the intensity of the magnetic field BX in the Z-axis direction. FIGS. 34A to 34C represent the intensity of the magnetic field BX in each axis direction in the case where the magnetic field BX is positive. An origin O shown in FIGS. 34A to 34C is the intersection between the central Z-axis Az and an arbitrary X-Y plane (for example, the fluid level of the liquid 910).

As shown in FIGS. 33A and 33B, when the current 1x is input to the X-axis trapping coil 222x, the magnetic field BX whose magnetic field lines are perpendicular to the central Z-axis Az on the central Z-axis Az and rotate in the downward direction from the upward direction as they deviate from the central Z-axis Az is formed on the plane including the central Z-axis Az and near the fluid level of the liquid 910.

The intensity (gradient) of the magnetic field BX on the X-axis is as shown in FIG. 34A. A portion (a) of FIG. 34A represents the intensity $BX_X$ of a component in the X-axis direction of the magnetic field BX on the X-axis. A portion (b) of FIG. 34A represents the intensity $BX_Y$ of a component in the Y-axis direction of the magnetic field BX on the X-axis. A portion (c) of FIG. 34A represents the intensity $BX_Z$ of a component in the Z-axis direction of the magnetic field BX on the X-axis.

As shown in (a) of FIG. 34A, the distribution of the intensity $BX_X$ of the component in the X-axis direction of the magnetic field BX on the X-axis is such that the peak of the intensity $BX_X$ is at the origin O on the X-axis, thereby forming a swelling shape. As shown in (c) of FIG. 34A, the positive/negative value of the intensity $BX_Z$ of the component in the Z-axis direction of the magnetic field BX on the X-axis, i.e., the direction of the component, reverse at the border of the origin O on the X-axis. The absolute value of the intensity $BX_Z$ on the X-axis becomes large as the position deviates from the origin O. Accordingly, the intensity $BX_Z$ near the origin O (for example, near the intersection between the central Z-axis Az and the fluid level of the liquid 910) has a gradient with which the magnetic dipole moment M (the permanent magnet 110) is attracted to the −X side. As shown in (b) of FIG. 34A, the intensity $BX_Y$ of the component on the Y-axis of the magnetic field BX in the X-axis direction is $0 (BX_Y=0)$.

The intensity (gradient) of the magnetic field BX on the Y-axis is as shown in FIG. 34B. A portion (a) of FIG. 34B represents the intensity $BX_X$ of a component in the X-axis direction of the magnetic field BX on the Y-axis. A portion (b) of FIG. 34B represents the intensity $BX_Y$ of a component in the Y-axis direction of the magnetic field BX on the Y-axis. A portion (c) of FIG. 34B represents the intensity $BX_Z$ of a component in the Z-axis direction of the magnetic field BX on the Y-axis.

As shown in (a) of FIG. 34B, the distribution of the intensity $BX_X$ of the component in the X-axis direction of the magnetic field BX on the Y-axis is such that the peak of the intensity $BX_X$ is at the origin O on the X-axis, thereby forming a swelling shape. As shown in (b) and (c) of FIG. 34B, the intensity $BX_Y$ of the component in the Y-axis direction of the magnetic field BX on the Y-axis and the intensity $BX_Z$ of the component in the Z-axis direction of the magnetic field BX on the Y-axis are respectively $o(BX_Y=0, BX_Z=0)$.

The intensity (gradient) of the magnetic field BX on the Z-axis is as shown in FIG. 34C. A portion (a) of FIG. 34C represents the intensity $BX_X$ of a component in the X-axis direction of the magnetic field BX on the Z-axis. A portion (b) of FIG. 34C represents the intensity $BX_Y$ of a component in the Y-axis direction of the magnetic field BX on the Z-axis. A portion (c) of FIG. 34C represents the intensity $BX_Z$ of a component in the Z-axis direction of the magnetic field BX on the Z-axis.

As shown in (a) of FIG. 34C, the intensity $BX_X$ of the component in the X-axis direction of the magnetic field BX on the Z-axis is similar to the intensity $BZ_Z$ of the component in the Z-axis direction of the magnetic field BZ on the Z-axis, which is represented by (c) of FIG. 32C. As shown in (b) of FIG. 34C and (c) of FIG. 34B, the intensity $BX_Y$ of the component in the Y-axis direction of the magnetic field BX on the Z-axis and the intensity $BX_Z$ of the component on the Z-axis of the magnetic field BX in the Z-axis direction are respectively $0(BX_Y=0, BX_Z=0)$.

Because the magnetic field BY that is formed near the central Z-axis Az by the Y-axis trapping coil 222$y$ is same as that formed by the X-axis trapping coil 222$x$ described above, detailed explanation for the magnetic field BY is omitted.

The forces FX and FY that are applied to the permanent magnet 110 (magnetic dipole moment M) of the capsule endoscope 100 by the X-axis trapping coil 222$x$ and the Y-axis trapping coil 222$y$ are represented by the following Equations (6) and (7).

$$\begin{pmatrix} FXx \\ FXy \\ FXz \end{pmatrix} = \begin{pmatrix} M_Z\left(\frac{dBX_Z}{dx}\right) \\ 0 \\ M_X\left(\frac{dBX_X}{dz}\right) \end{pmatrix} \quad (6)$$

$$\begin{pmatrix} FYx \\ FYy \\ FYz \end{pmatrix} = \begin{pmatrix} 0 \\ M_Z\left(\frac{dBY_Z}{dy}\right) \\ M_Y\left(\frac{dBY_Y}{dz}\right) \end{pmatrix} \quad (7)$$

Based on Equations (4), (6), and (7), a force F that the permanent magnet 110 (magnetic dipole moment M) of the capsule endoscope 100 receives due to the magnetic field B (trapping magnet field Btrap/shifted peak trapping magnetic field Bstrp) formed by the trapping magnetic field generating coil 222 is represented by the following Equation (8).

$$\begin{pmatrix} Fx \\ Fy \\ Fz \end{pmatrix} = \begin{pmatrix} M_X\left(\frac{dBZ_X}{dx}\right) + M_Z\left(\frac{dBX_Z}{dx}\right) \\ M_Y\left(\frac{dBZ_Y}{dy}\right) + M_Z\left(\frac{dBY_Z}{dy}\right) \\ M_X\left(\frac{dBX_X}{dz}\right) + M_Y\left(\frac{dBY_Y}{dz}\right) + M_Z\left(\frac{dBZ_Z}{dz}\right) \end{pmatrix} \quad (8)$$

An X component Fx and a Y component Fy of the force F are focused below. When the X component Fx is 0 (Fx=0), i.e., when the capsule endoscope 100 is positioned on the central Z-axis Az, the positive/negative value of the forces $Mx(dBZ_X/dx)$ and $M_Z(dBX_Z/dx)$ that are applied to the permanent magnet 110 by each term of $dBX_Z/dx$ and $dBZ_X/dx$ reverse.

When the magnetic field BX that is formed by the X-axis trapping coil 222$x$ is positive (BX>0), the X component of the magnetic dipole moment M is positive ($M_X>0$) and $dBX_Z/dx$ is negative ($dBX_Z/dx<0$). In contrast, when the magnetic field BX is negative (BX<0), the X component of the magnetic dipole moment M is negative ($M_X<0$) and $dBX_Z/dx$ is positive ($dBX_Z/dx>0$). In other words, the signs of Mx and $dBX_Z/dx$ are always opposite.

Similarly, when the magnetic field BY that is formed by the Y-axis trapping coil 222$y$ is positive (BY>0), the Y component of the magnetic dipole moment M is positive ($M_Y>0$) and $dBY_Z/dy$ is negative ($dBY_Z/dy<0$). In contrast, when the magnetic field BY is negative (BY<0), the Y component of the magnetic dipole moment M is negative ($M_Y<0$) and $dBY_Z/dy$ is positive ($dBY_Z/dy>0$). In other words, the signs of $M_Y$ and $dBY_Z/dy$ are always opposite.

When the magnetic field BZ that is formed by the Z-axis trapping coil 222$z$ is positive (BZ>0), the Z component of the magnetic dipole moment M is positive ($M_Z>0$) and $dBZ_X/dx$ is positive ($dBZ_X/dx>0$). In contrast, when the magnetic field BZ is negative (BZ<0), the Z component of the dipole moment M is negative ($M_Z<0$) and $dBZ_X/dx$ is negative ($dBZ_X/dx<0$). In other words, the signs of $M_Z$ and $dBZ_X/dx$ (=$dBZ_Y/dy$ (Equation (3))) are always the same.

Therefore, the positive/negative value of the terms of $M_X(dBZ_X/dx)$ and $ME(dBX_Z/dx)$ of Fx are opposite regardless of the positive/negative value of BX and BZ. In addition, the positive/negative value of the terms of $My(dBZ_Y/dy)$ and $M_Z(dBY_Z/dy)$ of Fy are opposite regardless of the positive/negative value of BY and BZ.

When BZ is larger than BX, the balance between $Mx(dBZ_X/dx)$ and $M_Z(dBX_Z/dx)$ lowers, so that a force in the direction of Fx can be generated. In contrast, when BZ is smaller than BX, a force in the direction opposite to that of Fx can be generated.

When BZ is larger than BY, the balance between $M_Y(dBZ_Y/dy)$ and $M_Z(dBY_Z/dy)$ lowers, so that a force in the direction of Fy can be generated. In contrast, when BZ is smaller than BY, a force in the direction opposite to that of Fy can be generated.

By adjusting the balance between the currents of trapping signals to be input to the X-axis trapping coil 222$x$, the Y-axis trapping coil 222$y$, and the Z-axis trapping coil 222$z$, the trapping magnetic field Btrap whose peak is on the central Z-axis Az and the shifted peak trapping magnetic field Bstrp whose peak is shifted in a target direction can be appropriately formed.

In the second embodiment, as described above, when the relative position between the subject 900 and the central Z-axis Az of the trapping magnetic field generating coil 222 is changed, the peak of the trapping magnetic field Btrap, which traps the capsule endoscope 100 (specifically, the permanent magnet 110), is shifted in the direction same as or opposite to that in which the relative position is changed (the shifted peak trapping magnetic field Bstrp). In other words, the shifted peak trapping magnetic field Bstrp that includes the trapping magnetic field component (the trapping magnetic field Btrap) that attracts the permanent magnet 110 to the central Z-axis Az and the gradient magnetic field component (the gradient magnetic field Bgrad) that attracts the permanent magnet 110 in the direction same as or opposite to that in which the relative position is changed is formed in the detecting space K in which the subject 900 is laid. Therefore, in the second embodiment, deviation of the capsule endoscope 100 from the central Z-axis Az is reduced when the relative position is changed. Accordingly, the state where the capsule endoscope 100 is trapped in a desirable position can be maintained accurately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A guiding system comprising:
   a capsule-type apparatus that includes:
      a capsule-shaped casing adapted to be introduced into a subject, and
      a permanent magnet which is fixed to the capsule-shaped casing; and
   a position controlling apparatus that includes:
      a relative position controlling mechanism that changes a relative position between a predetermined axis and the subject,
      a first magnetic field generating mechanism that forms, in a space in which the subject is laid, a component of a trapping magnetic field that attracts the permanent magnet to the predetermined axis,
      a second magnetic field generating mechanism that forms, in the space in which the subject is laid, a component of a gradient magnetic field that attracts the permanent magnet in a direction same as or opposite to a direction in which the relative position is changed, and
      a controller that is adapted to control the first magnetic field generating mechanism to form the component of the trapping magnetic field and is further adapted to control the second magnetic field generating mechanism to form the component of the gradient magnetic field in addition to the component of the trapping magnetic field formed by the first magnetic field generating mechanism when the position of the predetermined axis with respect to the capsule-type apparatus is at least one of moved, accelerated, and decelerated,
   wherein the controller is adapted to calculate a drive signal for driving the relative position controlling mechanism, and is further adapted to calculate, based on the calculated driving signal for the relative position controlling mechanism, a gradient signal for causing the second magnetic field generating mechanism to generate the gradient magnetic field for cancelling at least one of inertia force, force caused by wave breaking of a liquid in which the capsule-type apparatus is adapted to float within the subject, and friction force between the capsule-type apparatus and the liquid, when the position of the predetermined axis with respect to the capsule-type apparatus is at least one of moved, accelerated, and decelerated, and
   wherein the second magnetic field generating mechanism generates the gradient magnetic field based on the gradient signal calculated by the controller thereby inhibiting the capsule-type apparatus from deviating from the predetermined axis.

2. The guiding system according to claim 1, wherein the component of the gradient magnetic field attracts the permanent magnet in the direction in which the relative position of the predetermined axis is changed.

3. The guiding system according to claim 2, wherein the controller is adapted to control the second magnetic field generating mechanism to form the component of the gradient magnetic field to have an increased intensity when the relative position controlling mechanism moves the relative position with acceleration.

4. The guiding system according to claim 1, wherein the component of the gradient magnetic field attracts the permanent magnet in the direction opposite to the direction in which the relative position of the predetermined axis is changed.

5. The guiding system according to claim 4, wherein the controller is adapted to control the second magnetic field generating mechanism to form the component of the gradient magnetic field to have an increased intensity when the relative position controlling mechanism moves the relative position with deceleration.

6. The guiding system according to claim 1, wherein:
   the first magnetic field generating mechanism includes a Z-axis coil whose central axis coincides with the predetermined axis, an X-axis coil whose central axis is perpendicular to the predetermined axis, and a Y-axis coil whose central axis is perpendicular to the predetermined axis, the X-axis coil and the Y-axis coil being orthogonal with each other, and
   the relative position controlling mechanism changes the relative position in a direction perpendicular to the predetermined axis.

7. The guiding system according to claim 1, wherein:
   the second magnetic field generating mechanism includes:
      a gradient magnetic field generating coil that includes:
         a pair of X-axis gradient coils that each form a magnetic field in a direction approximately perpendicular to the predetermined axis on the predetermined axis, and
         a pair of Y-axis gradient coils that each generate a magnetic field that is approximately perpendicular to the predetermined axis and approximately perpendicular to the magnetic field generated by the pair of X-axis gradient coils on the predetermined axis,
   the relative position controlling mechanism changes the relative position in a direction perpendicular to the predetermined axis, and
   the controller, to form the magnetic field including the component of the gradient magnetic field in the space, is adapted to control the second magnetic field generating mechanism to generate a gradient magnetic field in a direction of the magnetic field generated on the predetermined axis by the pair of X-axis gradient coils by adjusting a balance in intensity between the magnetic fields generated by the pair of X-axis gradient coils, and to generate a gradient magnetic field in a direction of the magnetic field generated on the predetermined axis by the pair of Y-axis gradient coils by adjusting a balance in intensity between the magnetic fields generated by the pair of Y-axis gradient coils.

8. The guiding system according to claim 1, wherein the position of the predetermined axis with respect to the subject is changed by moving the subject or the first magnetic field generating mechanism.

9. A position controlling apparatus for guiding a position of a capsule-type apparatus that is introduced into a subject, the capsule-type apparatus including a capsule-shaped casing, and a permanent magnet fixed to the capsule-shaped casing, the position controlling apparatus comprising:
- a relative position controlling mechanism that changes a relative position between a predetermined axis and the subject;
- a first magnetic field generating mechanism that forms, in a space in which the subject is laid, a component of a trapping magnetic field that attracts the permanent magnet to the predetermined axis
- a second magnetic field generating mechanism that forms, in the space in which the subject is laid, a component of a gradient magnetic field that attracts the permanent magnet in a direction same as or opposite to a direction in which the relative position is changed; and
- a controller that is adapted to control the first magnetic field generating mechanism to form the component of the trapping magnetic field and is further adapted to control the second magnetic field generating mechanism to form the component of the gradient magnetic field in addition to the component of the trapping magnetic field formed by the first magnetic field generating mechanism when the position of the predetermined axis with respect to the capsule-type apparatus is at least one of moved, accelerated, and decelerated,
- wherein the controller is adapted to calculate a driving signal for driving the relative position controlling mechanism, and is further adapted to calculate, based on the calculated driving signal for the relative position controlling mechanism, a gradient signal for causing the second magnetic field generating mechanism to generate the gradient magnetic field for cancelling at least one of inertia force, force caused by wave breaking of a liquid in which the capsule-type apparatus is adapted to float within the subject, and friction force between the capsule-type apparatus and the liquid, when the position of the predetermined axis with respect to the capsule-type apparatus is at least one of moved, accelerated, and decelerated, and
- wherein the second magnetic field generating mechanism generates the gradient magnetic field based on the gradient signal calculated by the controller thereby inhibiting the capsule-type apparatus from deviating from the predetermined axis.

10. The position controlling apparatus according to claim 9, wherein the component of the gradient magnetic field attracts the permanent magnet in the direction in which the relative position is changed.

11. The position controlling apparatus according to claim 10, wherein the controller is adapted to control the second magnetic field generating mechanism to form the component of the gradient magnetic field to have an increased intensity when the relative position controlling mechanism moves the relative position with acceleration.

12. The position controlling apparatus according to claim 9, wherein the component of the gradient magnetic field attracts the permanent magnet in the direction opposite to the direction in which the relative position of the predetermined axis is changed.

13. The position controlling apparatus according to claim 12, wherein the controller is adapted to control the second magnetic field generating mechanism to form the component of the gradient magnetic field to have an increased intensity when the relative position controlling mechanism moves the relative position with deceleration.

14. The position controlling apparatus according to claim 9, wherein:
- the first magnetic field generating mechanism includes a Z-axis coil whose central axis coincides with the predetermined axis, an X-axis coil whose central axis is perpendicular to the predetermined axis, and a Y-axis coil whose central axis is perpendicular to the predetermined axis, the X-axis coil and the Y-axis coil being orthogonal with each other, and
- the relative position controlling mechanism changes the relative position in a direction perpendicular to the predetermined axis.

15. The position controlling apparatus according to claim 9, wherein:
- the second magnetic field generating mechanism includes:
  - a gradient magnetic field generating coil that includes:
    - a pair of X-axis gradient coils that each form a magnetic field in a direction approximately perpendicular to the predetermined axis on the predetermined axis, and
    - a pair of Y-axis gradient coils that each generate a magnetic field that is approximately perpendicular to the predetermined axis and approximately perpendicular to the magnetic field generated by the pair of X-axis gradient coils on the predetermined axis,
- the relative position controlling mechanism changes the relative position in a direction perpendicular to the predetermined axis, and
- the controller, to form the magnetic field including the component of the gradient magnetic field in the space, is adapted to control the second magnetic field generating mechanism to generate a gradient magnetic field in a direction of the magnetic field generated on the predetermined axis by the pair of X-axis gradient coils by adjusting a balance in intensity between the magnetic fields generated by the pair of X-axis gradient coils, and to generate a gradient magnetic field in a direction of the magnetic field generated on the predetermined axis by the pair of Y-axis gradient coils by adjusting a balance in intensity between the magnetic fields generated by the pair of Y-axis gradient coils.

16. The position controlling apparatus according to claim 9, wherein the position of the predetermined axis with respect to the subject is changed by moving the subject or the first magnetic field generating mechanism.

17. A method of guiding a position of a capsule-type apparatus that includes a capsule-shaped casing adapted to be introduced into a subject, and a permanent magnet fixed in the capsule-shaped casing, the method comprising:
- a trapping magnetic field generating step of forming a trapping magnetic field that attracts the permanent magnet to a predetermined axis in a space in which the subject is laid;
- a relative position controlling step of calculating a driving signal for changing the relative position between the predetermined axis and the subject;
- a gradient signal calculating step of a computer processor calculating a gradient signal, based on the calculated driving signal, for forming, in the space, a gradient magnetic field that attracts the permanent magnet in a direction same as or opposite to a direction in which the relative position is changed, the gradient magnetic field is for cancelling at least one of inertia force, force caused by wave breaking of a liquid in which the capsule-type apparatus is adapted to float within the subject, and friction force between the capsule-type apparatus and the liquid, when the position of the predetermined axis with respect to the capsule-type apparatus is at least one of moved, accelerated, and decelerated; and a gradient magnetic field generating step of generating the gradient magnetic field based on the calculated gradient signal in addition to the trapping magnetic field generated in the trapping magnetic field generating step, thereby inhibiting the capsule-type apparatus from deviating from the predetermined axis.

18. The method according to claim 17, wherein the gradient magnetic field attracts the permanent magnet in the direction in which the relative position of the predetermined axis is changed.

19. The method according to claim 18, wherein the gradient magnetic field generating step forms, in the space, the magnetic field that includes the component of the gradient magnetic field to have an increased intensity when the relative position is moved with acceleration.

20. The method according to claim 17, wherein the gradient magnetic field attracts the permanent magnet opposite to the direction in which the relative position of the predetermined axis is changed.

21. The method according to claim 20, wherein the gradient magnetic field generating step forms, in the space, the magnetic field that includes a component of the gradient magnetic field to have an increased intensity when the relative position is moved with deceleration.

* * * * *